United States Patent
Givechian et al.

(10) Patent No.: US 12,412,639 B2
(45) Date of Patent: *Sep. 9, 2025

(54) METHOD OF CHARACTERIZING A TUMOR BASED ON AN IMMUNE GENE EXPRESSION SIGNATURE IN REGULATORY T CELL (Treg)-ENRICHED TUMOR SAMPLES

(71) Applicants: Nantomics LLC, Culver City, CA (US); NantBio, Inc., Culver City, CA (US); Nant Holdings IP, LLC, Culver City, CA (US)

(72) Inventors: Kevin B. Givechian, Irvine, CA (US); Kamil A. Wnuk, Playa Vista, CA (US); Chad Garner, Culver City, CA (US); Stephen Charles Benz, Culver City, CA (US); Hermes J. Garban, Culver City, CA (US); Shahrooz Rabizadeh, Agoura Hills, CA (US); Kayvan Niazi, Culver City, CA (US); Patrick Soon-Shiong, Culver City, CA (US)

(73) Assignees: NantOmics, LLC, Culver City, CA (US); NantBio, Inc., Culver City, CA (US); Nant Holdings IP, LLC, Culver City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/359,437

(22) Filed: Jul. 26, 2023

(65) Prior Publication Data
US 2023/0377686 A1 Nov. 23, 2023

Related U.S. Application Data

(62) Division of application No. 16/767,366, filed as application No. PCT/US2018/067319 on Dec. 21, 2018, now Pat. No. 11,756,651.

(60) Provisional application No. 62/613,560, filed on Jan. 4, 2018.

(51) Int. Cl.
*G16B 25/10* (2019.01)
*C12Q 1/6886* (2018.01)

(52) U.S. Cl.
CPC .......... *G16B 25/10* (2019.02); *C12Q 1/6886* (2013.01); *C12Q 2600/106* (2013.01); *C12Q 2600/118* (2013.01); *C12Q 2600/158* (2013.01)

(58) Field of Classification Search
CPC .............. G16B 25/10; C12Q 1/6886; C12Q 2600/106; C12Q 2600/118; C12Q 2600/158
See application file for complete search history.

(56) References Cited

FOREIGN PATENT DOCUMENTS

| WO | 2017114851 A1 | 7/2017 |
|---|---|---|
| WO | 2019135957 A1 | 7/2019 |

OTHER PUBLICATIONS

Linsley PS, et al. (2015) PLOS One. 10(9): e0138726. (https://doi.org/10.1371/journal.pone.0138726).*
Charoentong P, et al. (Jan. 3, 2017) Cell Reports. 18:248-262.*
Van de Ven K and Borst J (2015) Immunotherapy. 7(6), 655-667. (https://doi.org/10.2217/imt.15.32).*
Clyde, D., "Keeping score with immunotherapy response", 2017, Nature Reviews Genetics vol. 18, p. 146.
Zheng, et al., "Landscape of Infiltrating T Cells in Liver Cancer Revealed by Single-Cell Sequencing", 2017, Cell 169, 1342-1356.
Vanneman, et al., "Combining Immunotherapy and Targeted Therapies in Cancer Treatment", Nat Rev Cancer; 12(4): 237-251, (2012).
Linsley et al., "The relationship of immune cell signatures to patient survival varies within and between tumor types", PLoS One, Sep. 23, 2015, vol. 10, No. 9, e0138726 (pp. 1-19).
Donson et al., "Increased immune gene expression and immune cell infiltration in high-grade astrocytoma distinguish long-term from short-term survivors", The Journal of Immunology, 2012, vol. 189, pp. 1920-1927.
Givechian et al., "Identification of an immune gene expression signature associated with favorable clinical features in Treg-enriched patient tumor samples", NPJ Genomic Medicine, Epub. Jun. 13, 2018, vol. 3, Article No. 14, pp. 1-12.
International Search Report and Written Opinion received for PCT Application No. PCT/US2018/067319 dated Apr. 23, 2019, 15 pages.
International Preliminary Report on Patentability received for PCT Application No. PCT/US2018/067319 dated Jul. 16, 2020, 10 pages.

* cited by examiner

*Primary Examiner* — Robert S Landsman
(74) *Attorney, Agent, or Firm* — Umberg Zipser LLP; Martin Fessenmaier; Priti Phukan

(57) ABSTRACT

An immune gene expression signature is associated with favorable clinical features in Treg-enriched tumor samples and can be used to predict immunogenicity of a tumor, overall survival, and/or chemosensitivity.

16 Claims, 55 Drawing Sheets

Fig. 2 continued

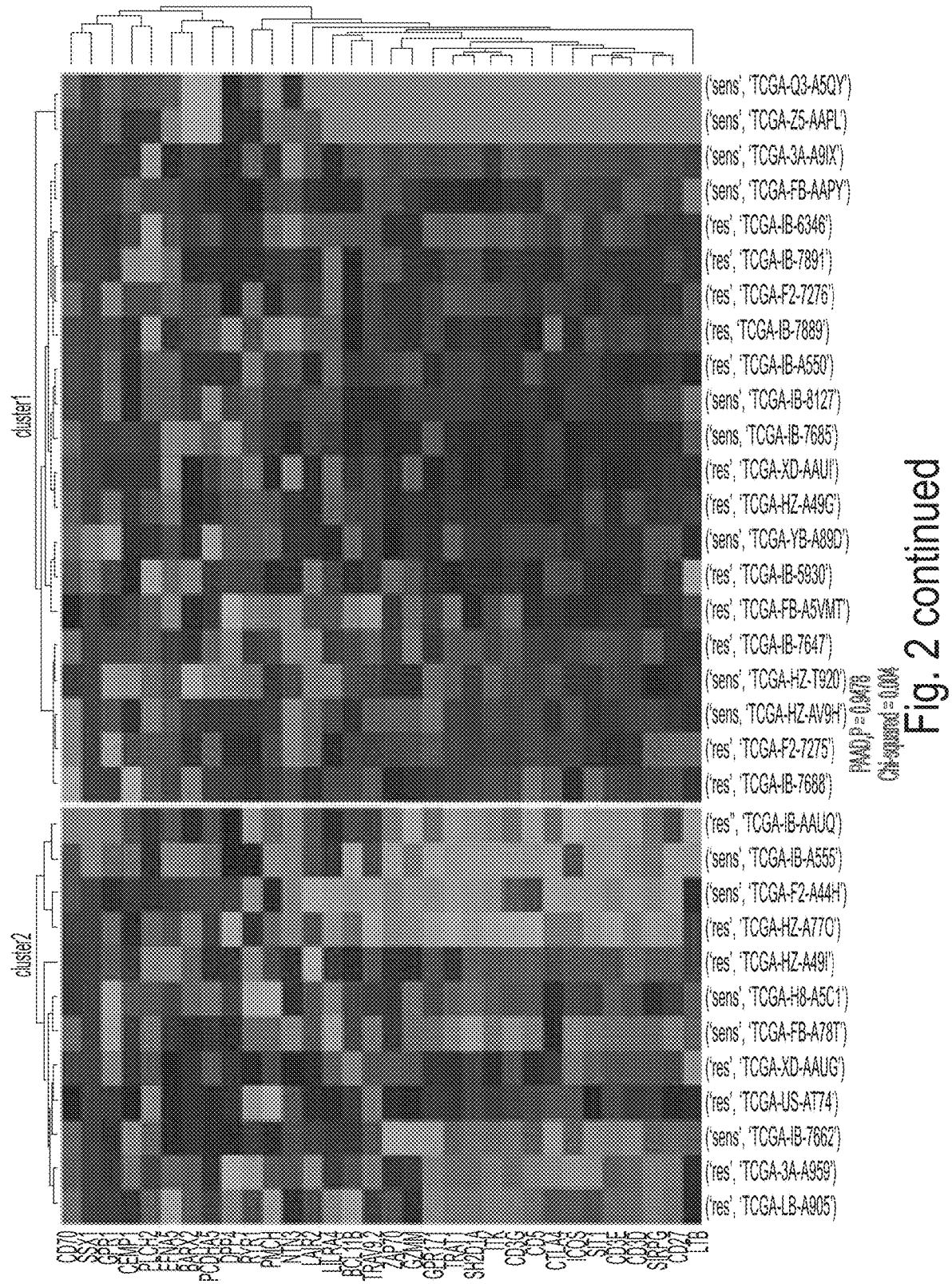

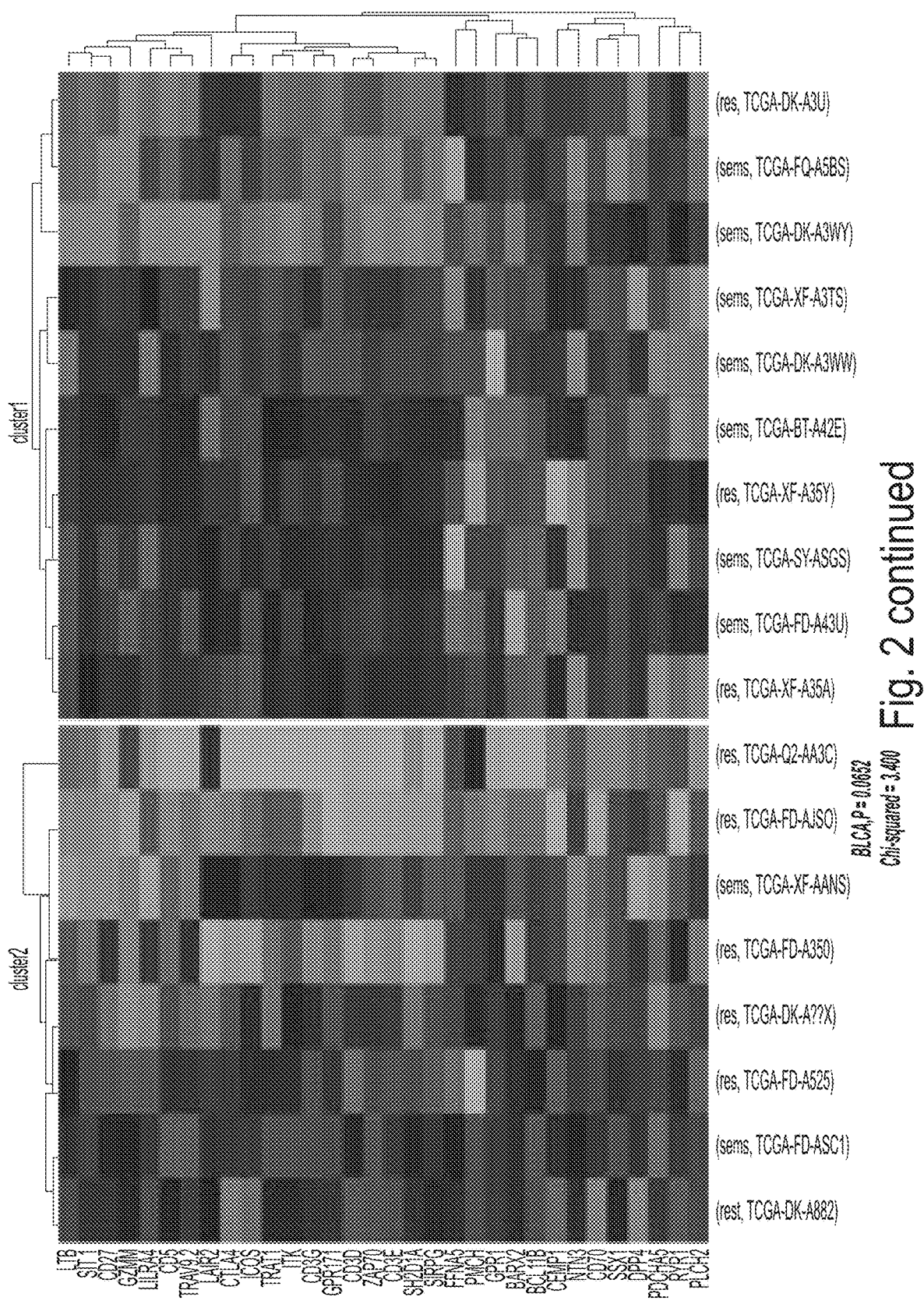

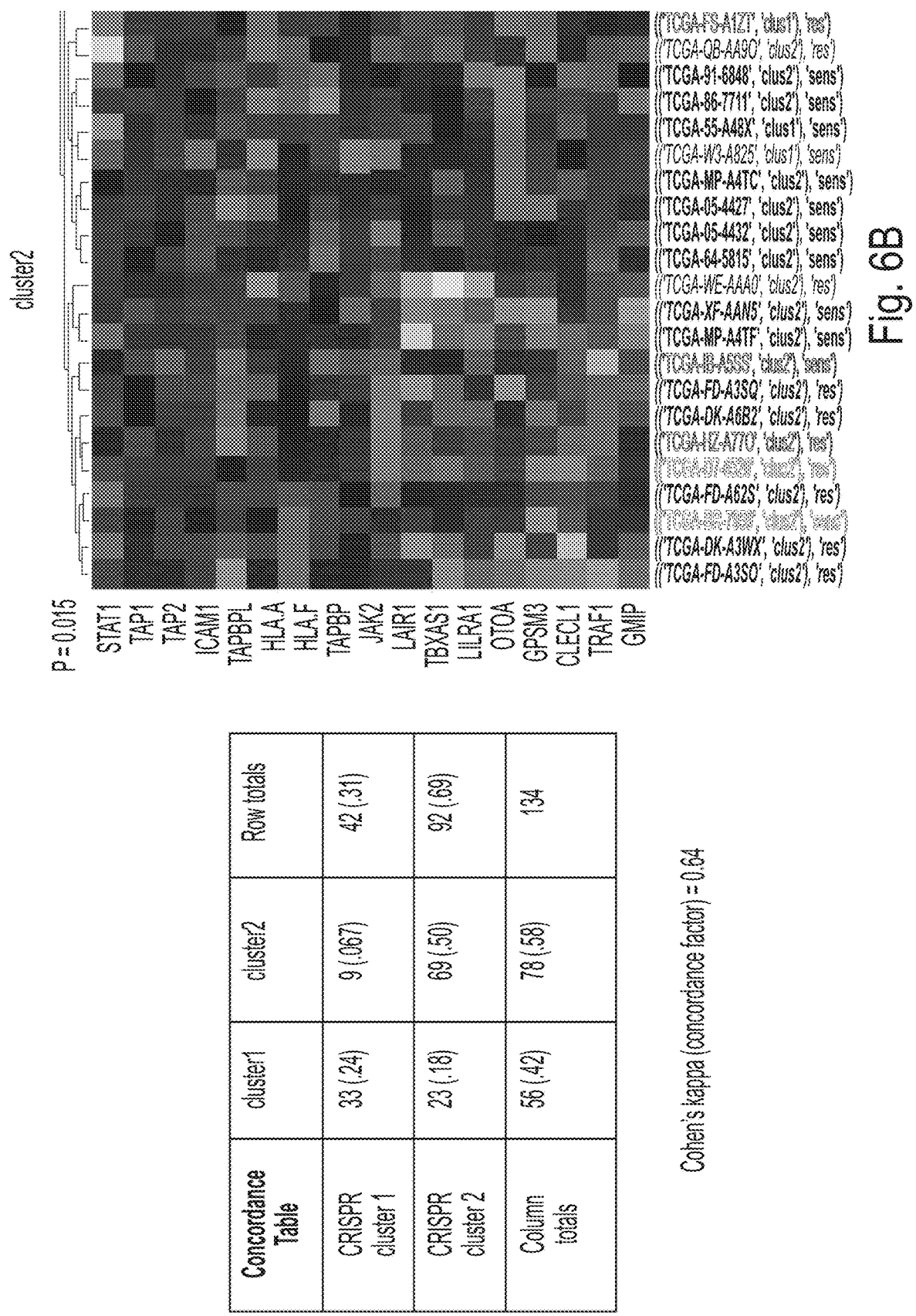

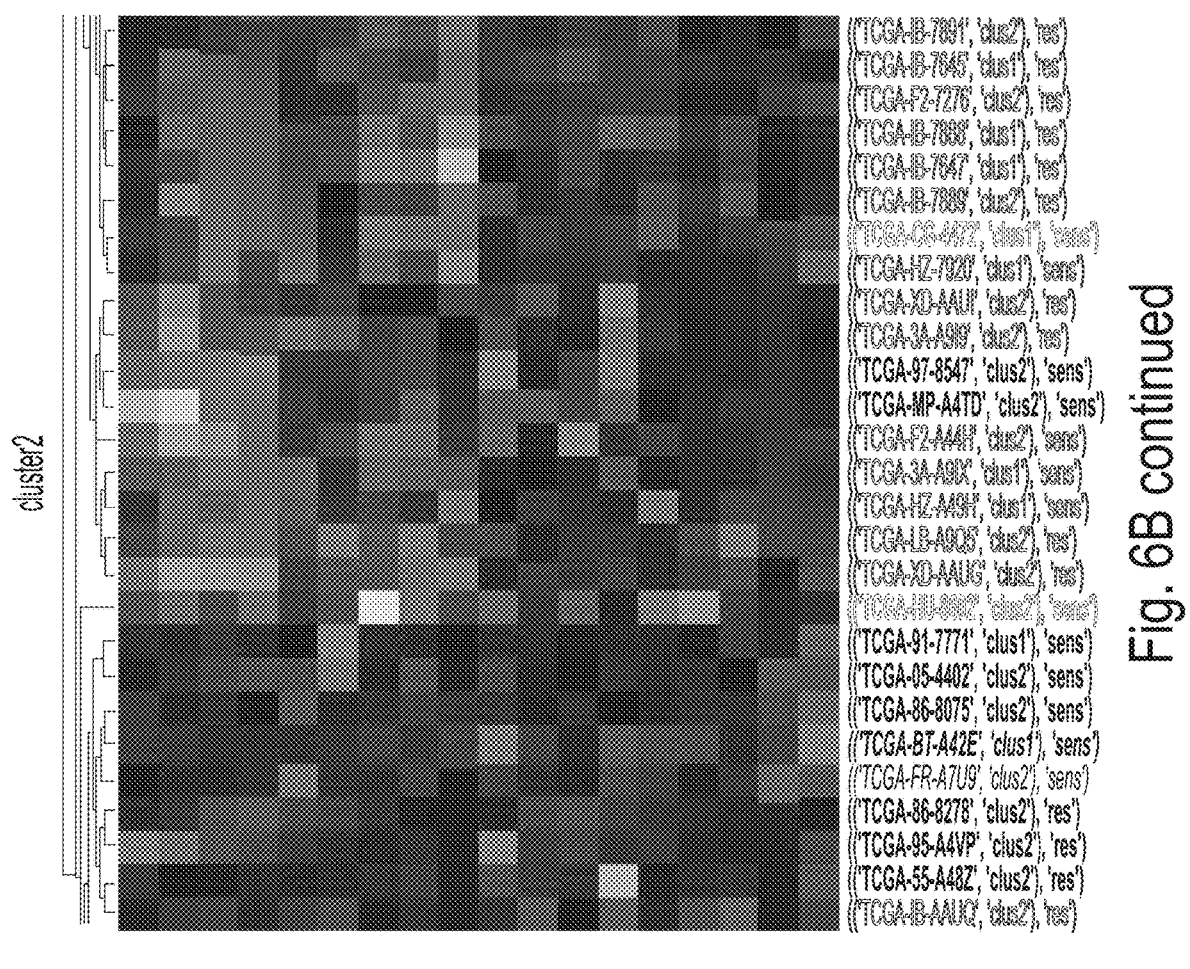

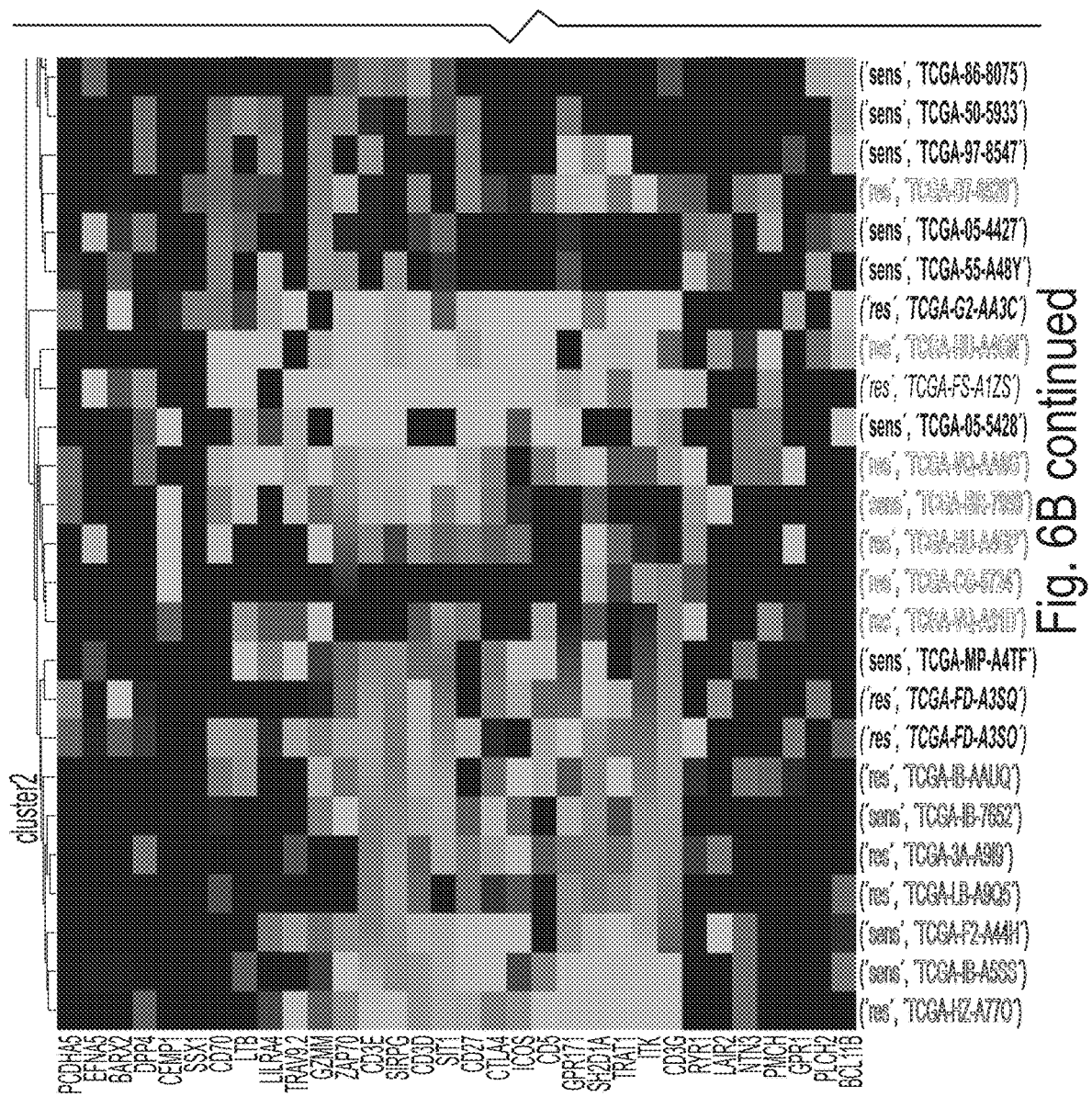

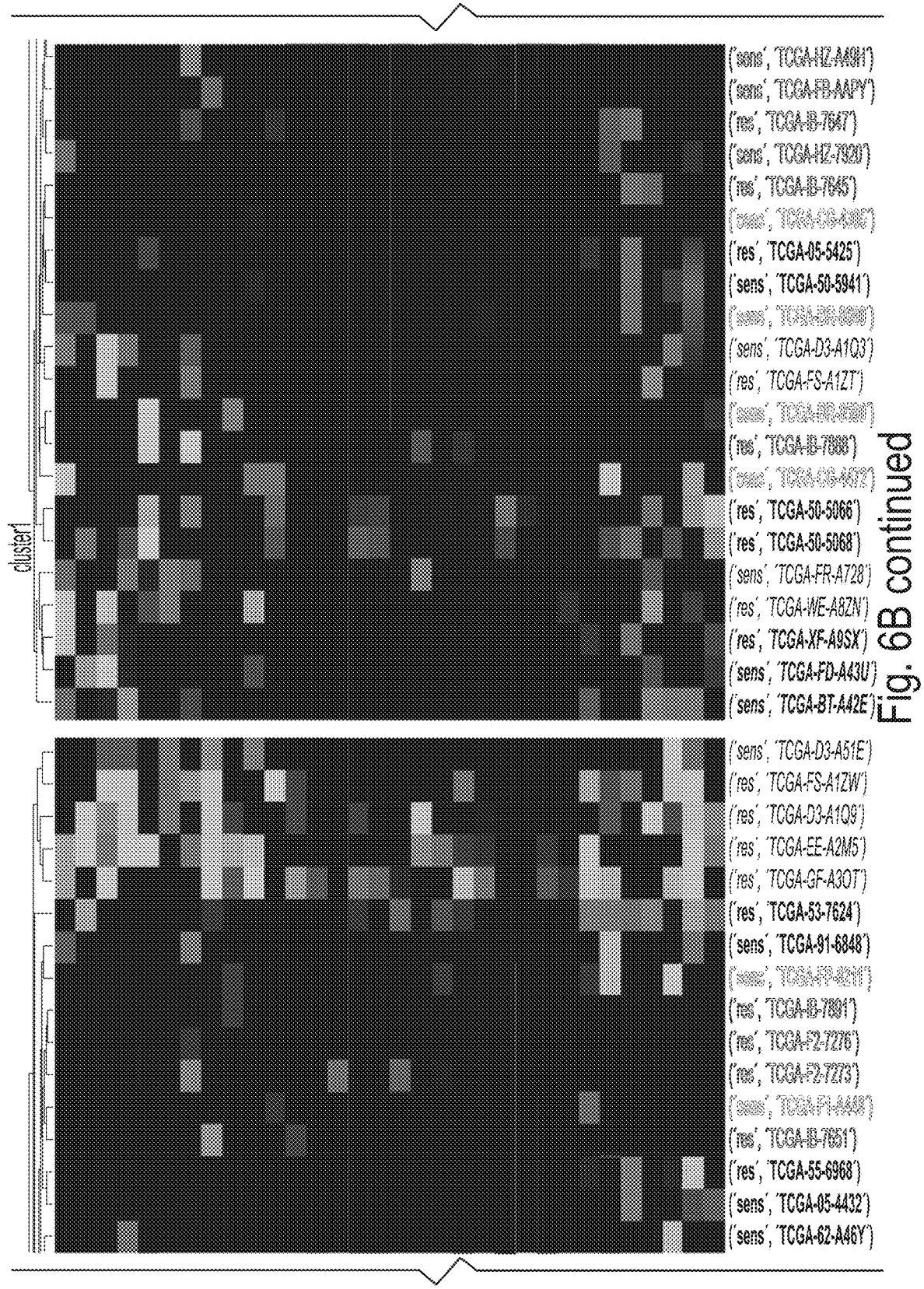

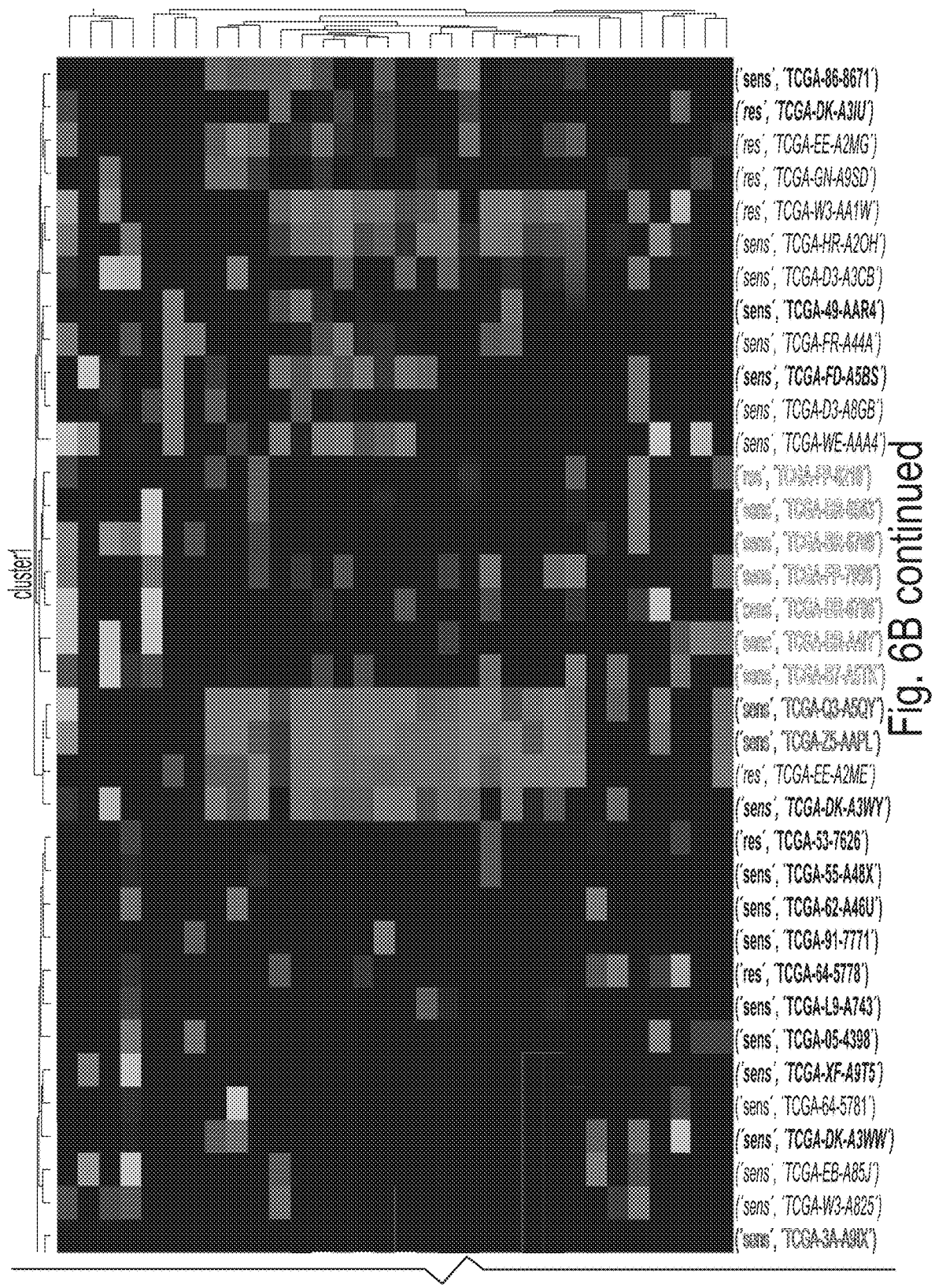

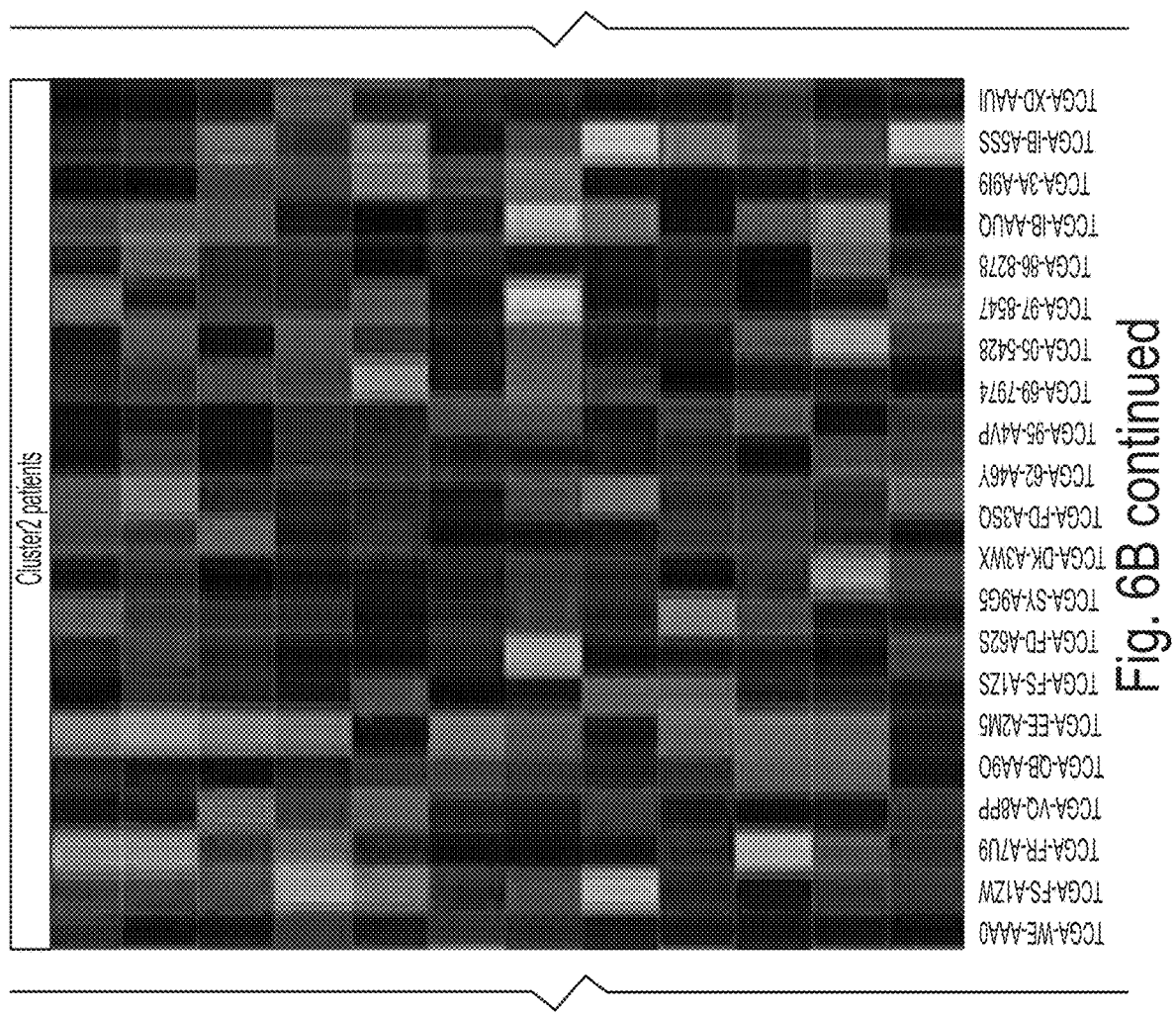

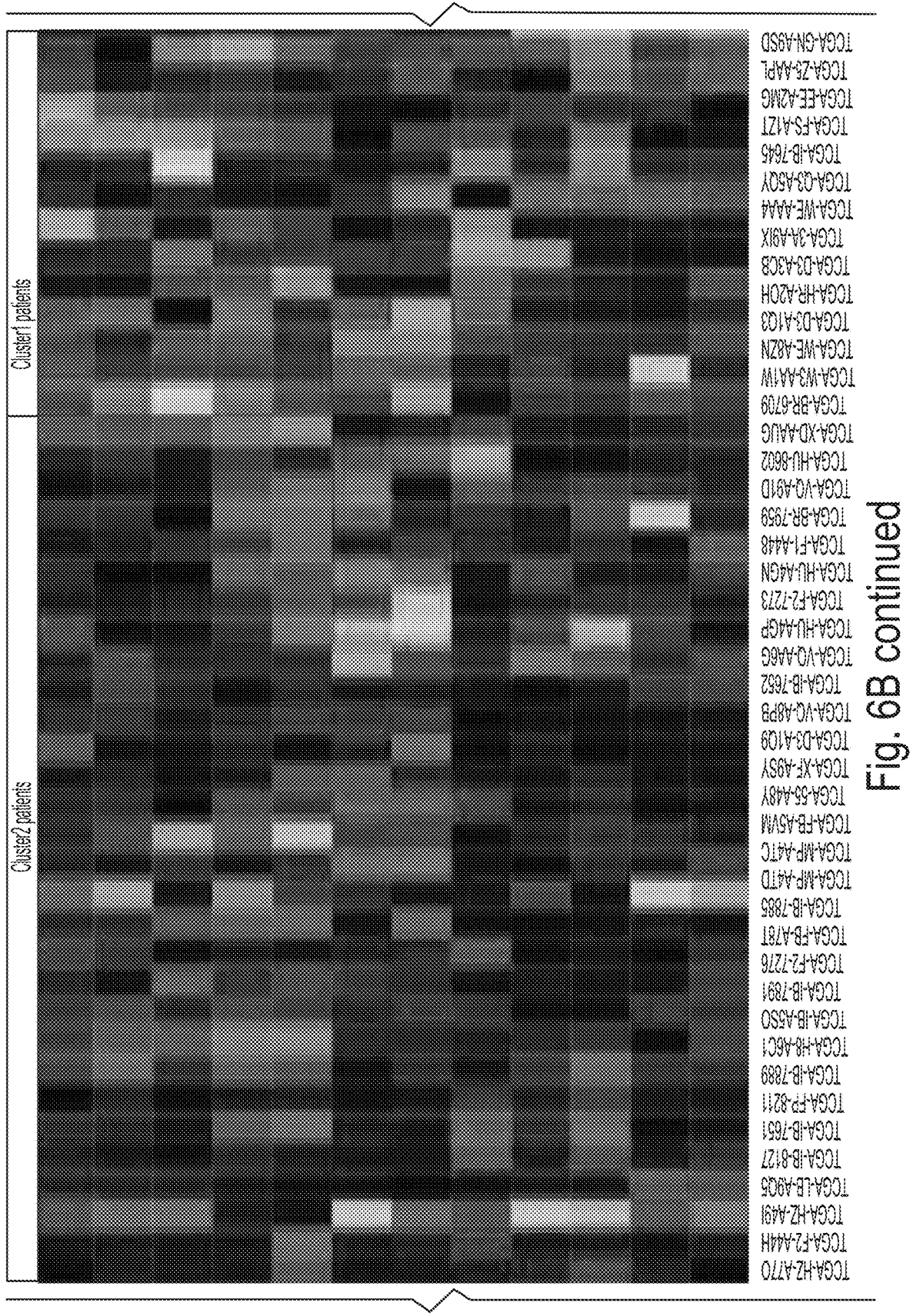

METHOD OF CHARACTERIZING A TUMOR BASED ON AN IMMUNE GENE EXPRESSION SIGNATURE IN REGULATORY T CELL (Treg)-ENRICHED TUMOR SAMPLES This application is a divisional application of U.S. patent application Ser. No. 16/767,366, which was filed May 27, 2020, and now granted as U.S. Pat. No. 11,756,651, which is a 371 application of PCT/US2018/067319 (now expired), which was filed Dec. 21, 2018, and which claims priority to U.S. provisional patent application Ser. No. 62/613,560 (now expired), which was filed Jan. 4, 2018.

FIELD OF THE INVENTION

The field of the invention is omics analysis of tumor tissue containing Tregs, especially as it relates to gene expression signatures that are associated with an immunogenic tumor microenvironment and/or chemosensitivity and overall survival.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Studies of the tumor microenvironment have surfaced promising avenues of exploration to better understand the clinical relevance of T cell immune biology. Regulatory T cells (Tregs) have keenly emerged in light of their ability to inhibit the adaptive immune response and provide a mechanism of immune escape for cancer cells within the tumor microenvironment across various cancer types. However, the relatively large number of studies exploring the clinical relevance of intratumoral Treg abundance has produced controversial results to date, with some studies finding a poor prognosis associated with Treg infiltration, and others suggesting a favorable Treg-associated prognosis. Not surprisingly, the recent efforts to account for these polarized clinical results have undermined the notion that FOXP3+ Tregs invariably suppress tumor immunity. To address this uncertainty, multiple gene markers were taken into account to more accurately identify Tregs, such as FOXP3+BLIMP1 or FOXP3+CTLA4. However, none of the known studies have produced results that were suitable to guide a clinician towards a rational-based therapy with high confidence in a predicted outcome.

Indeed, immune heterogeneity within the tumor microenvironment has added multiple layers of complexity to the understanding of chemosensitivity and survival across various cancer types. Within the tumor microenvironment, immunogenicity is a favorable clinical feature in part driven by the antitumor activity of CD8+ T cells. However, tumors often inhibit this antitumor activity by exploiting the suppressive function of Regulatory T cells (Tregs), thus suppressing an adaptive immune response.

Therefore, despite relatively detailed knowledge of Tregs and CD8+ T cells in isolation, an accurate prediction of immunogenicity of a tumor enriched with Tregs has remained elusive. Thus, there is still a need for improved systems and methods to better characterize a tumor that includes Tregs.

SUMMARY OF THE INVENTION

The inventive subject matter is directed to various systems and methods of omics analysis and especially expression strength in a tumor sample of at least two, or at least five, or all of PCDHA5, EFNA5, BARX2, DPP4, CEMP1, SSX1, CD70, LTB, LILRA4, TRAV9.2, GZMM, ZAP70, CD3E, SIRPG, CD3D, SIT1, CD27, CTLA4, ICOS, CD5, GPR171, SH2D1A, TRAT1, ITK, CD3G, RYR1, LAIR2, NTN3, PMCH, GPR1, PLCH2, and BCL11B to determine at least one of prolonged overall survival of a patient, immunogenicity of the tumor, and sensitivity of the tumor to chemotherapy. In some embodiments, expression strength typically correlates positively with overall patient survival, immunogenicity of the tumor, and chemosensitivity of the tumor. Contemplated analyses may further include determination of an immunophenoscore of the tumor.

For example, in one contemplated aspect of the inventive subject matter, the inventors contemplate a method of characterizing a tumor that includes a step of quantifying or obtaining expression strength for a plurality of differentially expressed genes, wherein the genes are differentially expressed in immune competent cells in the tumor. In a further step, the expression strengths are associated with a cluster representative of overall patient survival, immunogenicity of the tumor, and/or chemosensitivity of the tumor, and in yet another step, the association is used to thereby characterize the tumor as being associated with prolonged overall patient survival, immunogenicity of the tumor, and chemosensitivity of the tumor. Where desired, contemplated methods may further include a step of calculating an immunophenoscore.

In preferred embodiments, the plurality of differentially expressed genes comprise at least two, or at least five, or all of PCDHA5, EFNA5, BARX2, DPP4, CEMP1, SSX1, CD70, LTB, LILRA4, TRAV9.2, GZMM, ZAP70, CD3E, SIRPG, CD3D, SIT1, CD27, CTLA4, ICOS, CD5, GPR171, SH2D1A, TRAT1, ITK, CD3G, RYR1, LAIR2, NTN3, PMCH, GPR1, PLCH2, and BCL11B. Most typically, the immune competent cells will include CD8+ T cells, CD4+ T cells, M1 macrophages, M2 macrophages, and/or Tregs. As will be readily appreciated, the step of quantifying or obtaining expression strength may use previously obtained transcriptomics data or use quantitative RNA sequencing of nucleic acids obtained from the tumor. Additionally, contemplated methods may include further include a step of administering chemotherapy or immune therapy upon characterization of the tumor as being immunogenic or chemosensitive.

In another aspect of the inventive subject matter, the inventors also contemplate a method of treating a patient diagnosed with a tumor that includes the steps of (a) quantifying or obtaining expression strength for a plurality of differentially expressed genes, wherein the genes are differentially expressed in immune competent cells in the tumor; (b) associating the expression strengths with a cluster representative of overall patient survival, immunogenicity of the tumor, and/or chemosensitivity of the tumor; (c) using the association to thereby characterize the tumor as being associated with prolonged overall patient survival, immunogenicity of the tumor, and chemosensitivity of the tumor; and (d) upon characterization of the tumor as being associated with prolonged overall patient survival, immunogenicity of the tumor, and/or chemosensitivity of the tumor subjecting the patient to chemotherapy or immune therapy.

With respect to the differentially expressed genes and the immune competent cells, the same considerations as noted above apply. Likewise, it is noted that the step of quantifying or obtaining expression strength may use previously obtained transcriptomics data.

Therefore, the inventors also contemplate the use of expression strength data from a tumor sample, wherein the expression strength data are measured or obtained from at least two of PCDHA5, EFNA5, BARX2, DPP4, CEMP1, SSX1, CD70, LTB, LILRA4, TRAV9.2, GZMM, ZAP70, CD3E, SIRPG, CD3D, SIT1, CD27, CTLA4, ICOS, CD5, GPR171, SH2D1A, TRAT1, ITK, CD3G, RYR1, LAIR2, NTN3, PMCH, GPR1, PLCH2, and BCL11B to determine prolonged overall patient survival, immunogenicity of the tumor, and/or chemosensitivity of the tumor.

Most typically, increased expression is associated with the prolonged overall survival, immunogenicity, and/or chemosensitivity. Suitable uses may further comprise a determination of an immunophenoscore of the tumor. Moreover, it is noted that the expression strength may be determined using RNAseq, or that expression strength is determined from previously obtained transcriptomics data.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIGS. 4A-D). (E) CIBERSORT RNA-seq deconvolution results for relative immune cell type abundances between patient tumor samples from k-means clusters (only differentially represented cell types (P<0.05) were selected for presentation/visualization purposes; see Table 1 for absolute cell type abundances). Treatment resistant patients extracted from k-means clusters derived from 32-gene signature expression versus CD8+ T cell activity marker expression for (F) CD8A, (G) CD8B, (H) HLA-A, and (I) PRF1 (P=1.66e-6, P=5.65e-7, P=0.038, and P=5.45e-4, respectively; FIGS. 4F-I). (J) CIBERSORT RNA-seq deconvolution results for relative immune cell type abundances between resistant patient tumor samples from k-means clusters (only differentially represented cell types (P<0.05) were selected for presentation/visualization purposes; see Supp. Table 3 for absolute cell type abundances).

FIGS. 4B-E). (F) CIBERSORT RNA-seq deconvolution results for relative immune cell type abundances between patient tumor samples from k-means clusters (only differentially represented cell types (P<0.05) were selected for presentation/visualization purposes; see Supp. Table 4 for absolute cell type abundances). (G) Overall survival plot/Cox proportional hazard regression analysis results between cluster1 patients (red) and cluster2 patients (green), P=0.00018, HR=0.40[0.49-0.80].

DETAILED DESCRIPTION

Figure 1:
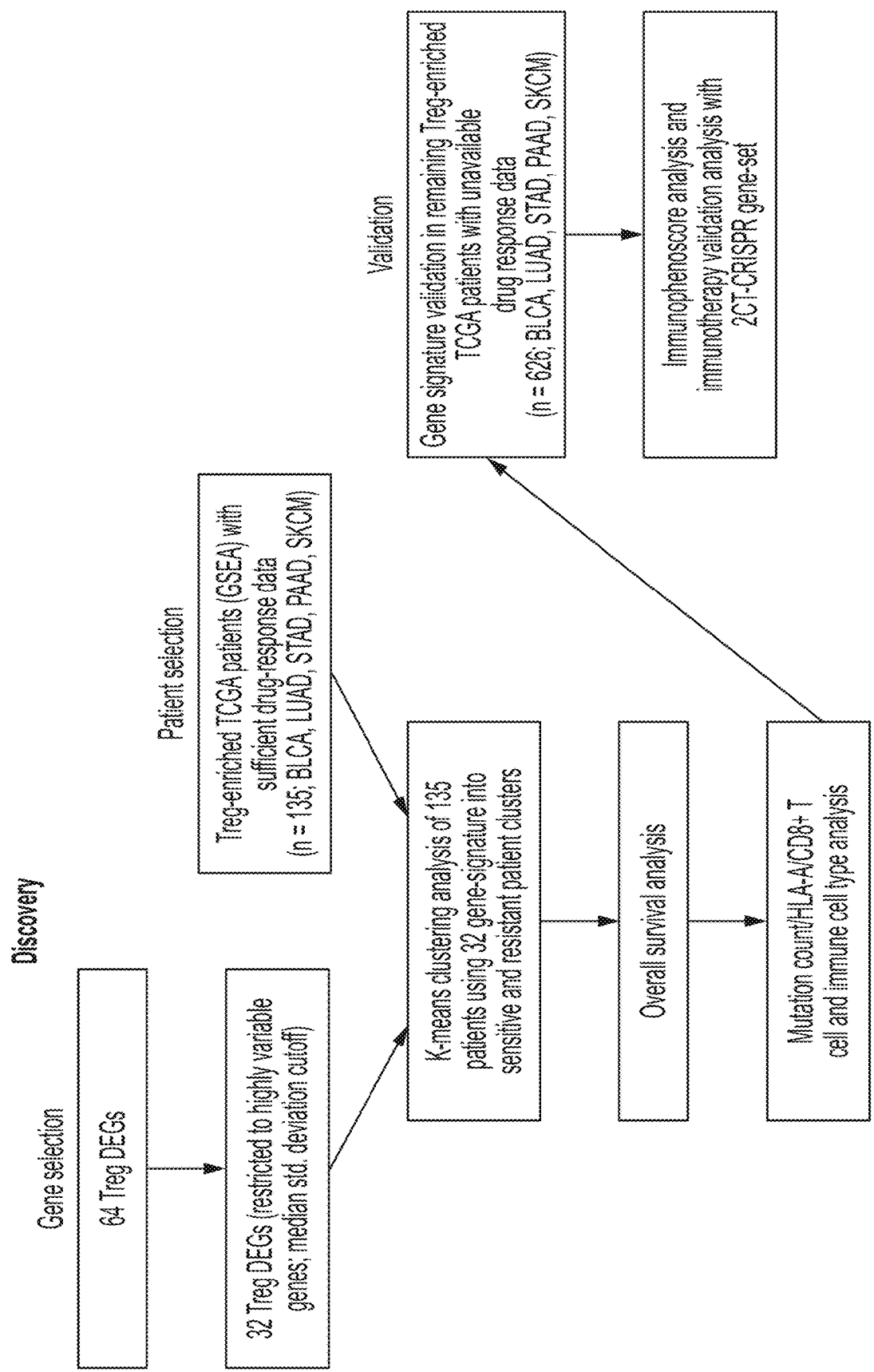
FIG. 1 is an exemplary experimental workflow of 32-gene signature expression analysis in discovery and validation cohorts of Treg-enriched cancer patients.

The inventors have discovered that an omics signature for Treg-enriched tumor samples can be established that has significant predictive and prognostic capacity with respect to tumor immunogenicity, chemosensitivity of the tumor to treatment, and/or overall patient survival.

More specifically, the inventors analyzed RNA-seq (e.g., qualitative and/or quantitative transcriptomics) data of Treg-enriched tumor samples to derive a pan-cancer gene signature in an effort to reconcile the inconsistent results of earlier Treg studies, and to better understand the variable clinical association of Tregs across alternative tumor contexts. As is shown in more detail below, an increased expression of a 32-gene signature in Treg-enriched tumor samples (n=135) was able to distinguish a cohort of patients associated with chemosensitivity and overall survival. This cohort was also enriched for CD8+ T cell abundance, as well as the antitumor M1 macrophage subtype. With a subsequent validation in a larger TCGA pool of Treg-enriched patients (n=626), the results presented herein reveal a gene signature that was able to produce unsupervised clusters of Treg-enriched patients, with one cluster of patients being uniquely representative of an immunogenic tumor microenvironment. Ultimately, these results support a gene signature as a putative biomarker to identify certain Treg-enriched patients with immunogenic tumors that are more likely to be associated with features of favorable clinical outcome.

To that end, the inventors used multiple markers to define Treg enrichment rather than FOXP3 expression alone. However, as opposed to proposing a novel panel of genes to define Tregs, one goal was to examine the global microenvironmental context through which Tregs may be associated with differing clinical outcomes such as chemosensitivity and overall survival (OS), and whether these outcomes would be linked to CD8+ T cell abundance. Therefore, the inventors sought to derive a gene signature that is able to distinguish immunogenic Treg-enriched tumor samples, and hypothesized that a set of highly variable genes differentially expressed by Tregs (amongst 22 immune cell types) would be able to produce distinct patient clusters from a pool of tumor samples that were all selected due to their enrichment for Tregs. Viewed from a different perspective, the inventors implemented a pan-cancer approach (i.e., an approach that uses data across different tumor types) to identify a favorable immunogenic signature based on immunological expression. Thus, it should be noted that the DNA and RNA data in the tumor samples originated from both tumor cells and immune cells within the tumor sample. In the results presented below, a 32-gene signature was established that was able to distinguish a 'hot' tumor phenotype associated with chemosensitivity, OS, and CD8+ T cell activation/abundance amongst a pool of 135 Treg-enriched patient tumor samples. The 32-gene signature was validated by confirming associations with OS, and CD8+ T cell activity/abundance in a larger pool of 626 patients. In addition, the inventors overlapped an independently discovered set of genes believed to be essential for CD8+ T cell function in immunotherapy and assessed the concordance of the clusters produced by each gene set independently.

As can be seen in more detail below, the inventors assessed clinical potential of a 32-gene expression signature to classify patients and their association with chemosensitivity, OS, and CD8+ T cell activation/abundance. As noted above, the genes chosen to comprise this signature were differentially expressed by Tregs and were highly variable across different Treg-enriched tumor samples. The inventors observed that the variation of these genes corresponded to the 'hot' vs 'cold' tumor paradigm, in which a 'hot' tumor with a higher level of tumor infiltrating lymphocytes (TILs) is associated with favorable clinical outcomes. It is worth noting that though all patients in the present results were enriched for Tregs, the tumor gene signature may be also associated with a molecular phenotype of Tregs with diminished suppressive function.

Despite the proportional significance achieved by the number of chemosensitive patients between cluster 1 and cluster 2, there remained 17 chemoresistant patients in cluster 1. To interrogate these patients further, the inventors conducted a series of parallel analyses between these 17 patients and the 46 resistant patients of cluster 2. Strikingly, it was observed that although labeled as chemoresistant, the cluster 1 resistant patients likely possessed 'hotter', more immunogenic tumors, and thus survived longer in terms of overall survival. Specifically, the inventors observed favorable tumor infiltrating lymphocyte expression in these 17 tumor samples from a deconvolution analysis (e.g., CD8+ T cells, less M0 macrophages), as well as augmented CD8+ T cell activation expression (e.g., CD8A/B, PRF1, HLA-A). Together, these clinical parameters agreed with associated patient OS. These results suggest that at least in a small proportion of Treg-enriched patients, the 'heat' of a tumor classified by the 32-gene signature may complement the clinical parameter of chemosensitivity, and that these presumed chemoresistant patients may have been promising candidates for immunotherapy as also extrapolated by IPS blockade scores. Indeed, the inventors contemplate that there may be clinical utility in distinguishing chemoresistance in terms of 'hot' chemoresistance vs 'cold' chemoresistance. It is also interesting to note that while checkpoint marker expression (e.g., PD-1 and CTLA-4) was highly elevated in cluster 1 patients, PD-L1 expression was only marginally elevated (P<3.6e-2, data not shown). This difference in significance between PD-1 and PD-L1 expression can perhaps be explained by the initial Treg-enrichment filtering.

When differential DNA accessibility was examined between cluster 1 patients and cluster 2 patients, a promoter flank site within the TRAF3IP1 gene was predicted to be accessible in almost all cluster 2 patients and inaccessible in almost all cluster 1 patients. TRAF3IP1 is a protein that interacts with TRAF3 and is has been observed to inhibit the innate type I IFN response. TRAF3IP1 was also higher expressed in cluster 2 patients who had lower expression of IFNG and anti-tumor immune activity, suggesting a potential role for TRAF3IP1 regulation in inhibiting the anti-tumor immune response. Additionally, it is worth noting that the greatest visual difference in accessibility was specifically between melanoma patients of cluster 1 and melanoma patients of cluster 2, which is in line with previous work that demonstrated accessibility playing a role in CD8+ T cell immunoreactivity within a melanoma model. Furthermore, recent work in the B16 melanoma model has argued for the rational of coupling HDAC inhibitors to checkpoint blockade therapies to enhance immunotherapy efficacy. This may further propose a clinical relevance for DNA accessibility to be explored in future studies.

While a literature search to biologically explain each gene of the 32-gene signature was not part of the present investigation, one gene of particular interest was Lymphotoxin Beta (LTB), which was elevated in cluster 1 patient tumor samples. Interestingly, LTB has been shown to specifically stimulate Tregs to migrate from the tissue to the lymph nodes via afferent lymphatics. This therefore may at least partly attribute the positive clinical associations of cluster 1 patients to elevated LTB expression, which may be directing immunosuppressive Tregs away from tumor tissue sites, thus unleashing the antitumor response within cluster 1 tumor samples.

To obtain sufficient sample sizes, the inventors used a pan-cancer approach to interrogate differences between the clusters produced by the unsupervised k-means method. The inventors confirmed that neither cluster was enriched for any single cancer type, which may have otherwise surfaced the tumor tissue type as a confounding variable. The inventors additionally pursued an extensive analysis to de-convolute the heterogeneity of the tumor, showing that CD8+ T cell activity was likely enriched in cluster 1 patient tumor samples and that chemosensitivity was perhaps complemented by the immunocompetence of the 'hot' tumors. Moreover, in line with the results for each cancer type included in the pan-cancer population, the inventors observed CD8+ T cell tumor abundance to be associated with favorable patient prognosis. Of note, the pro-inflammatory IFNγ, which is a marker of CD8+ T cell mediated tumor regression and TIL abundance, was significantly elevated in cluster 1 samples. It is also worth mentioning that although all patient tumor samples examined were enriched for Treg expression, cluster 1 possessed a higher mean CD8+ T cell to Treg ratio (data not shown). This result, which is based on the expression of the 32-gene signature, is also in line with previous clinical findings pertaining to the tumor microenvironment. Furthermore, the inventors observed that FOXP3 expression was significantly elevated in the clinically favorable cluster of patient tumor samples (cluster 1, $P<5.41e-14$; data not shown), which is also in accord with previous FOXP3 related studies.

While the inventors specifically interrogated CD8+ T cell abundance/activation markers, the inventors also observed differential activation of tumor associated macrophages (TAMs), with cluster 1 patients enriched for M1 macrophage abundance. The M1 subtype, which is associated with higher levels of IL-1, TNFa, IL-12, and CXCL12, is associated with the inflammatory, anti-tumor response. This observation was therefore in line with previous work, suggesting a complementary interaction between M1 macrophages and CD8+ T cells to ameliorate pro-tumorigenic activity within cluster 1 patient tumor samples. Cluster 2 accordingly possessed a higher abundance of M0 macrophages, potentially suggesting a larger undifferentiated premature pool of monocytes in these patients as opposed to those of cluster 1. A pathway network activation analysis from a more holistic perspective also revealed a shift towards activated TCR signaling and the inflammatory response in cluster 1 patients but not in cluster 2 patients. Together, it was observed that the 32-gene feature set was able to distinguish a chemosensitive cohort (cluster 1) with higher antitumor immune activity, perhaps in part via the previously proposed interplay between TAMs and CD8+ T cells. It is also interesting to note that the cluster 2 patient pool (which was enriched for chemoresistance) uniquely possessed upregulated pathway activation for DNA damage response and nucleotide metabolism ($P<0.037$ and $P<0.026$, respectively). In agreement with previous work, these molecular processes have been observed to play a role in chemoresistance and survival likely by ameliorating the intended damage of chemotherapeutic compounds.

It should be noted that the 32-gene signature is specific is to Treg-enriched patient tumor samples as determined by the previously described GSEA methods, and that the small number of Treg-enriched patients with sufficient drug response data was limited (n=135) and thus prevented establishing a robust aggregate cutoff to examine in a held-out validation dataset. To partially address this, however, the inventors used an unsupervised clustering method which rendered the clusters independent of clinical variables (e.g., tumor stage, lymph node status, age), and it was shown that the clusters were in good concordance with clusters derived from an independently proposed set of genes important for CD8+ T cell function. Unexpectedly, the chemosensitivity analysis was not specific to a certain drug, but rather to response to treatment for BLCA, LUAD, PAAD, SKCM, and STAD patients. This mixed set allowed corroboration of the paradigm of a 'hot' tumor across five tumor types and to propose an immunogenic gene expression signature independent of clinical variables.

Therefore, it should be appreciated that the data presented herein support a clinically robust 32-gene signature able to distinguish patients with a favorable phenotype, at least in part through CD8+ T cell activity and abundance. Through a pan-cancer analysis of Treg-enriched patient tumor samples, it can be shown that two opposing contexts in which Tregs may be associated with alternative clinical features. Indeed, the inventors' study marks the first pan-cancer patient study of its kind to interrogate tumor transcriptomic data to help reconcile the growing controversy of Tregs and their clinical impact. Moreover, the inventors believe the proposed gene signature may also serve to extrapolate disease-specific gene signatures that could further sculpt the landscape of tumor immune biology.

Experiments

The following is an exemplary illustration of the inventive subject matter and should not be construed as limiting the invention. The person of ordinary skill in the art will readily be able to use alternative or equivalent data, samples, materials, and processes, and al of such variations are contemplated herein.

Methods:

Patient Selection and Drug Response Data

The inventors used curated records of drug treatments and outcomes generated from TCGA clinical data to label chemosensitivity. Patients with 'Complete Response' or 'Partial Response' in this curated dataset were assigned to a 'sens' label, while patients with 'Stable Disease' or 'Clinical Progressive disease were assigned to a 'res' label. Chemosensitivity served as one parameter to assess clustering output significance (further discussed below).

RNAseq data (TOIL RSEM norm_count) was downloaded and used as input features for unsupervised clustering was from the TCGA Pan-Cancer cohort from xenabrowser.net (dataset ID: tcga_RSEM_Hugo_norm_count, unit: log 2(norm_count+1), hub: GA4GH (TOIL) hub). This dataset contained 10,535 tumor samples, but only those with available drug response data enriched for Tregs were examined. The inventors executed the filtering for Treg-enriched tumor samples via The Cancer Immunome Database (tcia.at) using gene set enrichment analysis (GSEA) of a non-overlapping, pan-cancer derived set of genes representative for Treg enrichment (FOXP3, CCL3L1, CD72, CLEC5A, ITGA4, L1CAM, LIPA, LRP1, LRRC42, MARCO, MMP12, MNDA, MRC1, MS4A6A, PELO, PLEK, PRSS23, PTGIR, ST8SIA4, STAB1). This method has been previously described and clinically validated in further detail. For a TCGA cohort to be included in the analysis, it was required to comprise samples that were (1) enriched for Tregs (q<0.05), and (2) have sufficient clinical drug response data (at least 15 samples with available drug response labels in each cohort). Coalescing and applying these two filters yielded 135 total patients for analysis across 5 TCGA cohorts (18 BLCA, 37 LUAD, 33 PAAD, 24 SKCM, 23 STAD). This yielded a sufficient population for a pan-cancer unsupervised gene-signature expression analysis (n=135).

Gene Signature Selection and Patient Clustering

K-means clustering was used as a vector quantization method to classify the 135 patient tumor samples (k=2) via the ComplexHeatmap package in R using the Treg differentially expressed genes (DEGs) previously produced. However, instead of using all 64 Treg DEGs available, the inventors used only the highly variable 32 genes as a feature gene set (outlier(s) removed and median standard deviation cutoff of 64 genes expressions within the 135 patient tumor samples). This 32-gene set served as the feature set used for k-means clustering (the expression of each gene was scaled to the z-score relative to expression of that gene across the 135 tumor samples). As assumed by the unsupervised classification process, drug response labels were not included as input features, and nor were cancer types. Together, the input dataset included a table with 135 rows (TCGA patient IDs) and 32 columns (32 highly-variable Treg DEGs) of z-score scaled expression values.

Proportional cluster significance for patient drug response sensitivity enrichment was determined using the "N−1" Chi-squared test (DF=1, $P<0.05$ was considered significant). To eliminate the possibility of cancer-type serving as a confounding variable, and thus ensuring that cohorts analyzed were not unevenly representative of a certain cancer type, a Chi-squared test of independence in a contingency table was performed using the scipy.stats module in Python ($P<0.05$ was considered significant).

Survival Analysis

Overall survival (OS) data for the 135 patients was downloaded from OncoLnc (oncolnc.org). Survival datasets for the BLCA, LUAD, PAAD, SKCM, and STAD cohorts were parsed and Kaplan-Meier plots were generated in Python. Log-rank tests were conducted using the Lifelines implementation in Python (lifelines 0.11.1) (1 month was considered 30 days; $P<0.05$ was considered significant).

Genomic Transcriptomic Analysis

Patient genomic mutations and transcriptomic expression values were accessed using the fbget Python API and parsed in Python (URL.confluence.broadinstitute.org/display/GDAC/fbget). Mutations were retrieved via whole-exome-sequencing MAF data, and gene expression values were retrieved as log 2-normalized values via RSEM. The Mann-Whitney test was performed to compare mutation counts between patient clusters/cohorts. Two-tailed t-tests were used to determine significantly differential expression of CD8A, CD8B, and HLA-A between cohorts. For both mutation count and differential gene expression, $P<0.05$ was considered significant. Mutation histograms and expression swarm-boxplots were generated in Python using the Matplotlib and Seaborn libraries.

Immune-Cell Type Abundance

To characterize immune cell composition within the 135 patient tumor samples, the inventors used CIBERSORT to present cell-type abundance via RNA transcript expression from a recommended gene expression profile of 547 genes for 22 immune cell types. The recommended model parameters were used for this prediction task (e.g., LM22 signature gene file, disabled quantile normalization for RNA-seq data), and 1,000 permutations were conducted. In short, this strategy applies nu-support vector regression (v-SVR) to discover a hyperplane that separates classes of interest. CIBERSORT has been shown to outperform other approaches and has been previously described in further detail.

For upregulated pathway network analysis, the integrated software workflow AltAnalyze was used to analyze expression data in the context of interaction networks and pathways. The input data included whole-transcriptome data from each patient (with 3,325 tissue-specific genes from TissGDB filtered out) obtained from TOIL RSEM data and encoded as log 2(TPM+1) with no other normalizations. Enriched/upregulated pathways (from WikiPathways) were those with at least a 2.0-fold-change surfaced from the integrated GO-Elite software that retained significance ($P<0.05$) after Benjamini-Hochberg Fisher's exact P-value adjustment.

DNA Accessibility Analysis

DNA accessibility predictions across whole genomes for TCGA patients of interest were generated using a convolutional neural network model that has recently been shown to make accurate predictions at promoter and promoter flank sites, even for novel biotypes not seen in training. The model makes binary accessibility predictions for 600-base-pair DNA sequences centered at potentially accessible sites, as identified through agglomerative clustering. Model input includes the DNA sequence of a specific site augmented with an input vector of select gene expression levels estimated from RNA-seq. This additional RNA-seq vector is what makes it possible for the neural network to learn to modulate accessibility predictions appropriately according to the cellular context and make predictions for unseen cell types.

Gene expression levels for patient samples were obtained from TOIL RSEM data and encoded as log 2(TPM+1) with no other normalizations. Since whole genome sequencing was not available for all patients of interest, all predictions were made using the reference genome hg19/GRCh37. It is therefore possible that some differences between patients were missed due to this lack of mutation information. Empirically it was found that including mutation information affected the classification outcome at 5.5% of promoter and promoter flank sites.

The model was trained to make predictions at 1.71 million genomic sites, with a training set consisting of 338.7 million training examples, spanning 66 unique cell and tissue types from ENCODE. Of the 1.71 million training sites, the TCGA predictions were restricted to 108970 sites that overlapped with promoter and promoter flank annotations. A classification threshold was selected such that the neural net achieved 80% precision on those sites when making predictions for novel biotypes, at which it demonstrated a recall of 65.3% and false positive rate of 10%. For analysis only the subset of those promoter and promoter flank sites that overlapped with protein coding genes (as annotated by GENCODE v19 and extended by 1k base pairs front the TSS) were considered, reducing the number of regions to 86057.

Immunophenoscore and Immunotherapy Gene Analysis

An immunophenoscore (IPS) can be derived in an unbiased manner using machine learning by considering the four major categories of genes that determine immunogenicity (effector cells, immunosuppressive cells, MHC molecules, and immunomodulators) by the gene expression of the cell types these comprise (activated CD4+ T cells, activated CD8+ T cells, effector memory CD4+ T cells, Tregs, MDSCs). The IPS is calculated on a 0-10 scale based on representative cell type gene expression z-scores, where higher scores are associated with increased immunogenicity. This is because the IPS is positively weighted for stimulatory factors (e.g., CD8+ T cell gene expression) and negatively weighted for inhibitory factors (e.g., MDSC gene expression). Finally, the IPS is calculated based on a 0-10 scale relative to the sum of the weighted averaged z-scores. A z-score of 3 or more translates to an IPS of 10, while a z-scores 0 or less translates to an IPS of 0, demonstrating a higher IPS is representative of a more immunogenic tumor. This method has been described in further detail with the immunogenic determinant categories, as well as corresponding cell types and gene sets, which can be found at tcia.at.

The inventors retrieved patient IPSs from The Cancer Immunome Atlas framework. Relative bar plots were generated for visualization and error bars reflect standard deviations. Two-tailed t-tests were used to determine significantly differential IPS values (P<0.05 was considered significant).

The 19 genes used to reinforce the 32-gene signature derived clusters were taken from a previous study that used a 2CT-CRISPR assay system to identify 554 candidate genes essential for immunotherapy. Via hierarchical clustering, the gene set we examined were those of the 554 genes that identified to be correlated with cytolytic activity across most TCGA cancer types. To measure concordance, the inventors calculated Cohen's kappa via a concordance table of clusters predicted from k-means with our 32-gene set and the Patel 18-gene set. A Cohen's kappa value of 0.61-0.80 constitutes a 'good' quality of agreement.

The heatmap representative of the relative expressions of the 12/18 genes significantly elevated in cluster 1 patients (acceptable P<0.003) was produced with the ComplexHeatmap package in R. Clusters represented are those derived from our initial 32-gene k-means clustering. The inventors used this gene set as validation to show that the 32-gene signature used for clustering was able to produce a cluster with high expression of the same genes recently identified as likely essential for immunotherapy in an independent setting.

Results

Figure 2:
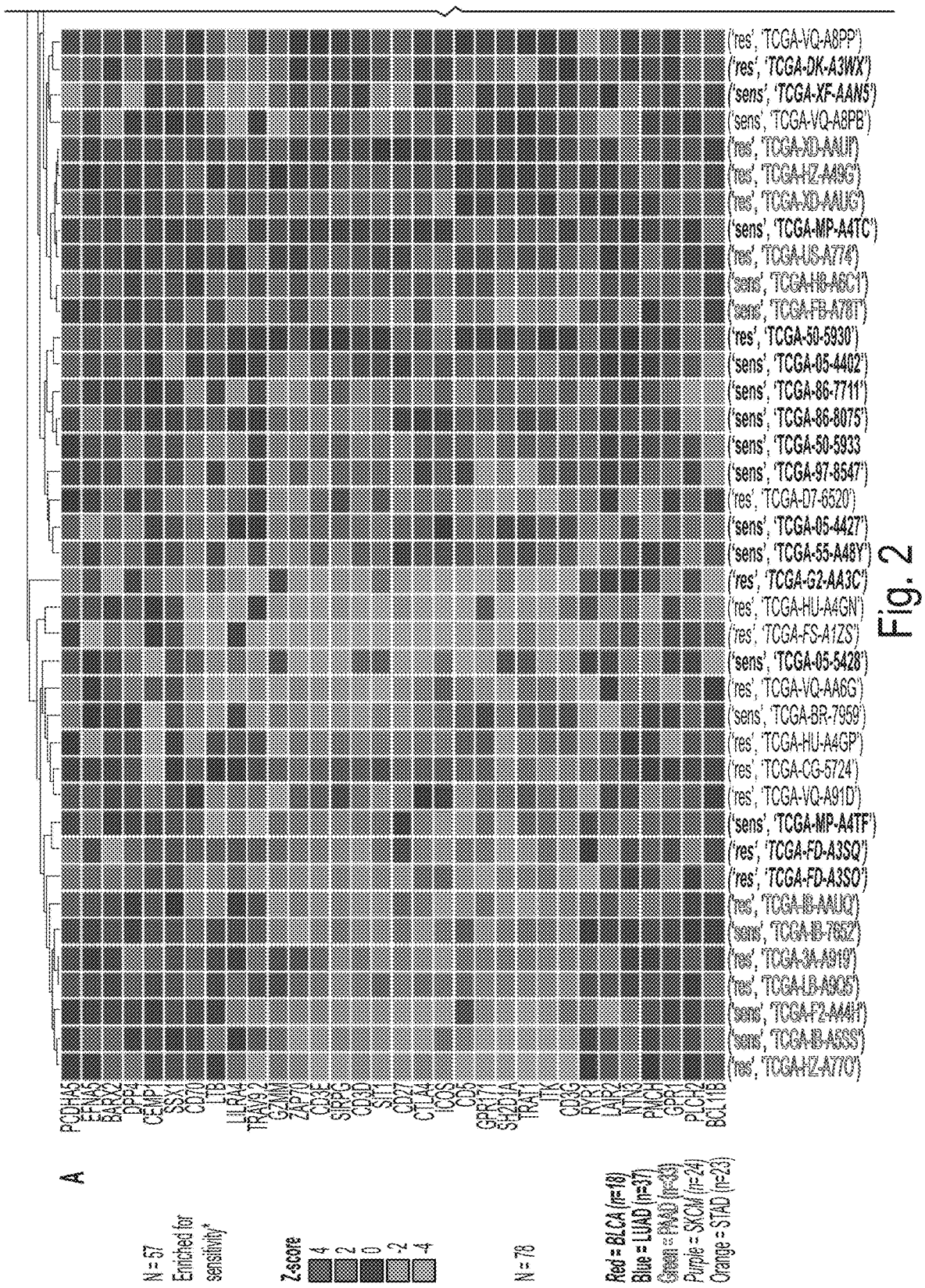
FIG. 2 depicts unsupervised k-means clusters of Treg-enriched cancer patients from patient gene expressions of 32-gene signature in the discovery cohort (n=135). (A) Clusters obtained from k-means clustering analysis (k=2), with cluster1 (n=57, high/red) enriched for treatment sensitivity (P=0.0007, $x^2$=11.58) compared to cluster2 (n=78, low/green), and neither cluster confounded with tumor anatomical location (P>0.05; see Supp. Table 1-2). Row labels correspond to sensitivity marker ('sens'=Partial Response or Complete Response, 'res'=Stable Disease or Clinical Progressive Disease) and TCGA patient barcodes. Row label colors correspond to TCGA cancer type (18 BLCA [red], 37 LUAD [blue], 33 PAAD [green], 24 SKCM [purple], 23 STAD [orange]). (B) k-means clusters produced from 32-gene signature in SKCM (P=0.0450, $x^2$=4.022). (C) k-means clusters produced from 32-gene signature in STAD (P=0.0007, $x^2$=11.53). (D) k-means clusters produced from 32-gene signature in LUAD (P=0.6137, $x^2$=0.225). (E) k-means clusters produced from 32-gene signature in PAAD (P=0.9478, $x^2$=0.004). (F) k-means clusters produced from 32-gene signature in BLCA (P=0.0652, $x^2$=3.400).
Figure 2:
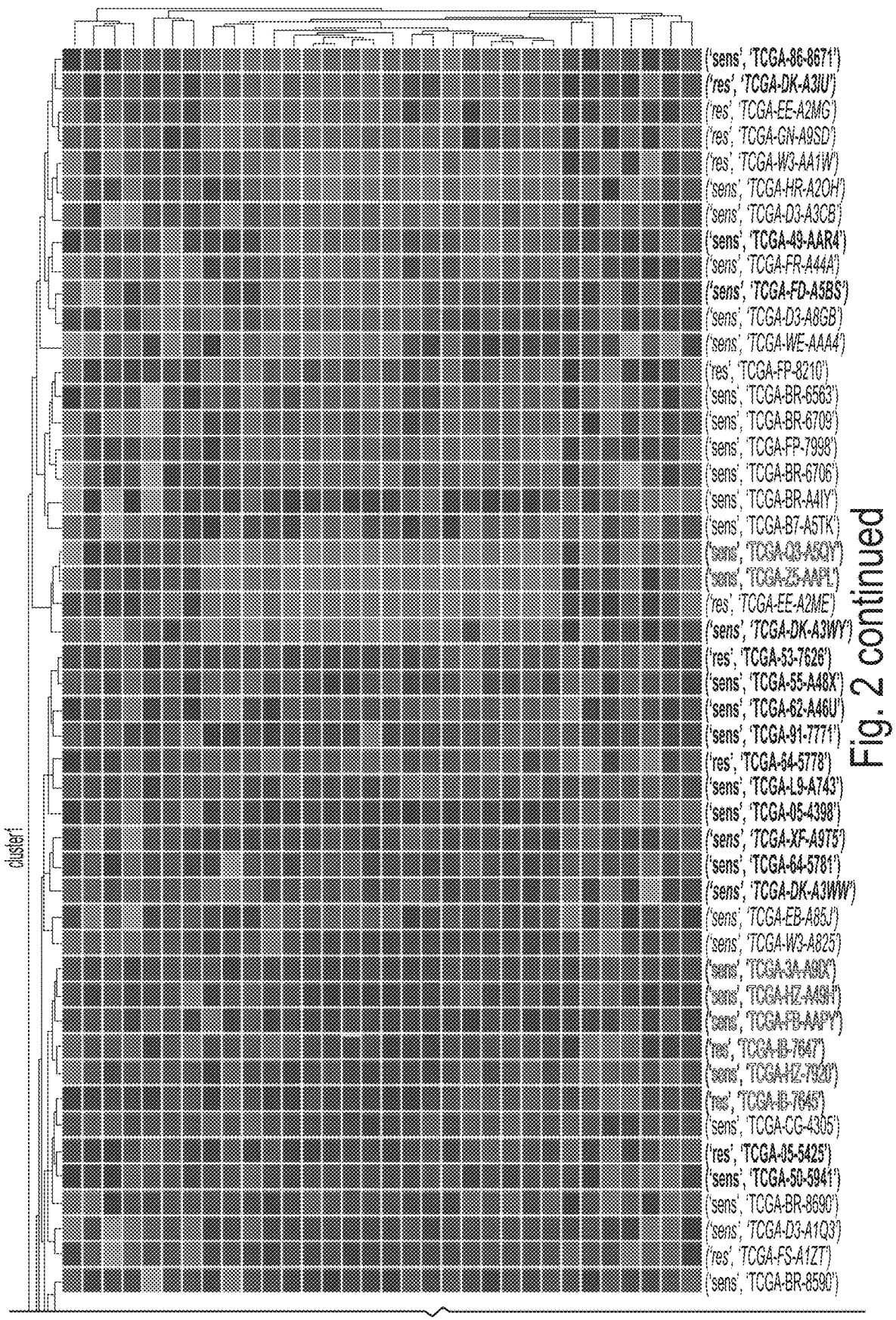
Figure 2:
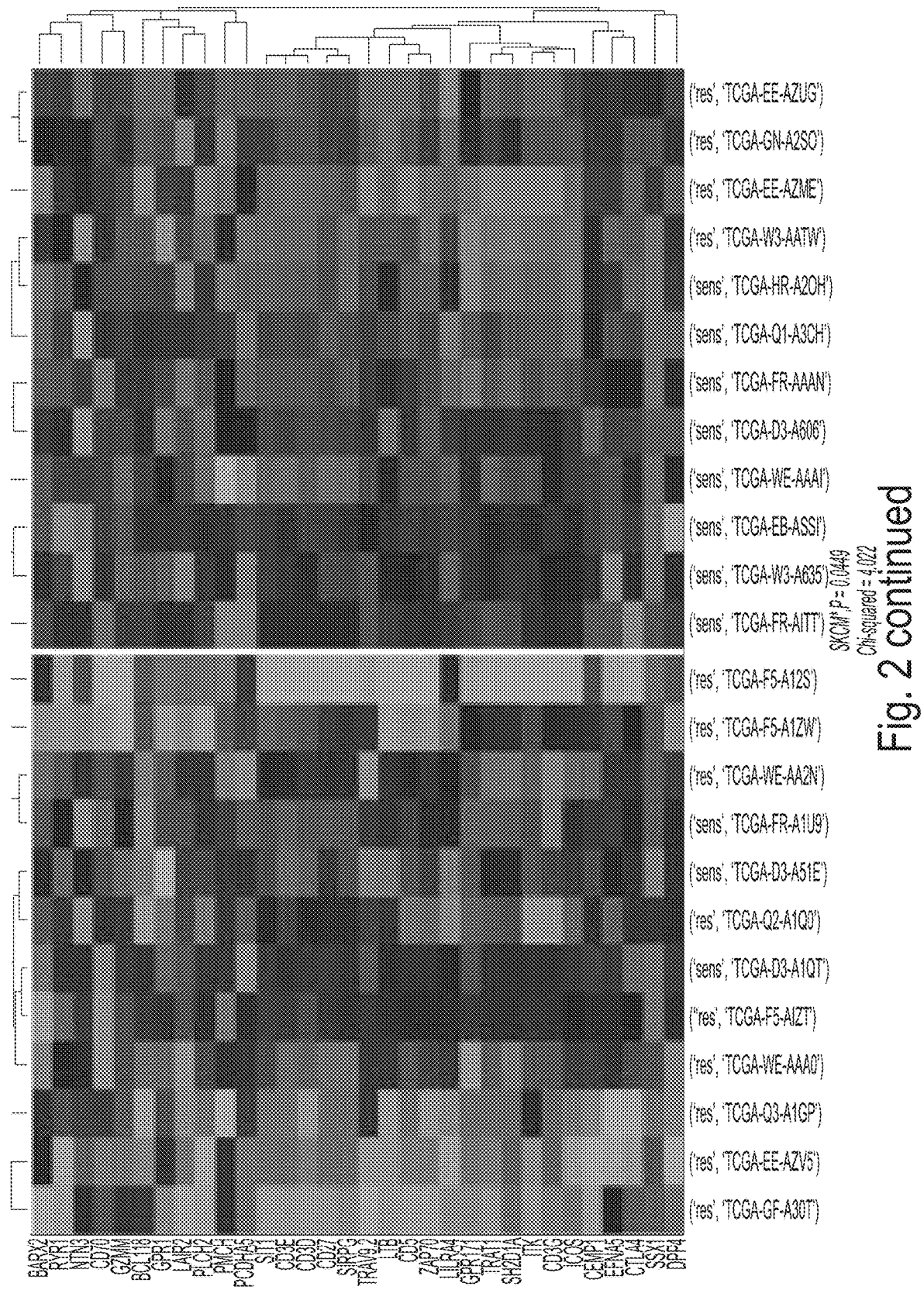
Figure 2:
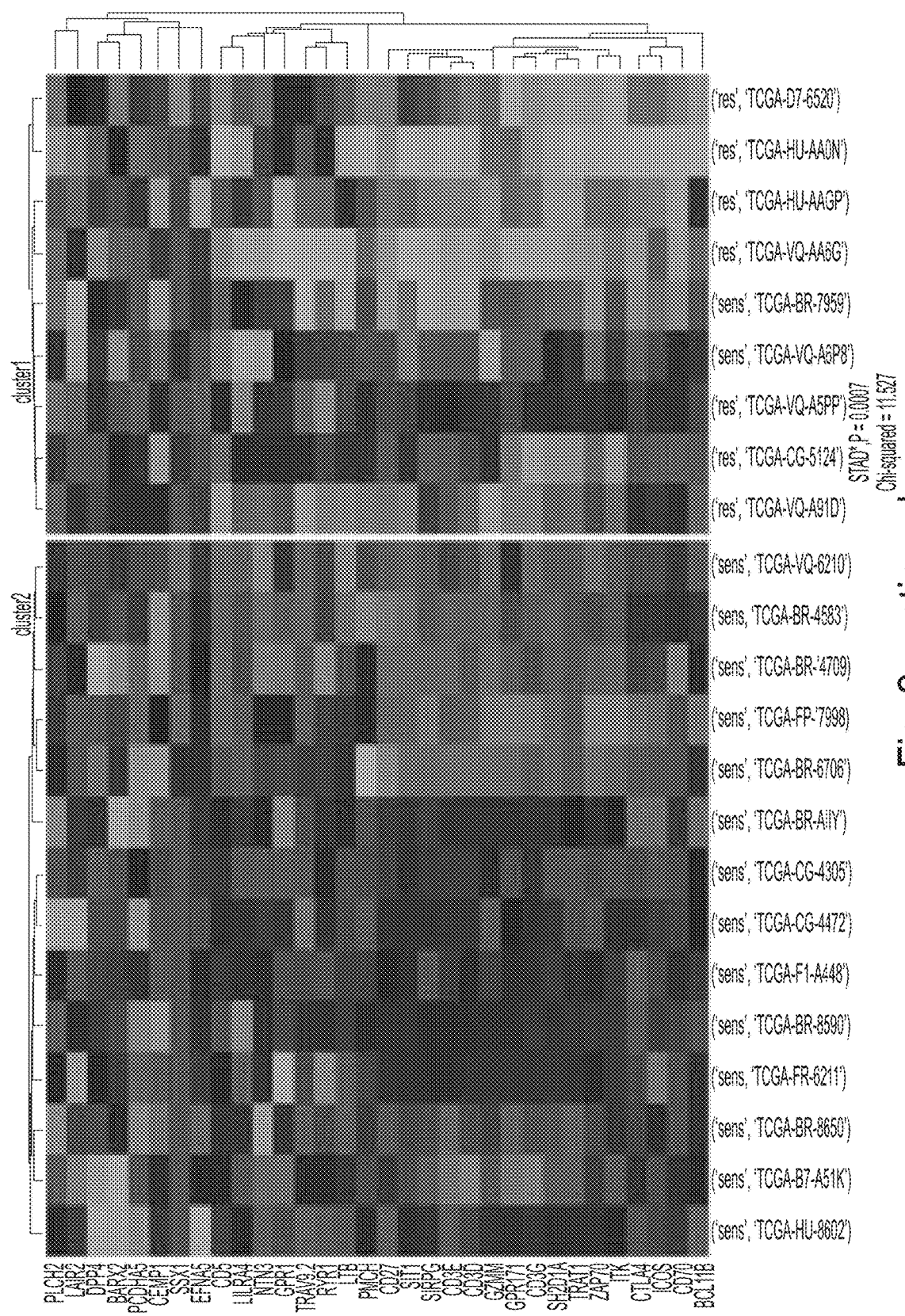
Figure 2:
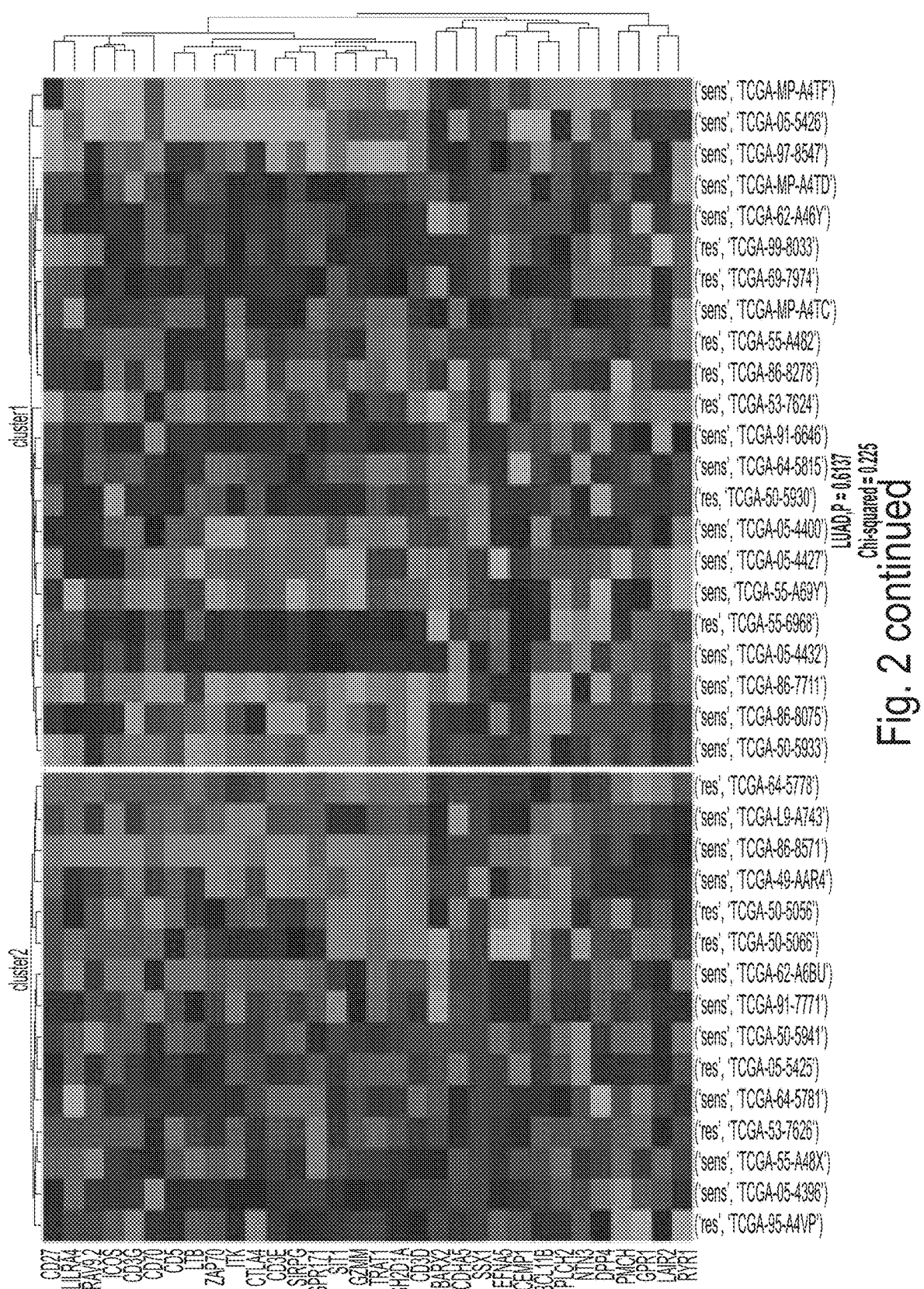

Unsupervised clustering using the 32 Treg DEGs: A typical experimental workflow is shown in FIG. 1. Patient tumor samples analyzed in the current study were restricted to those that were (1) Treg-enriched (q<0.05) and (2) possessed sufficient clinical drug response labels (nTotal=135) (FIG. 1). Using only the 32 highly variable genes differentially expressed by Tregs, k-means clustering was able to produce two distinct clusters of patient tumor samples (P=0.0007, $x2=11.58$; FIG. 2, Panel A). Cluster 1 (n=57) was enriched for chemosensitivity (70.17% of patients were sensitive to drugs prescribed), while cluster 2 (n=78) was enriched for chemoresistance (only 40.74% were clinically sensitive to drugs prescribed).

Overall, patient cancer type was not associated with cluster (P>0.05, $x2=7.69$; Table 1 below). Nevertheless, when the 32-gene signature was used to cluster patients of each cancer type individually, clusters enriched for sensitivity to treatment were observed in both SKCM and STAD (P=0.0450, $x2=4.022$ and P=0.0007, $x2=11.53$; FIG. 2, Panels B-C). Proportional significance was not observed when identical clustering methods were applied independently to LUAD, PAAD, and BLCA (P=0.614, P=0.948, and P=0.065, respectively; FIG. 2, Panels D-F).

Figure 3:
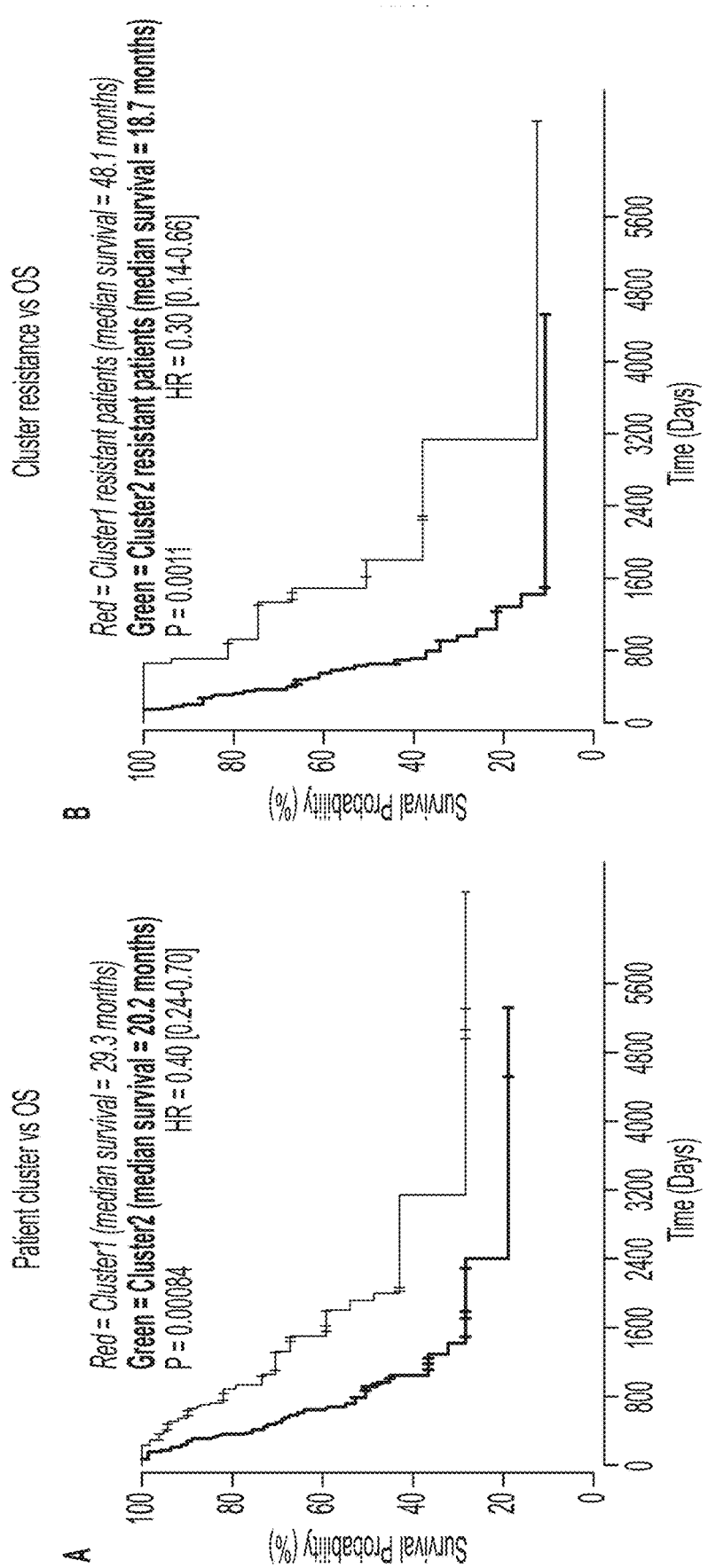
FIG. 3 depicts overall survival plots/Cox proportional hazard regression analysis results. (A) OS analysis between cluster1 patients (n=57, red) and cluster2 patients (n=78, green), P=0.00084, HR=0.40[0.24-0.70]. (B) OS analysis between resistant patients from cluster1 (n=17, red) and resistant patients from cluster2 (n=45, green), P=0.0011, HR=0.30[0.14-0.66].

Cluster 1 patients are associated with favorable overall survival: To determine whether the cluster 1 enrichment for drug-sensitivity was reflected in survival, overall survival (OS) survival analysis was performed and results are shown in FIG. 3. Cluster 1 OS was observed to be 29.4 months, while cluster 2 OS was observed shorter at 21.0 months, demonstrating an 8.4-month median survival difference. As hypothesized, cluster 1 was significantly associated with patient OS in comparison to cluster 2 (P=0.00084, HR=0.40 [0.24-0.70]; FIG. 3, Panel A).

While cluster 1 was enriched for patients who were sensitive to treatment, there was a handful of 'resistant' patients that were of further interest in this cluster (n=17). To examine these patients further, the inventors hypothesized that despite clinical labels for initial drug-response, patient OS would be significantly longer for an immunologically active 'hotter' tumor than it would be for a less immunologically active 'colder' tumor. Therefore, we sought to determine whether 'resistant' patients in cluster 1 differed in OS as compared to the 'resistant' patients of cluster 2 (n=45). After confirming that neither resistant patient cohort was enriched for a certain cancer type, the inventors analyzed patient OS between each resistant cohort. Strikingly, the median survival duration of the resistant patients in cluster1 was more than twice that of the resistant patients in cluster 2 (49.0 months vs 18.7 months, P=0.0011, HR=0.30 [0.14-0.66]; FIG. 3, Panel B).

CD8+ T-cell activity/abundance is enriched in cluster 1 patient tumor samples: To examine a putative explanation that may corroborate the observed clinical outcome parameters for the 32-gene signature (e.g., chemosensitivity and OS), the inventors examined the distributions of mutation count per cluster and CD8+ T-cell biomarker expression, as mutation count and CD8/HLA-A expression have previously been observed in association with drug response and survival via neoantigen production and cytotoxic lymphocyte activation, respectively. To this end, and in line with this previous work, neither total mutation count nor non-synonymous mutation count was associated with cluster 1. However, CD8A/B, HLA-A, and PRF1 expressions were significantly elevated in patient tumor samples from cluster 1 (P=2.24e-19, P=2.14e-18, P=1.16e-4, and P=2.42e-10, respectively; see FIG. 4A, Panels A-D).

Figure 4A:
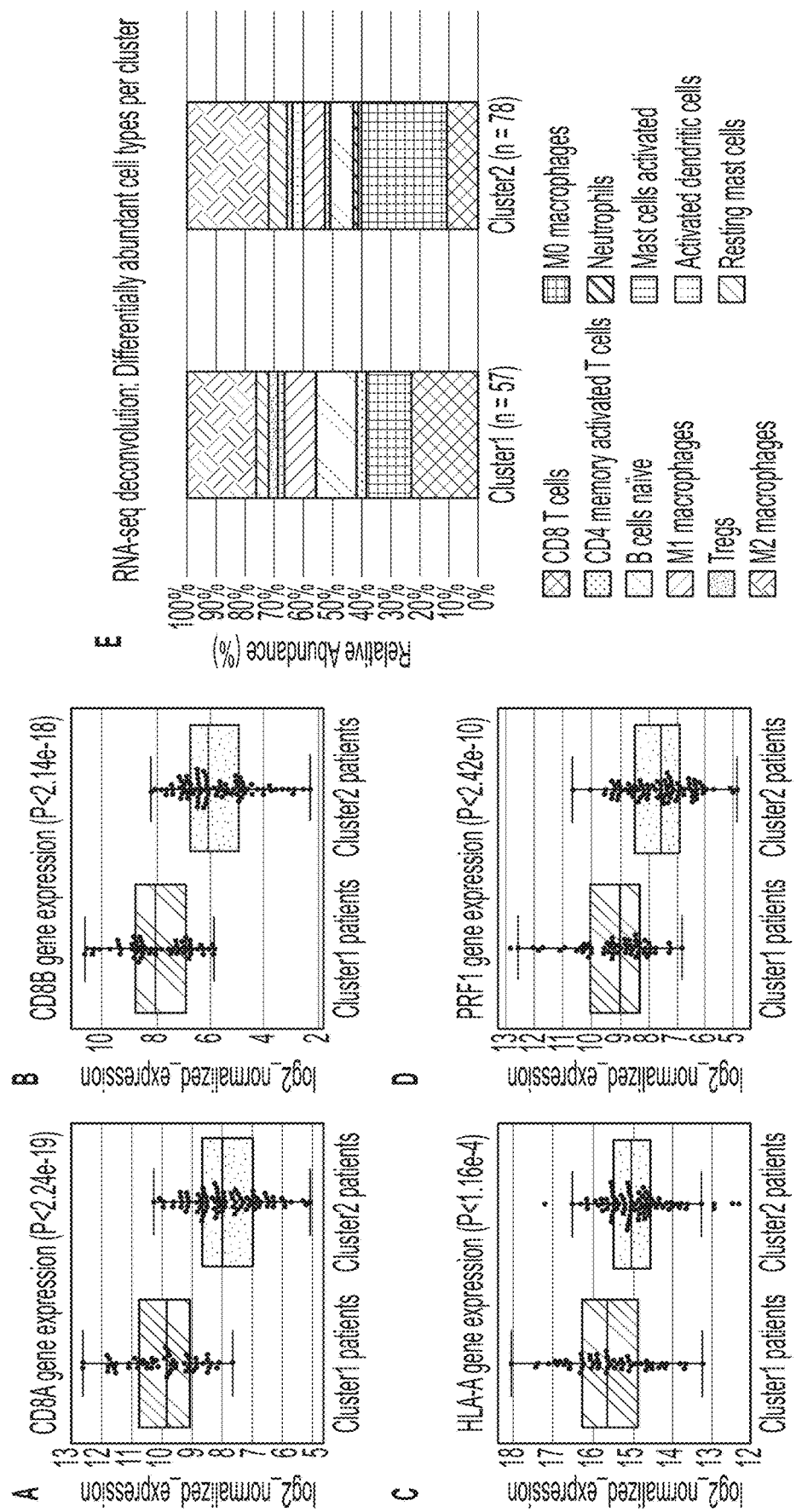
FIGS. 4A and 4B depict CD8+ T cell activity and immune cell abundance analysis between clusters. K-means clusters derived from 32-gene signature expression versus CD8+ T cell activity marker expression for (A) CD8A, (B) CD8B, (C) HLA-A, and (D) PRF1 (P=2.24e-19, P=2.14e-18, P=1.16e-4, and P=2.42e-10, respectively.

In order to suggest with further confidence at the level of immune cell type that CD8+ T-cells were more abundant in tumor samples from cluster1 patients, the inventors applied a gene expression deconvolution framework to interpret the immunologically heterogeneous RNA-seq signals of each patient tumor sample. In line with the observations of elevated CD8A/B gene expression in cluster 1, CD8+ T-cells mean abundance was significantly higher in cluster 1 patient tumor samples than that of cluster 2 (15.3% vs 7.4% of total immune cells, P=1.00e-7; FIG. 4A, Panel E and Table 1 that indicates RNA-seq tumor sample deconvolution to immune cell type abundances (absolute value means) between clusters derived from 32-gene signature).

TABLE 1

| Immune Cell Type | cluster1 mean abundances (n = 57) | cluster2 mean abundances (n = 78) | t-statistic | P-value |
| --- | --- | --- | --- | --- |
| T cells CD8 | 0.153530 | 0.073861 | 5.270214 | 0.000001 |
| Macrophages M0 | 0.108029 | 0.199764 | −4.258066 | 0.000038 |
| T cells CD4 memory activated | 0.021997 | 0.006819 | 4.209816 | 0.000069 |
| Neutrophils | 0.001244 | 0.010078 | −3.231105 | 0.001772 |
| Macrophages M1 | 0.072440 | 0.048957 | 2.745808 | 0.007010 |
| B cells naive | 0.103911 | 0.059839 | 2.372021 | 0.019814 |
| Mast cells activated | 0.001338 | 0.009605 | −2.288763 | 0.024394 |
| Dendritic cells activated | 0.014635 | 0.027883 | −2.245423 | 0.026440 |
| T cells regulatory (Tregs) | 0.020736 | 0.011808 | 2.249714 | 0.026875 |

TABLE 1-continued

| Immune Cell Type | cluster1 mean abundances (n = 57) | cluster2 mean abundances (n = 78) | t-statistic | P-value |
|---|---|---|---|---|
| Macrophages M2 | 0.157614 | 0.192663 | −2.125468 | 0.035405 |
| Mast cells resting | 0.030808 | 0.044771 | −2.089000 | 0.038608 |
| NK cells activated | 0.006706 | 0.011616 | −1.460647 | 0.146820 |
| T cells follicular helper | 0.045859 | 0.036308 | 1.400419 | 0.163802 |
| T cells CD4 naive | 0.007653 | 0.000103 | 1.341638 | 0.185125 |
| Monocytes | 0.026926 | 0.038978 | −1.303338 | 0.195072 |
| Plasma cells | 0.038825 | 0.050363 | −1.160674 | 0.247865 |
| B cells memory | 0.038502 | 0.023567 | 1.160351 | 0.248782 |
| Dendritic cells resting | 0.005879 | 0.009324 | −1.080562 | 0.281837 |
| NK cells resting | 0.034977 | 0.033187 | 0.325962 | 0.745004 |
| T cells CD4 memory resting | 0.152862 | 0.149396 | 0.207072 | 0.836325 |
| Eosinophils | 0.000260 | 0.000223 | 0.159053 | 0.873866 |

Figure 4B:
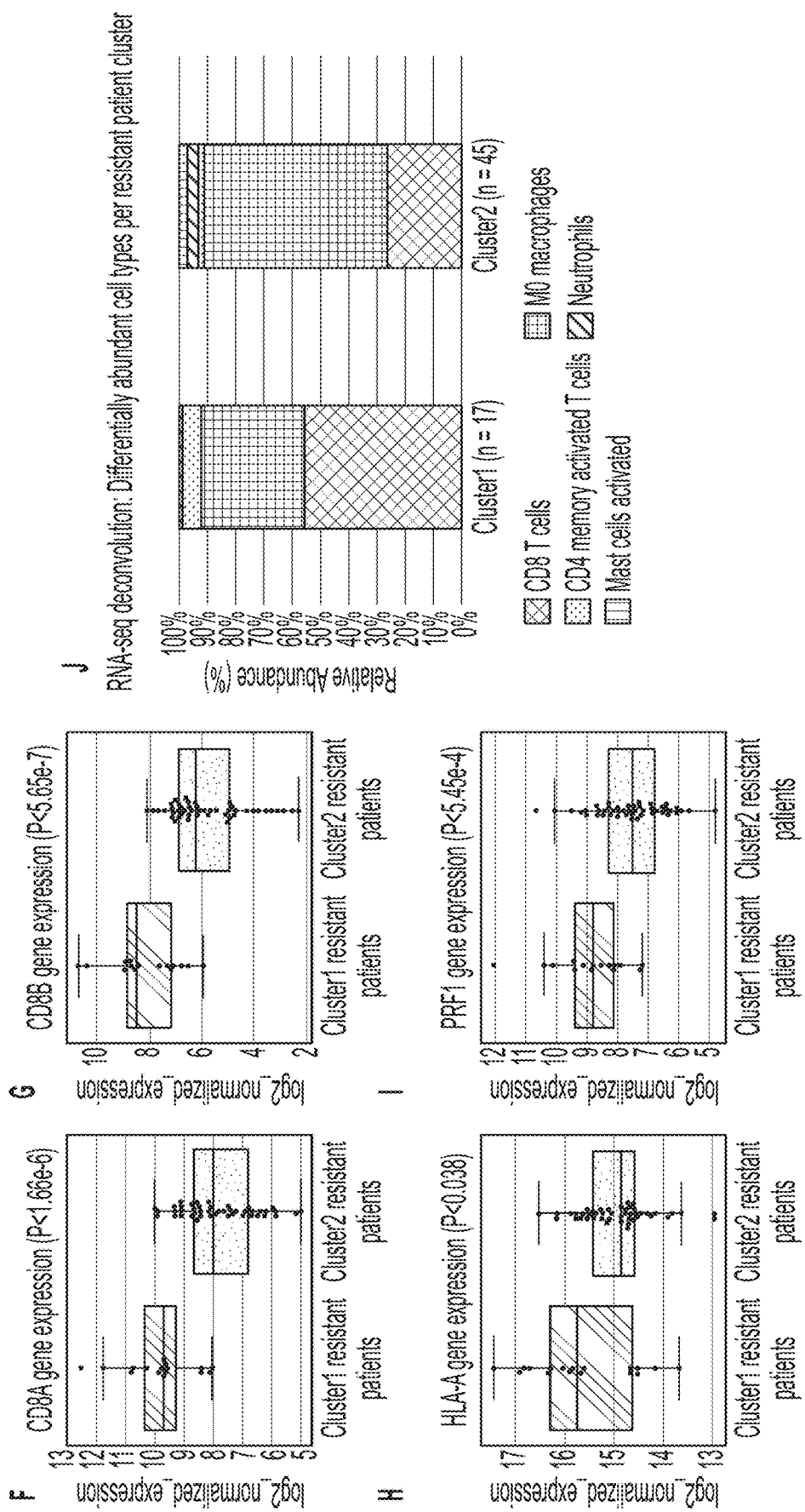

In parallel, continuing the analysis of cluster 1 chemoresistant patients vs cluster 2 chemoresistant patients, we examined mutation counts and expression of CD8A/B and HLA-A, as well as immune cell type abundances between these two resistant patient sub-cohorts. Similar to the previous broader cluster analysis, mutation count was not associated with chemoresistant patient cohort. Moreover, in line with the OS observations of these patients, CD8A/B, HLA-A, and PRF1 expressions were higher in resistant patient tumor samples from cluster 1 than for those from cluster 2 (P=9.0e-6, P=2.0e-6, P=0.038, and P=0.0008 respectively; FIG. 4B, Panels F-I). Furthermore, in resistant patients, CD8+ T-cells mean abundance was higher in cluster1 resistant patient tumor samples than that of cluster2 resistant patients (14.5% vs 7.6%, P=0.013; FIG. 4B, Panel J).

Patient tumor sample DNA accessibility analysis: DNA accessibility refers to whether a certain region of DNA is accessible to regulatory molecules and proteins such as transcription factors, and recent work has revealed the importance of investigating the accessibility of regulatory regions during immune events such as CD8 T cell exhaustion, as accessible regions possess high potential to be expressed and or accessed by transcriptional machinery that may influence an immune response. In line with this and due to the inherently high dimensional data of chromatin organization, deep learning models have been trained on DNase-seq and recently extended to incorporate RNA-seq data to predict accessibility in a variety of cell types and tumor samples. The inventors therefore sought to explore whether cluster 1 patients and cluster 2 patients may differ in DNA site accessibility predictions across 86,057 promoter and promoter flank sites across the human genome. Interestingly, the inventors observed sites within 14 genes that were predicted to be enriched for accessibility in cluster 2 patients.

Of particular interest, the inventors observed a site within TRAF3IP1 to be the most differentially accessible site of all 86,057 sites between clusters. TRAF3IP1 has been shown to negatively regulate the innate Type 1 IFN response, and indeed, TRAF3IP1 expression was elevated in cluster 2 patients. Conversely, when investigating the pro-inflammatory immune marker IFNG, the inventors observed significant gene expression elevation in cluster 1 patients. These results suggest that TRAF3IP1 may be an unfavorable biomarker perhaps related to the anti-tumor immune response at least in Treg-enriched patient tumor samples.

Gene signature analysis in validation cohort: To confirm that the application of this gene signature was not unique to the initial subset of patients selected, and that it extends to all Treg-enriched patients from the cohorts studied, the inventors applied the 32-gene signature to the remaining Treg-enriched patients. As will be readily appreciated, Treg enrichment can be ascertained in numerous manners, including immunohistochemical analysis and expression analysis of genes specifically or preferentially expressed in Tregs. For analytical consistency, these patients were those of the same cancer types (BLCA, LUAD, PAAD, SKCM, STAD) that were Treg-enriched (q<0.05). However, these patients did not have available drug response data to assess treatment sensitivity.

Figure 5A:
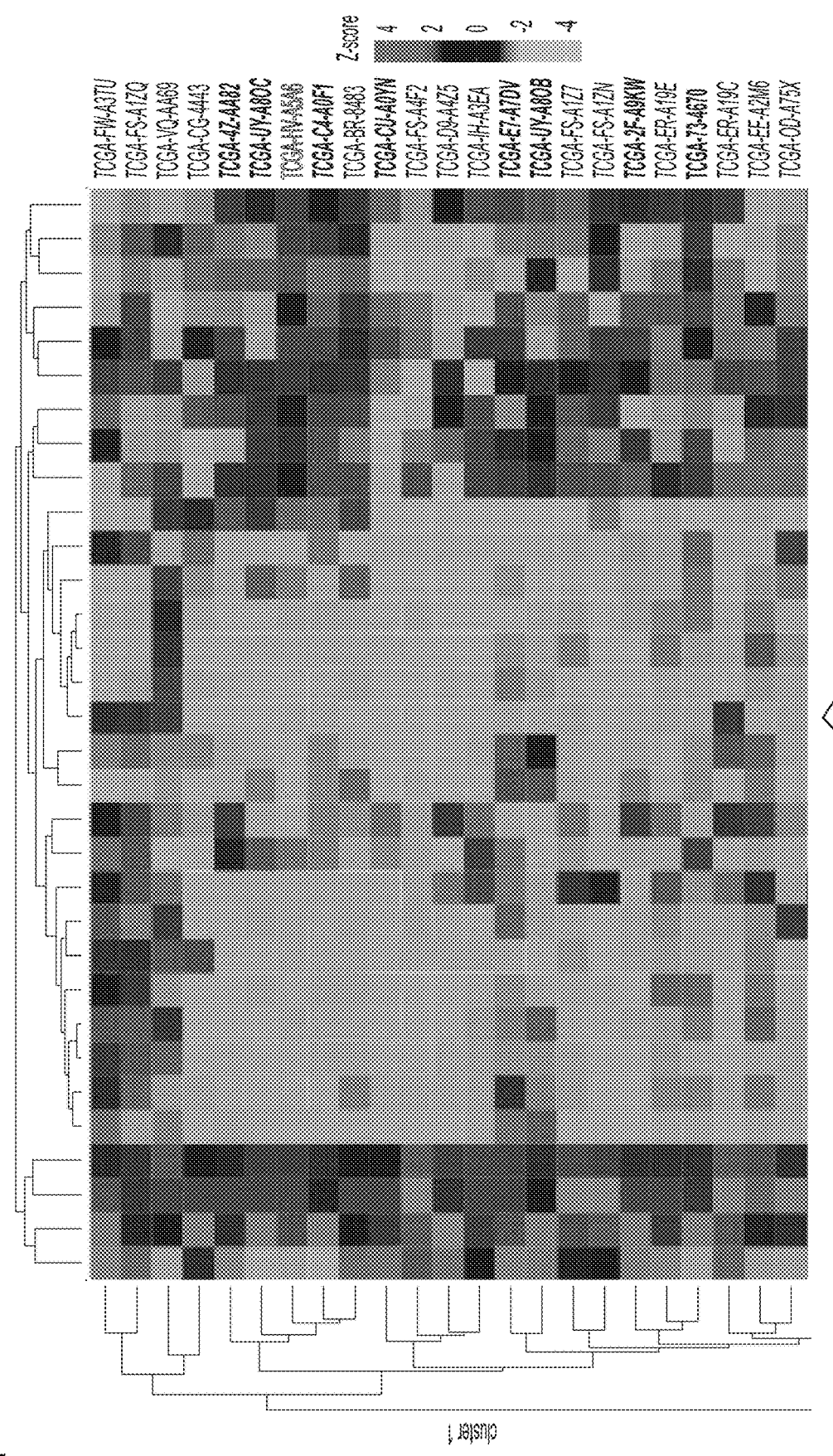
FIGS. 5A and 5B depict gene signature analysis in TCGA validation dataset (n=626). (A) 32-gene signature expression k-means clustering produces two clusters ($n_{cluster1}$=332, $n_{cluster2}$=294). Clusters derived from 32-gene signature expression in TCGA validation data versus CD8+ T cell activity marker expression for (B) CD8A, (C) CD8B, (D) HLA-A, and (E) PRF1 (P=4.19e-79, P=1.59e-69, P=2.96e-17, and P=5.20e-58, respectively.
Figure 5A:
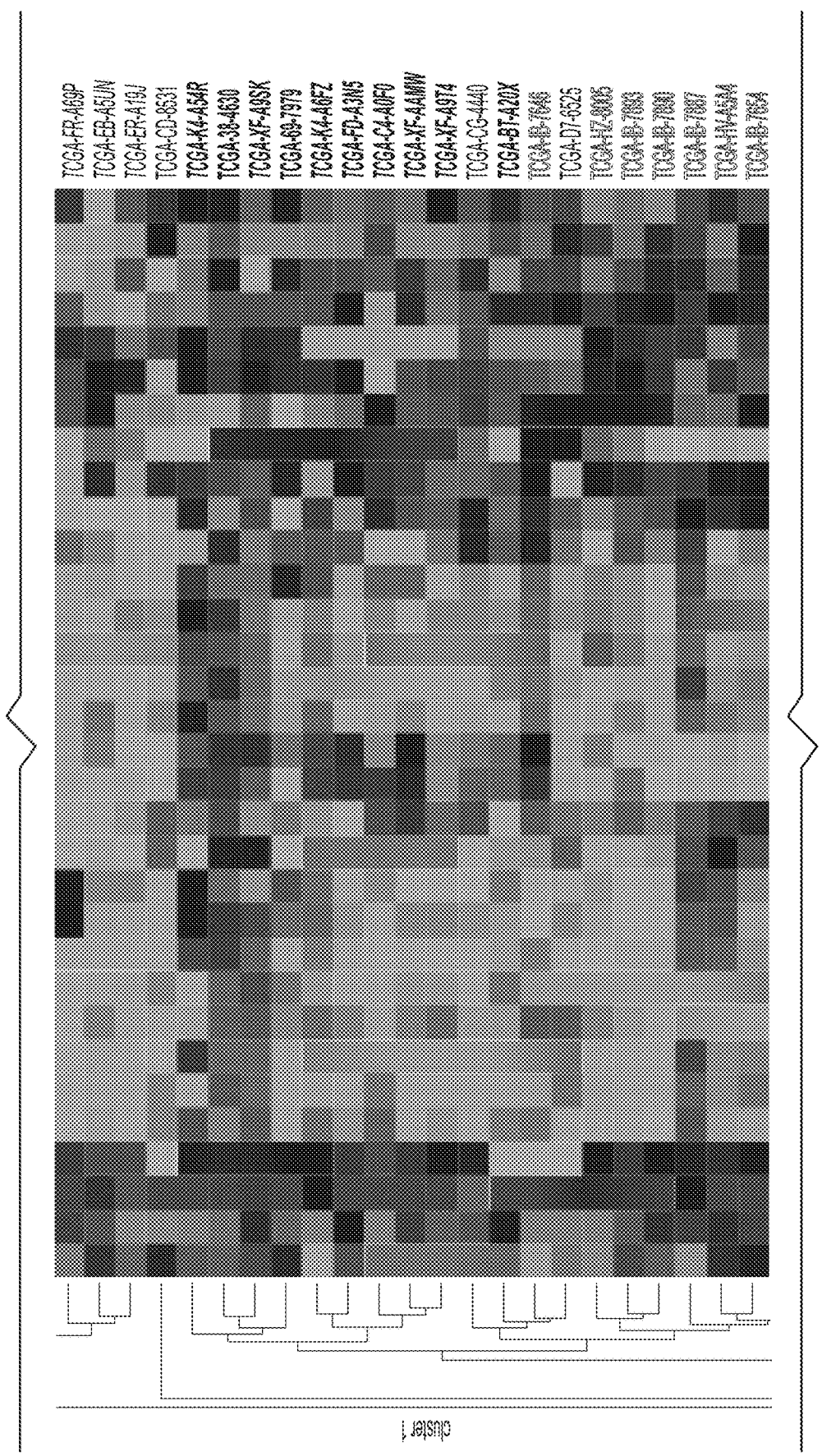
Figure 5A:
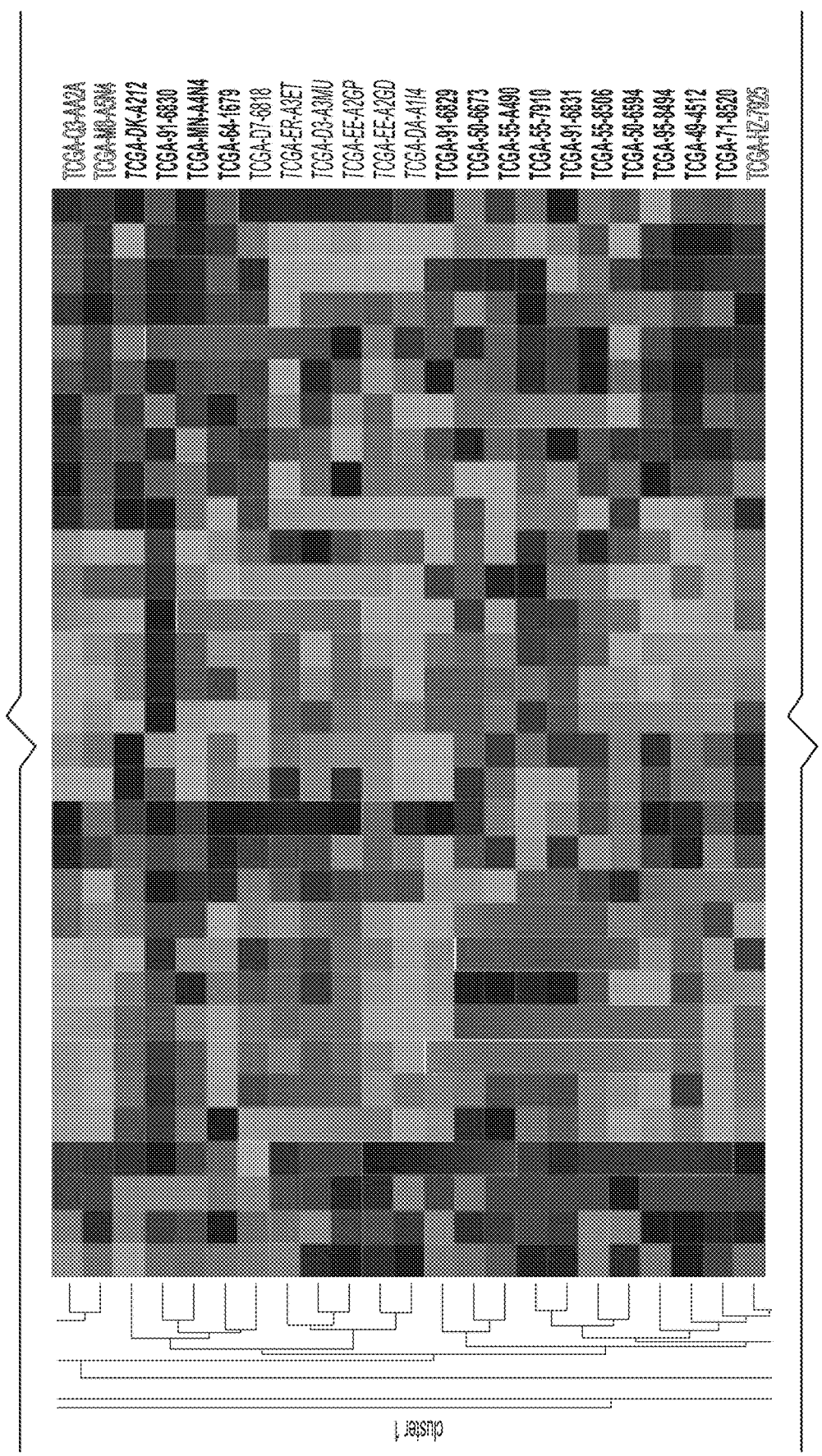
Figure 5A:
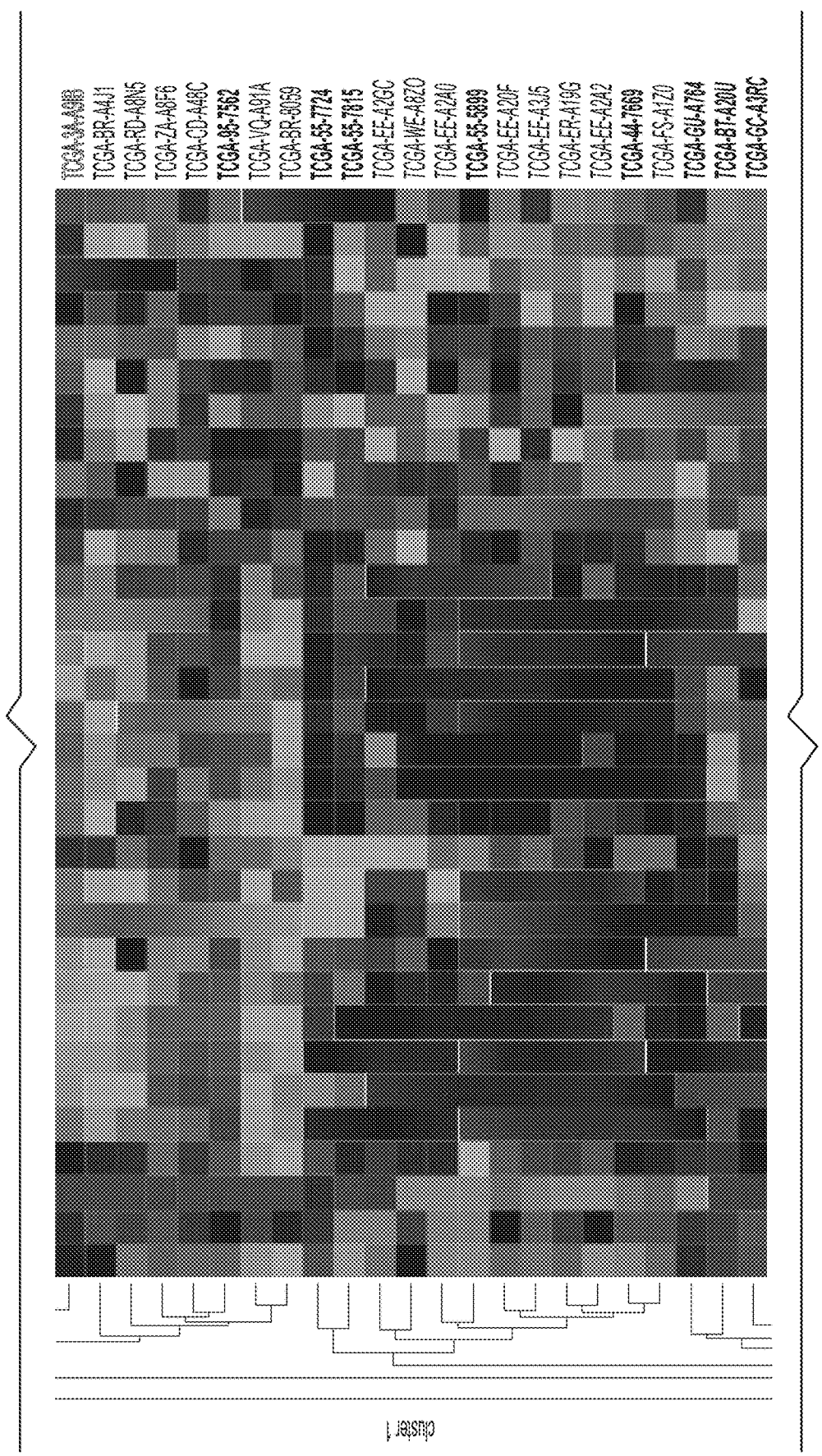
Figure 5A:
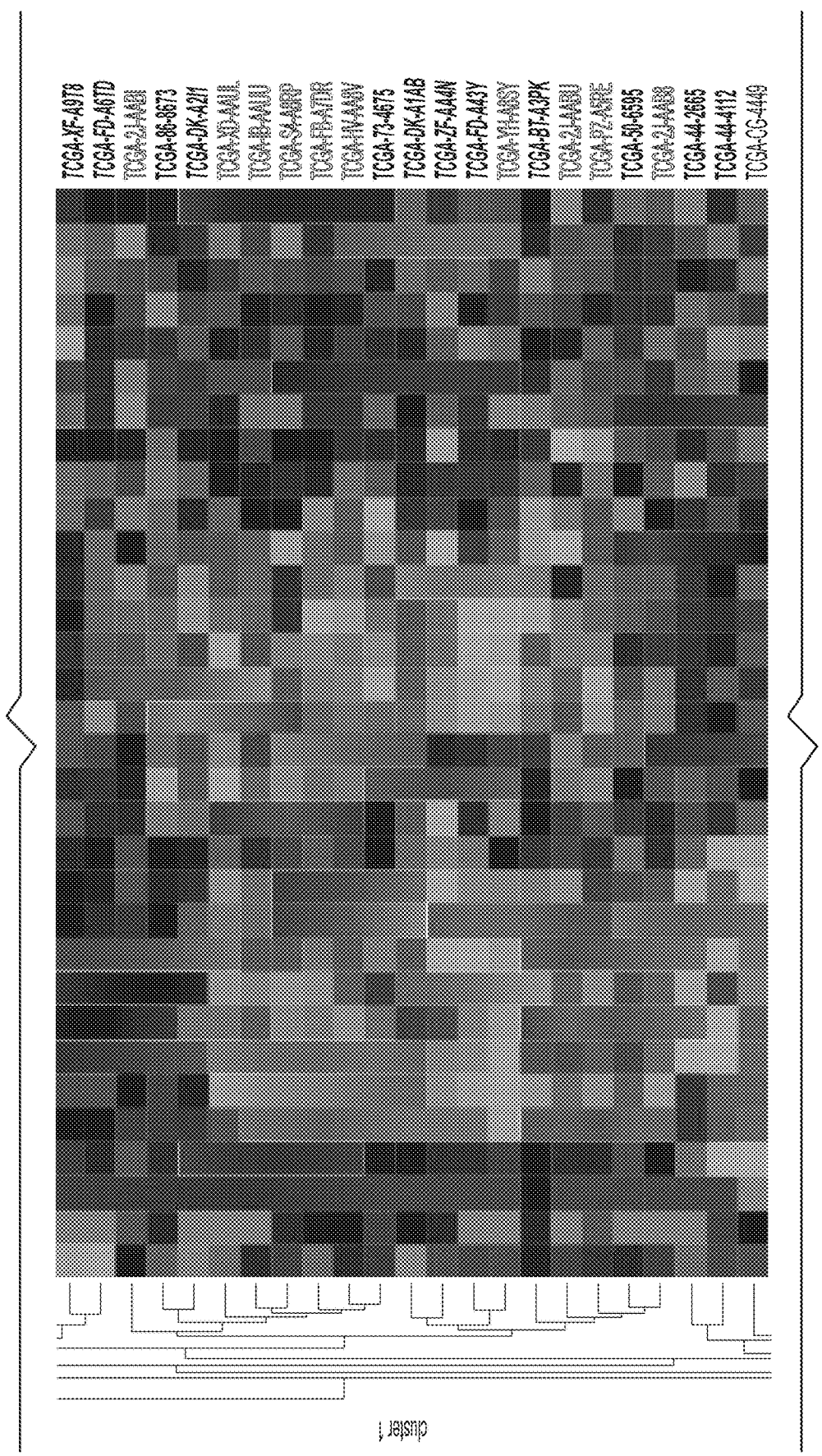
Figure 5A:
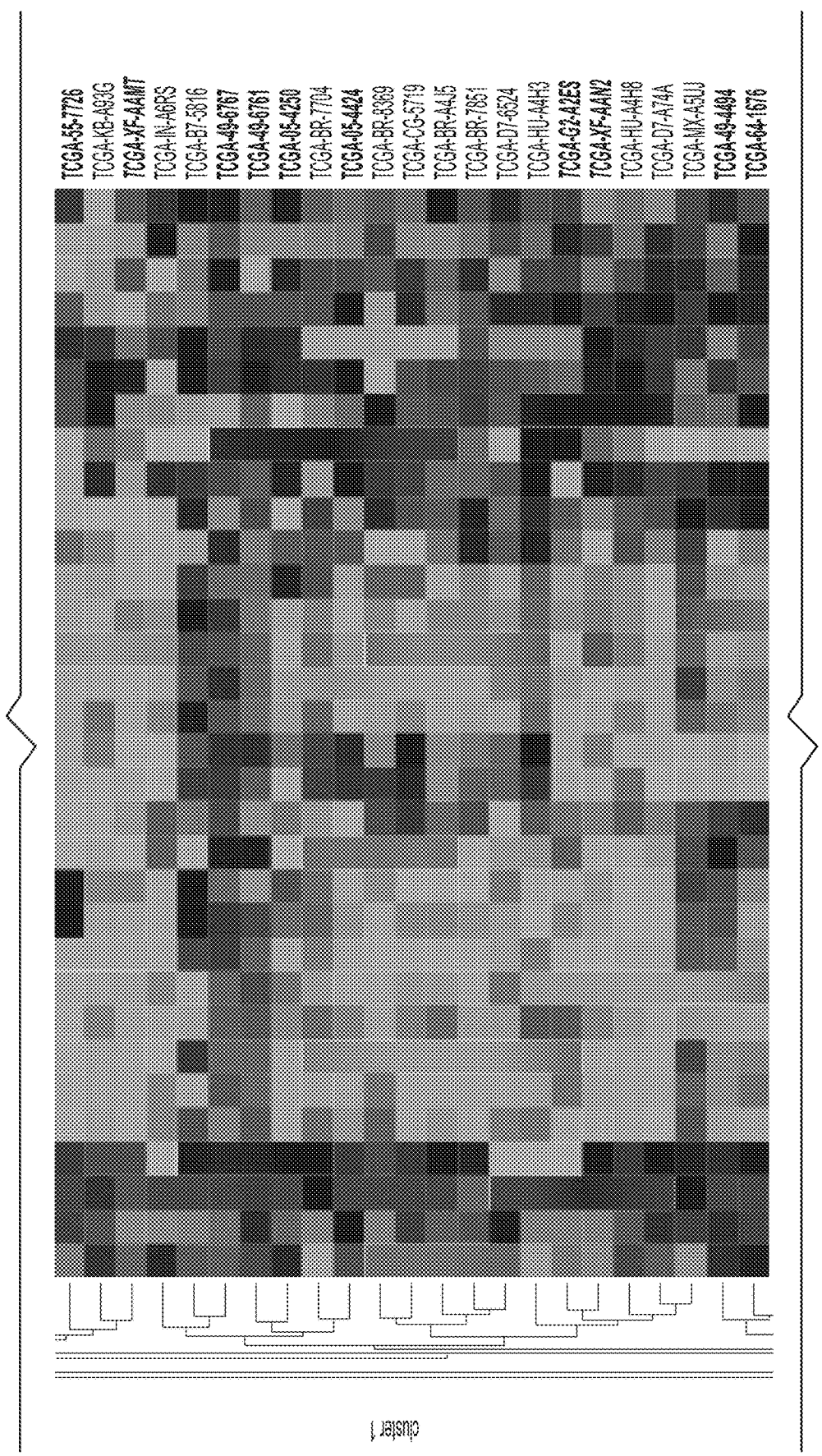
Figure 5A:
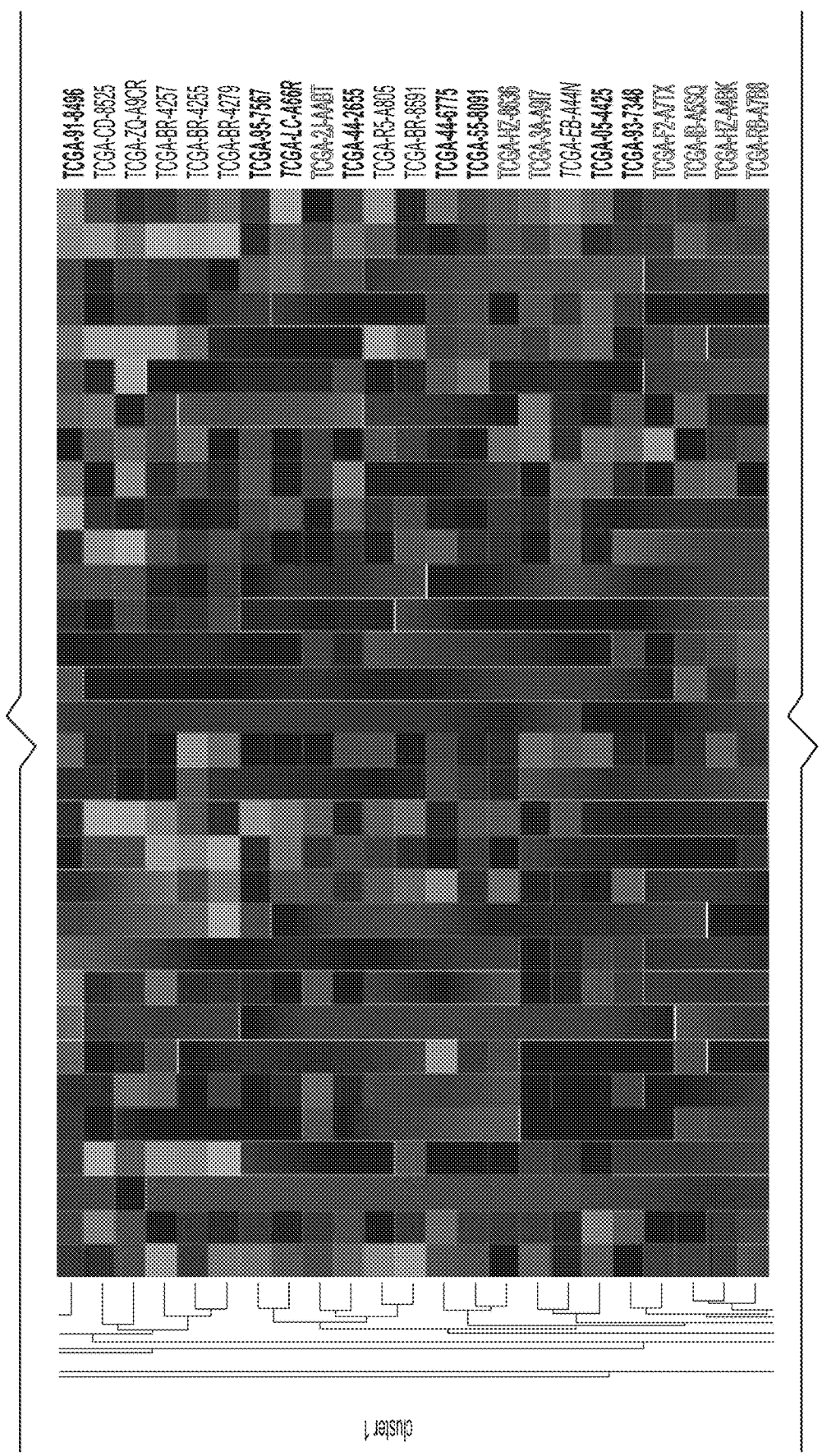
Figure 5A:
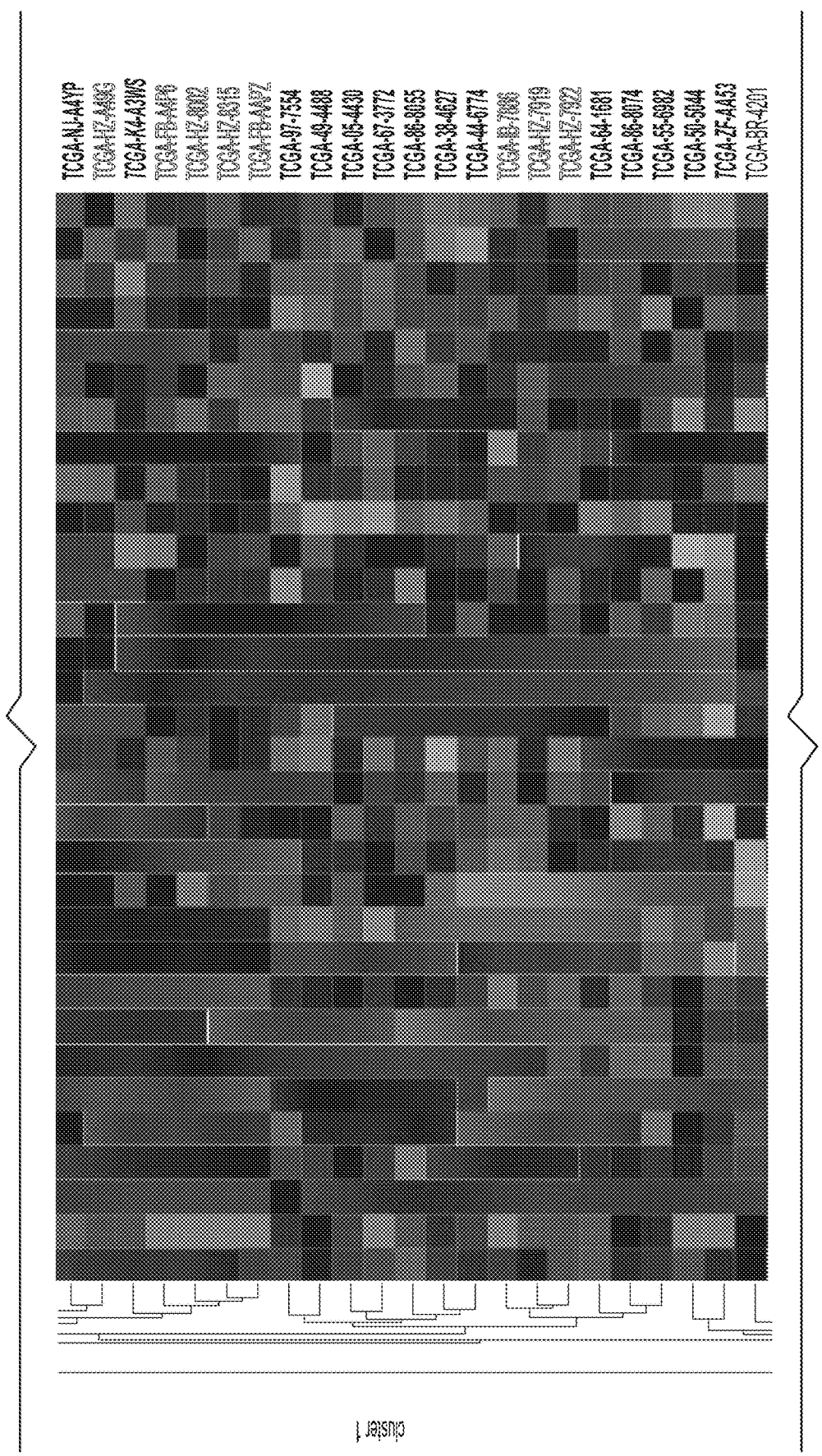
Figure 5A:
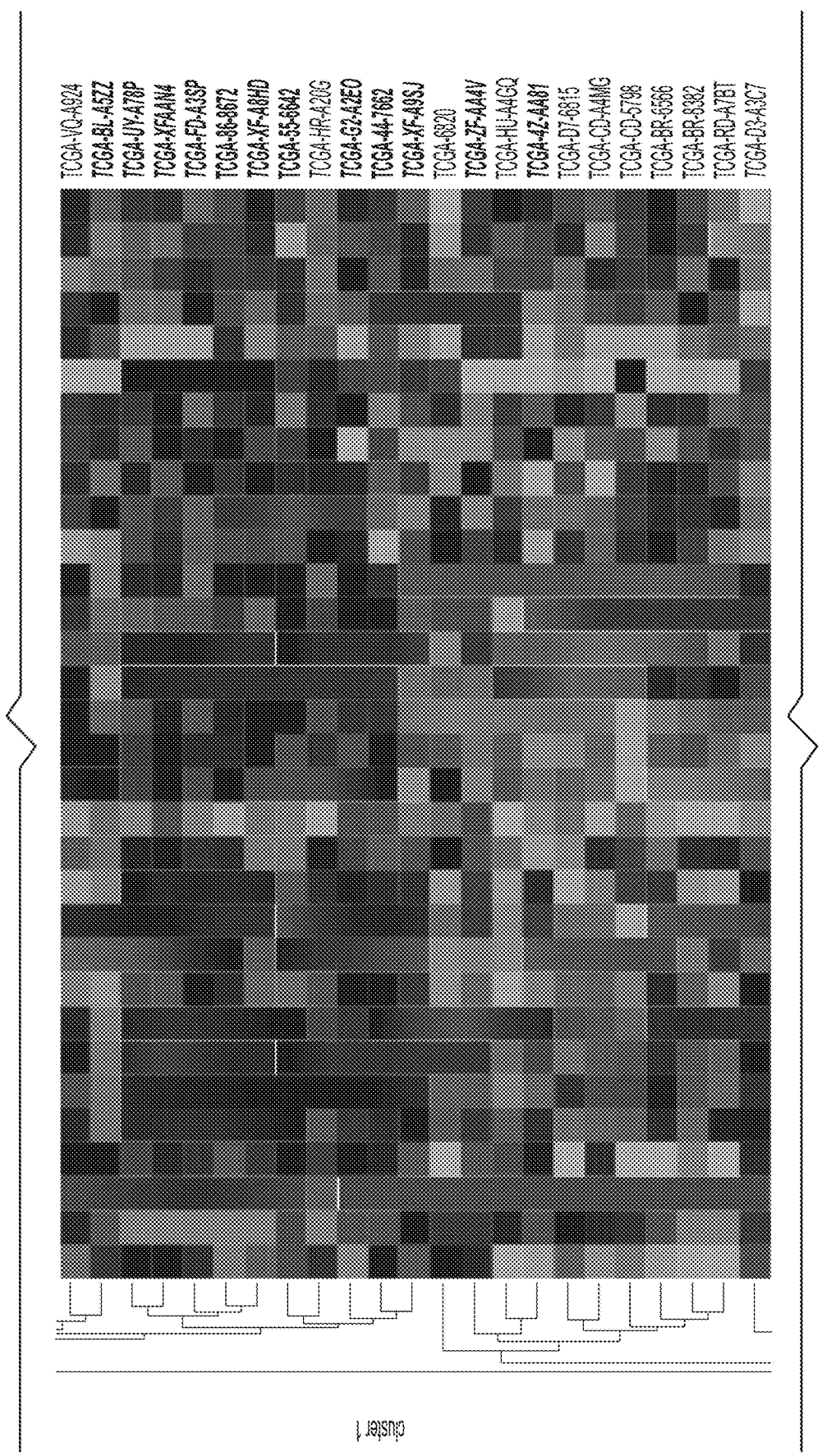
Figure 5A:
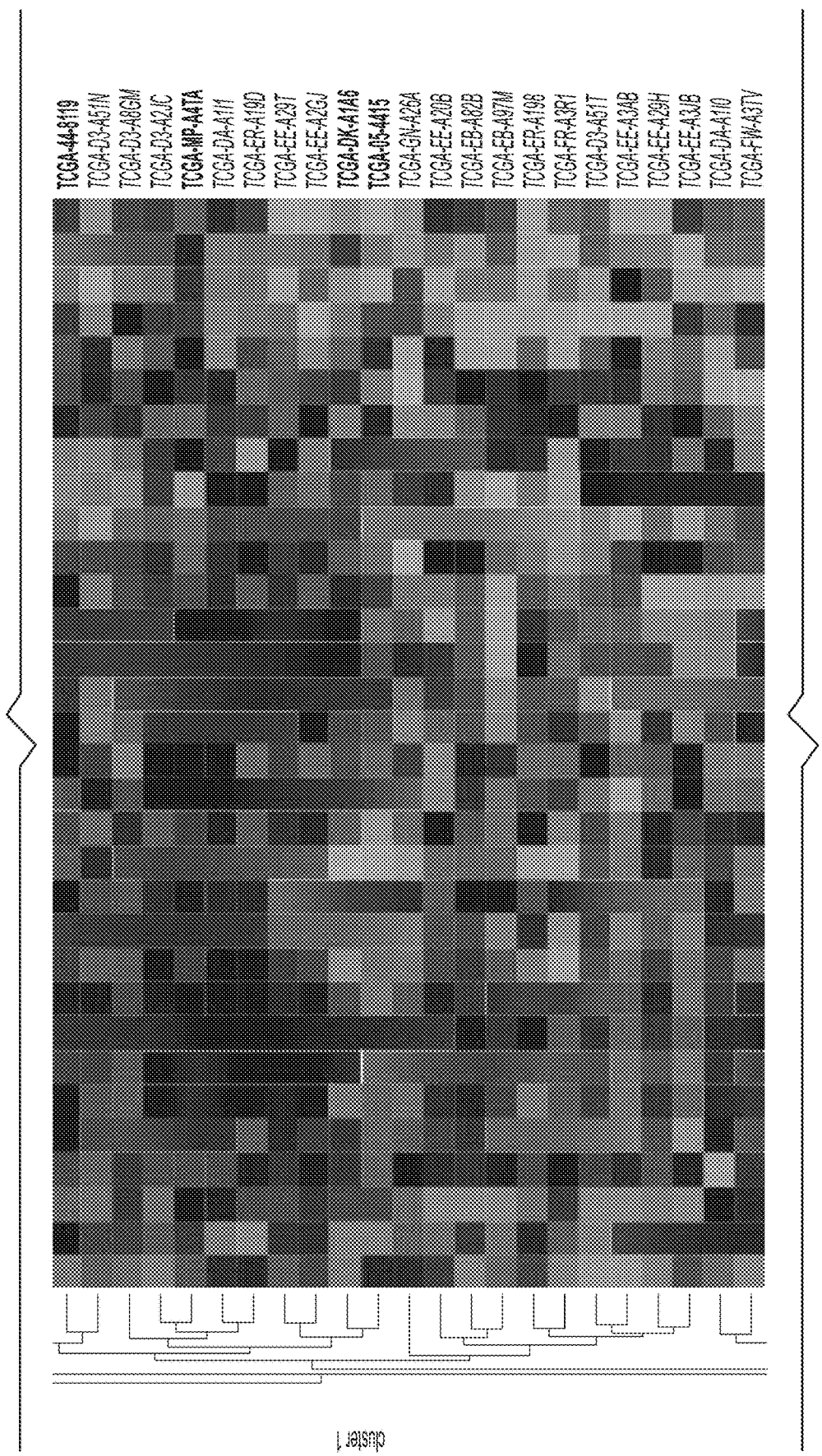
Figure 5A:
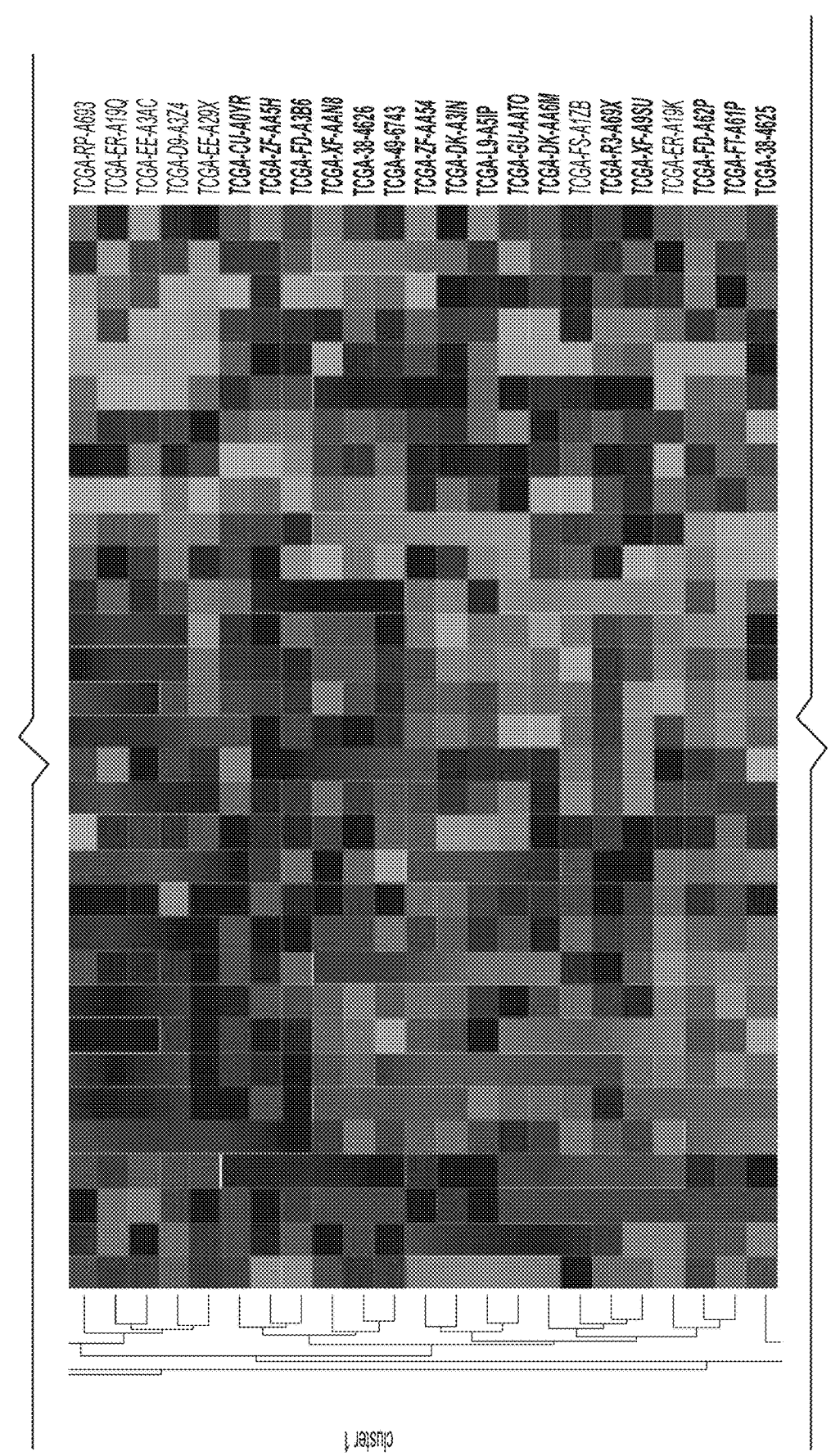
Figure 5A:
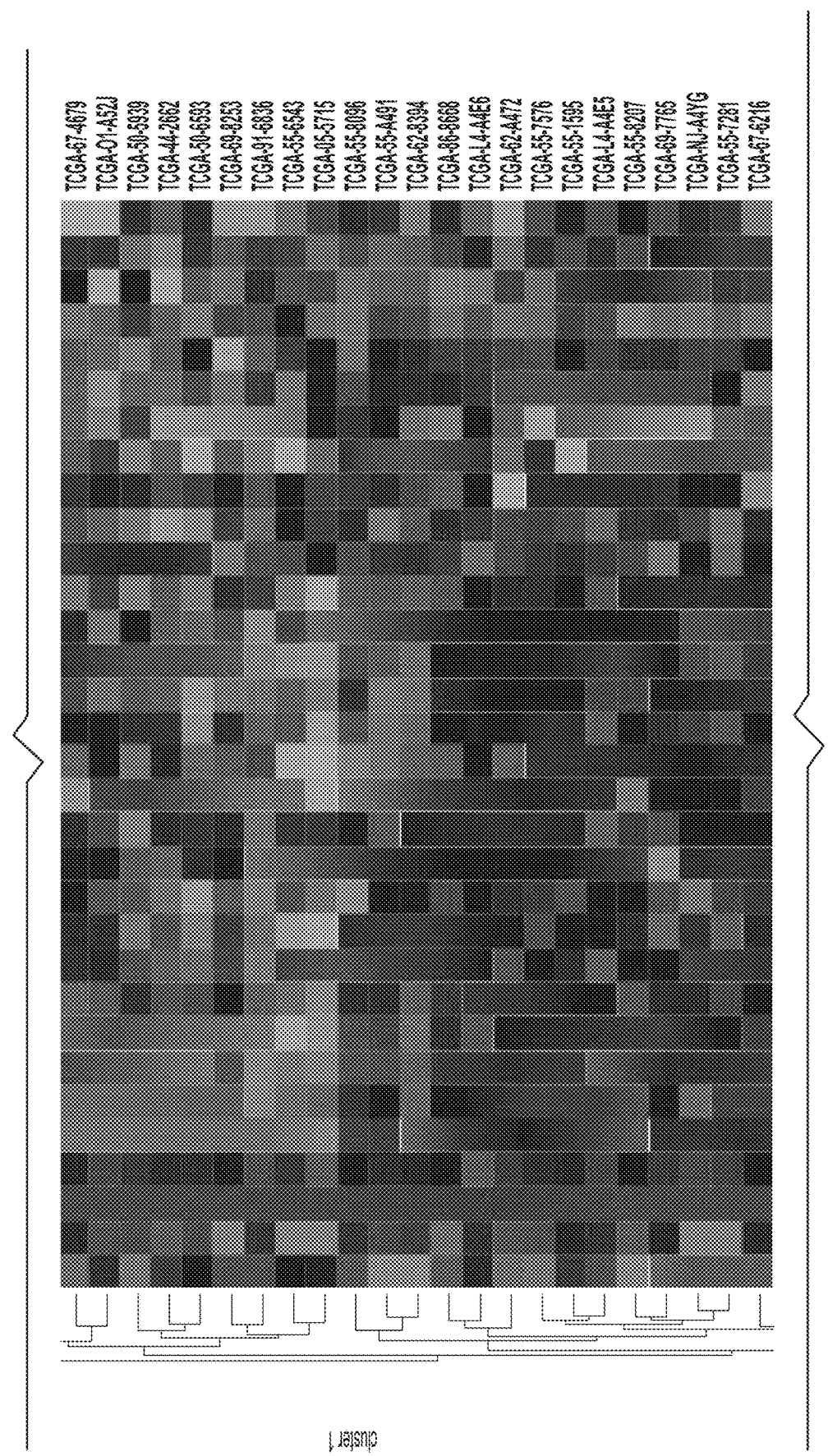
Figure 5A:
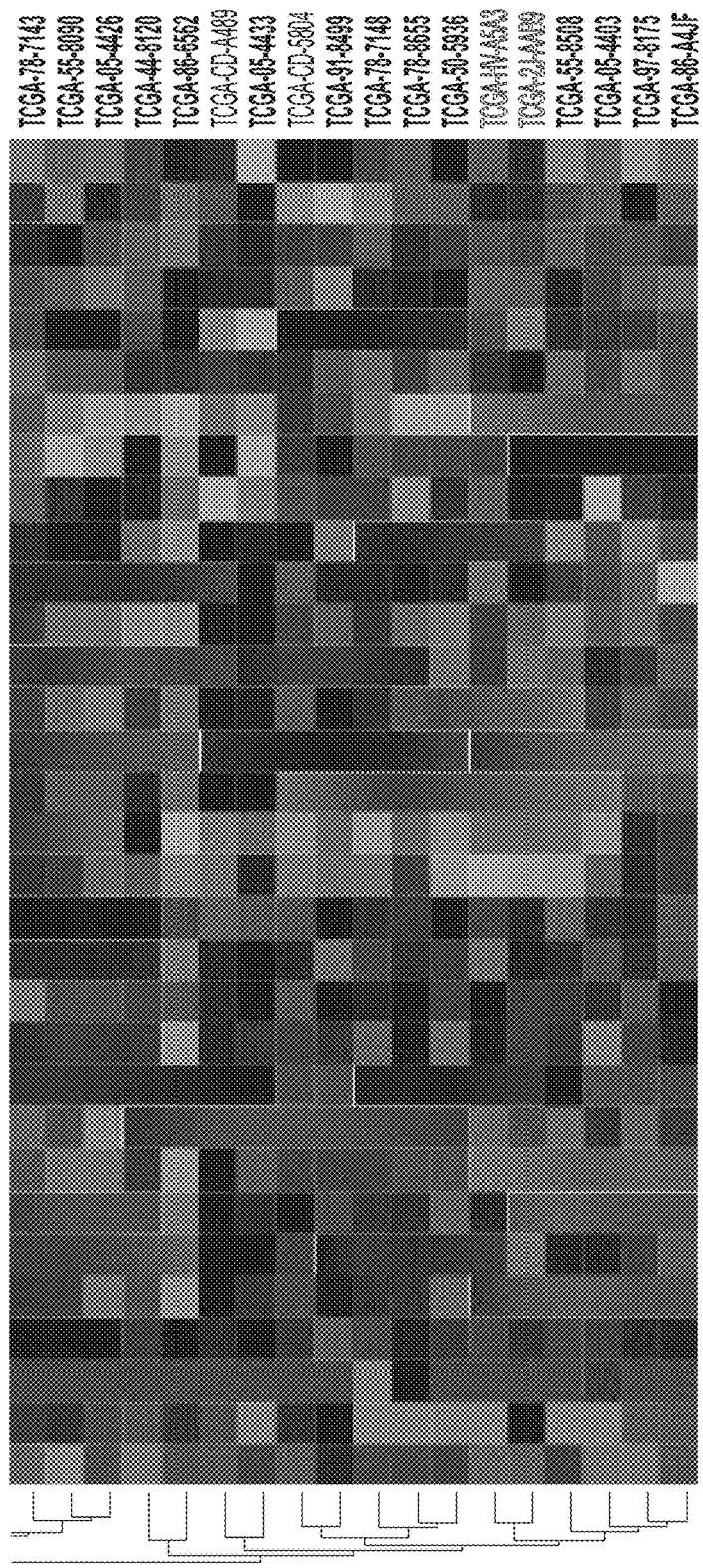
Figure 5A:
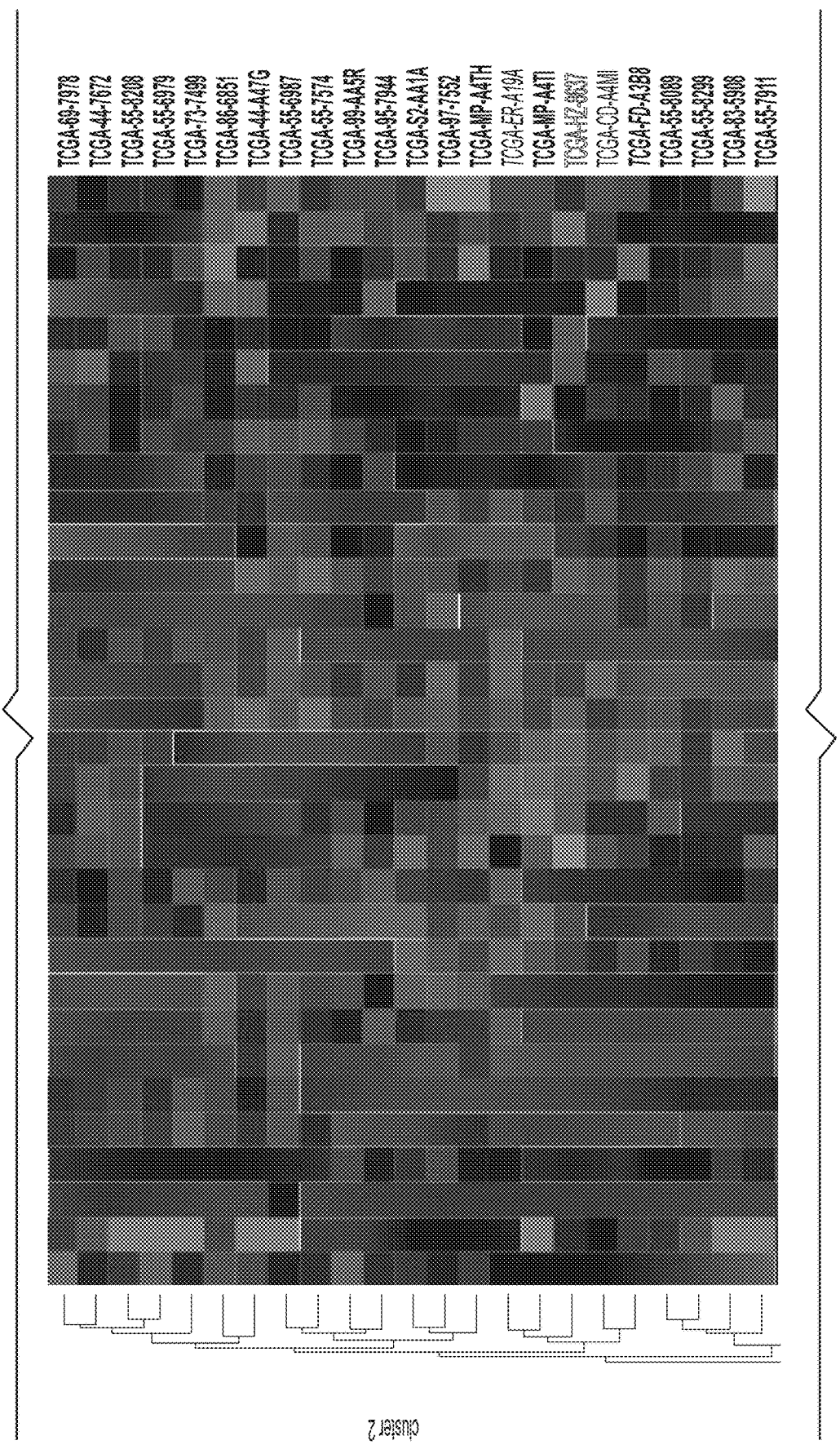
Figure 5A:
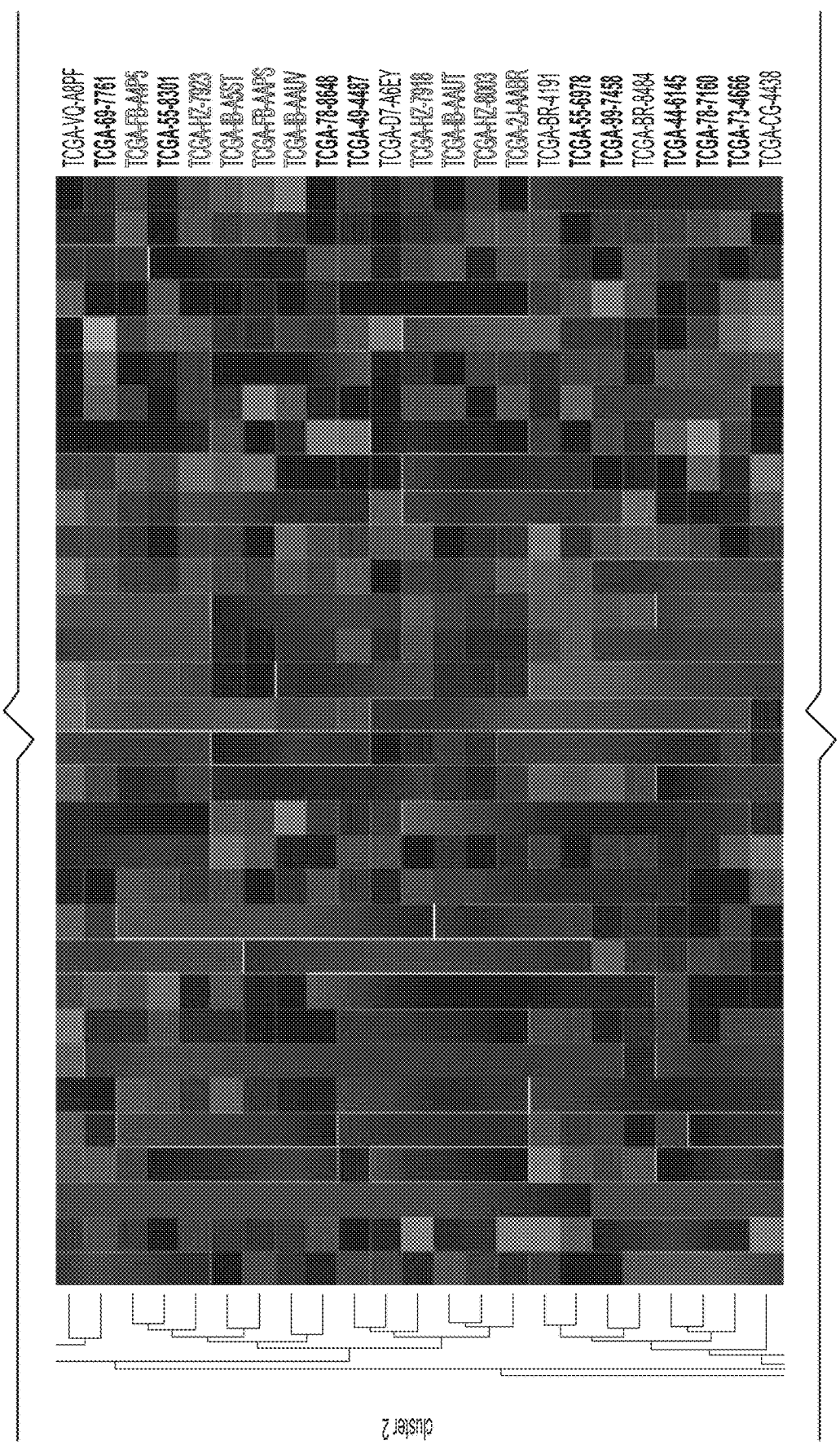
Figure 5A:
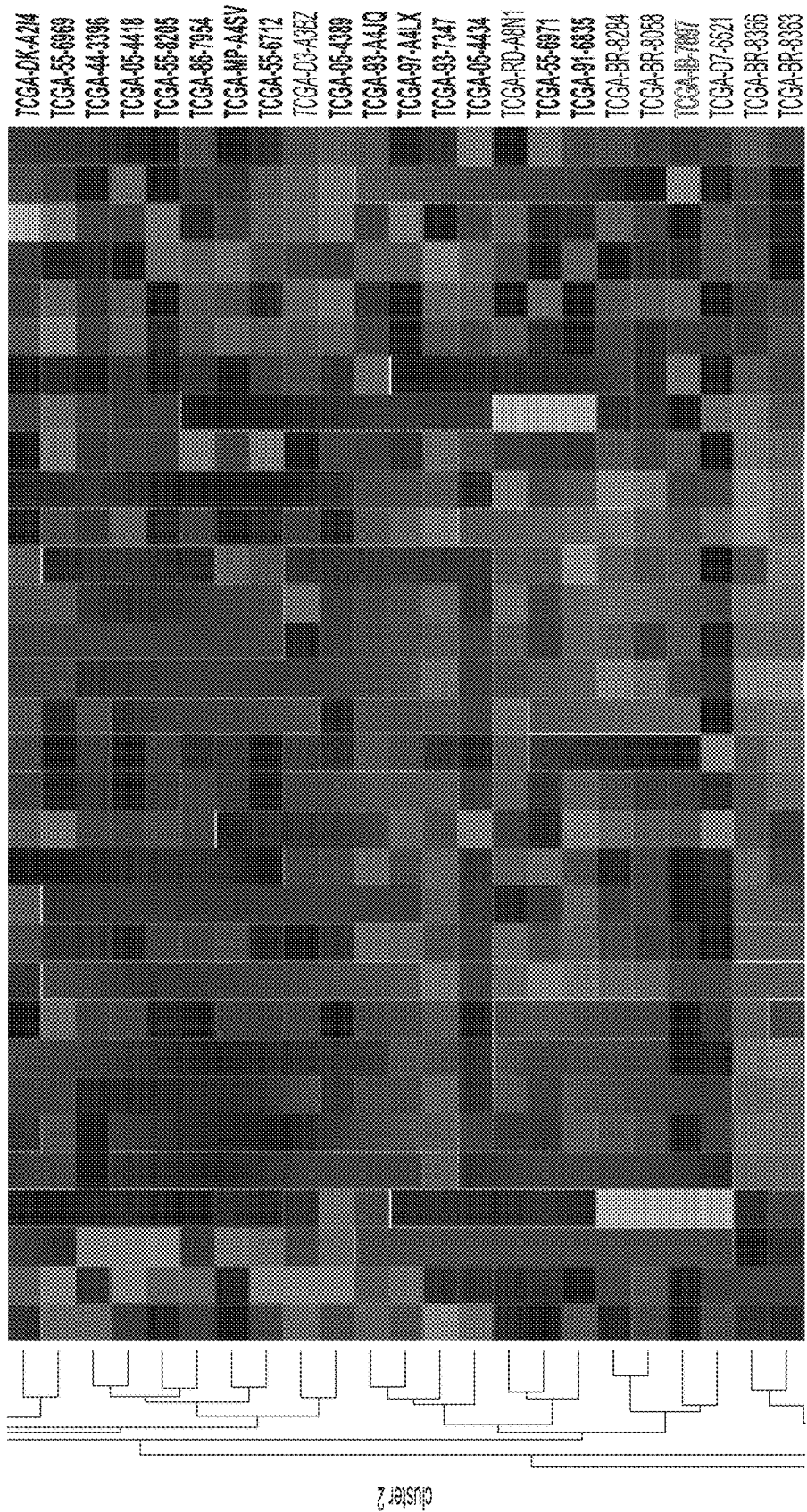
Figure 5A:
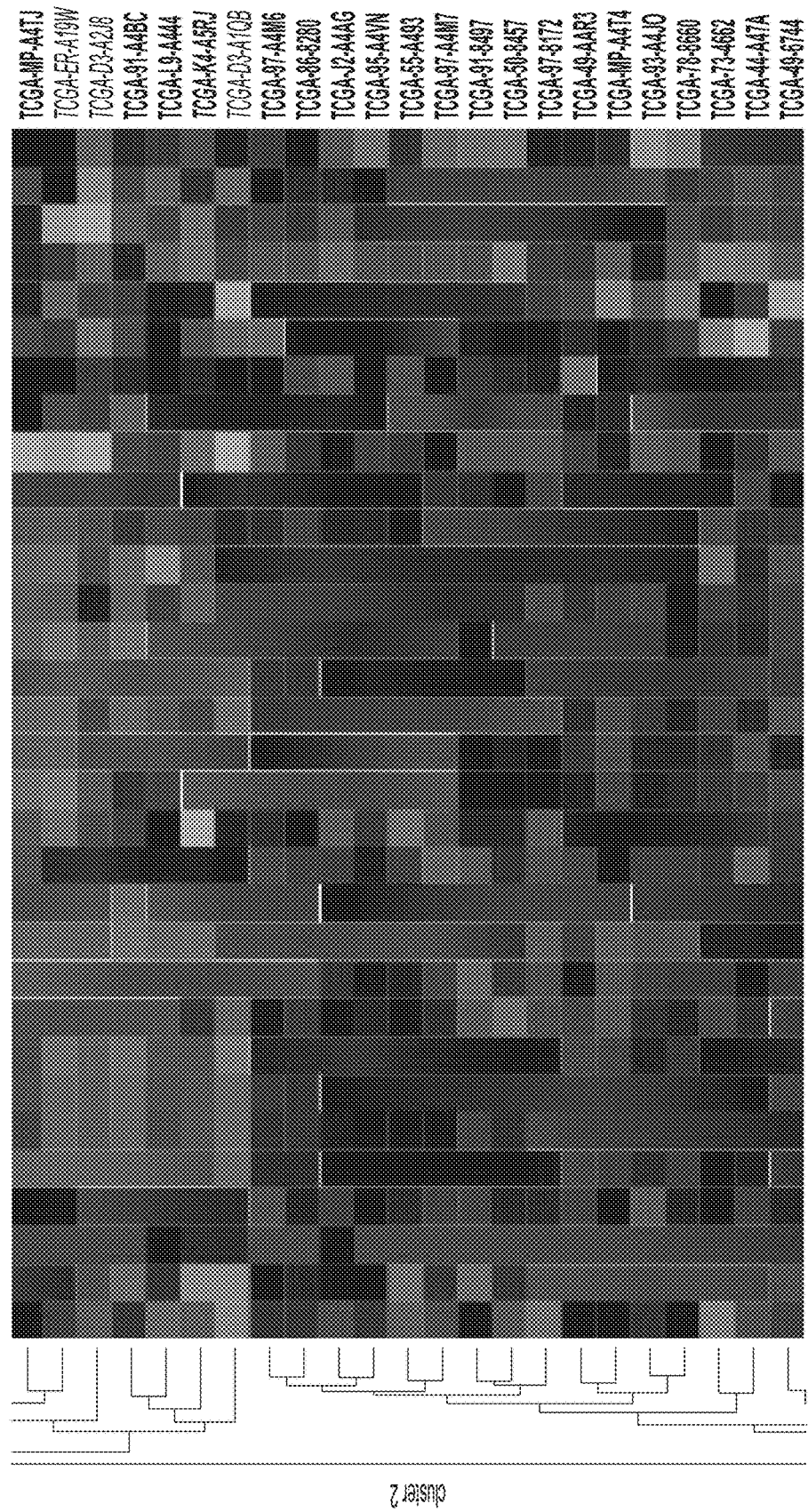
Figure 5A:
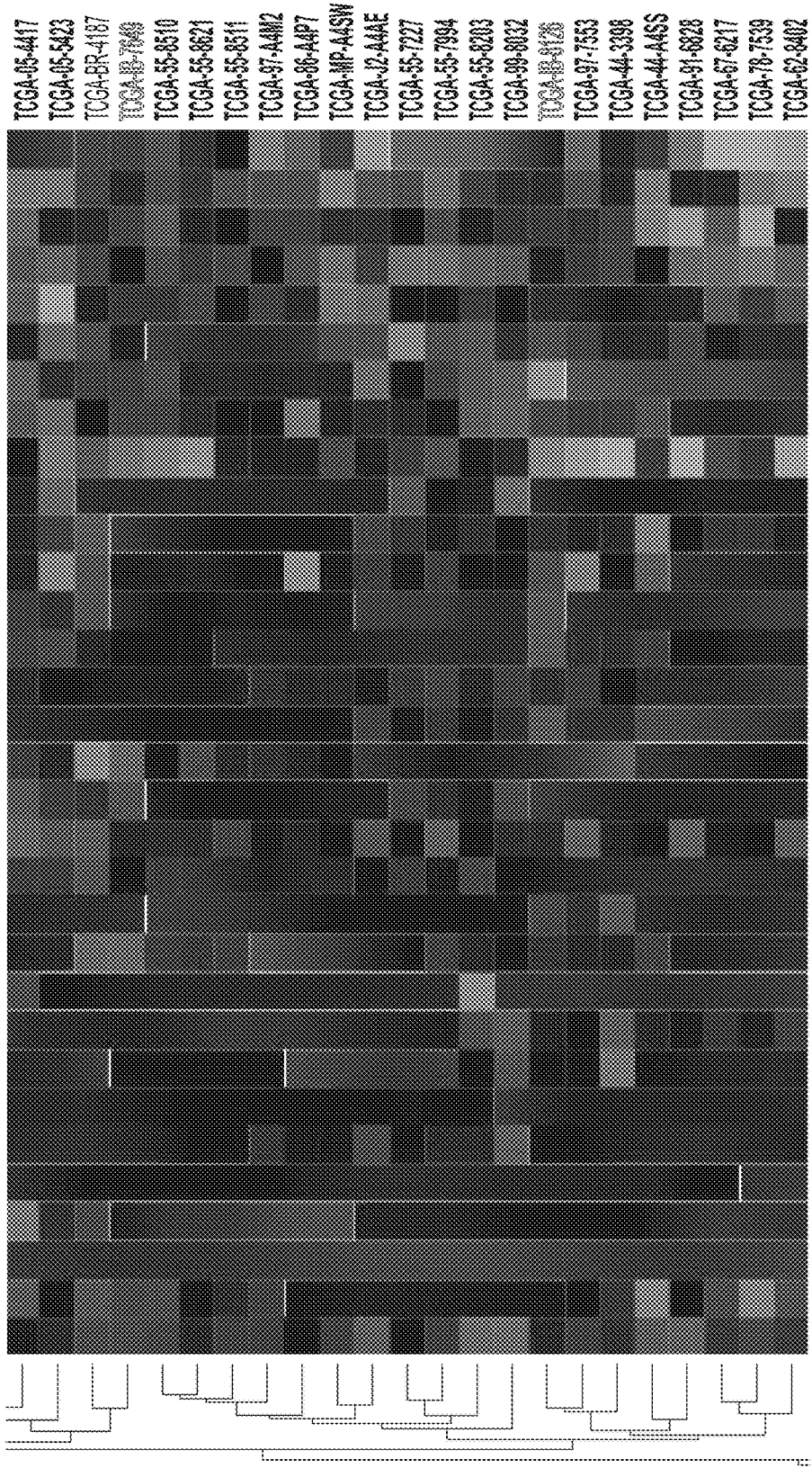
Figure 5A:
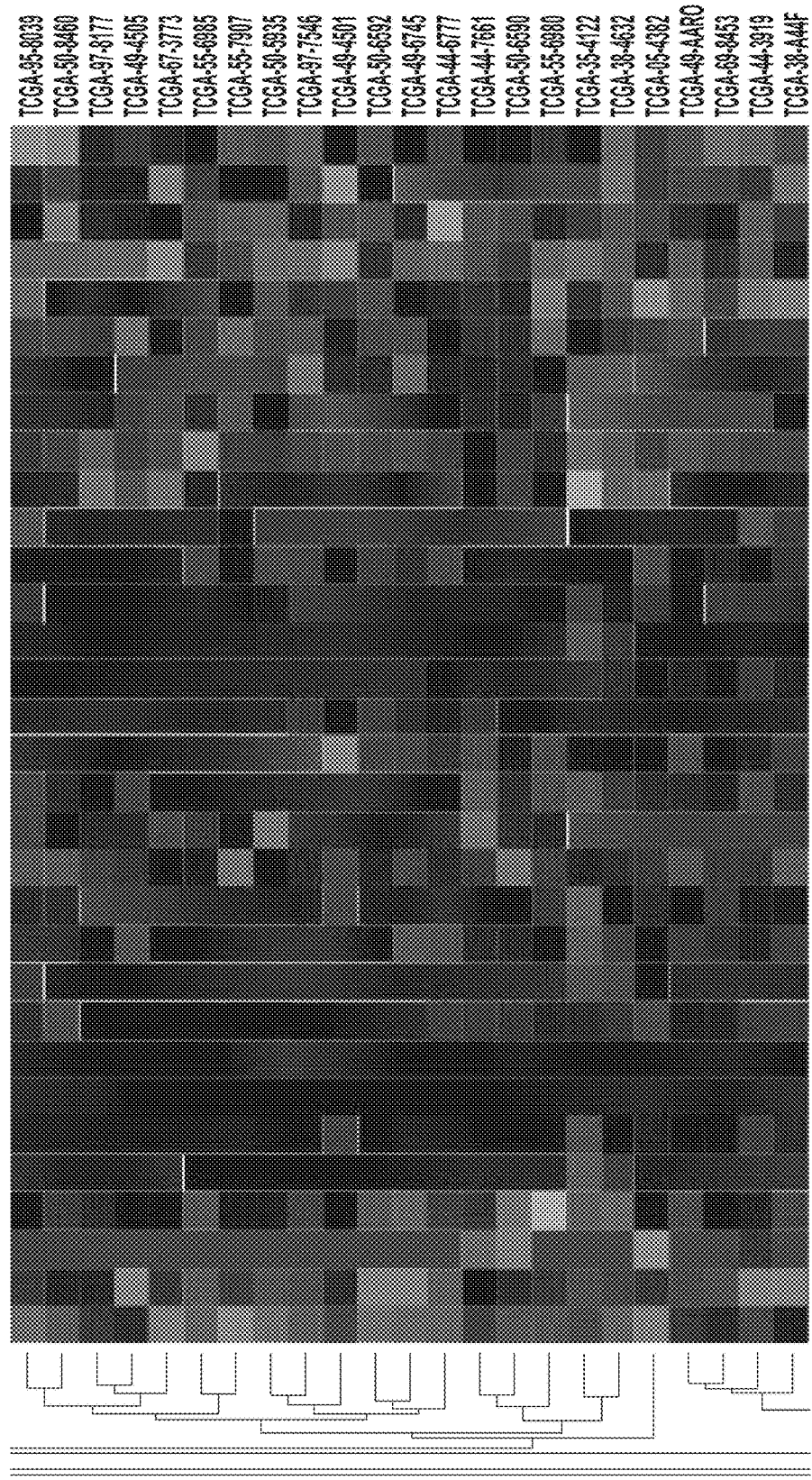
Figure 5A:
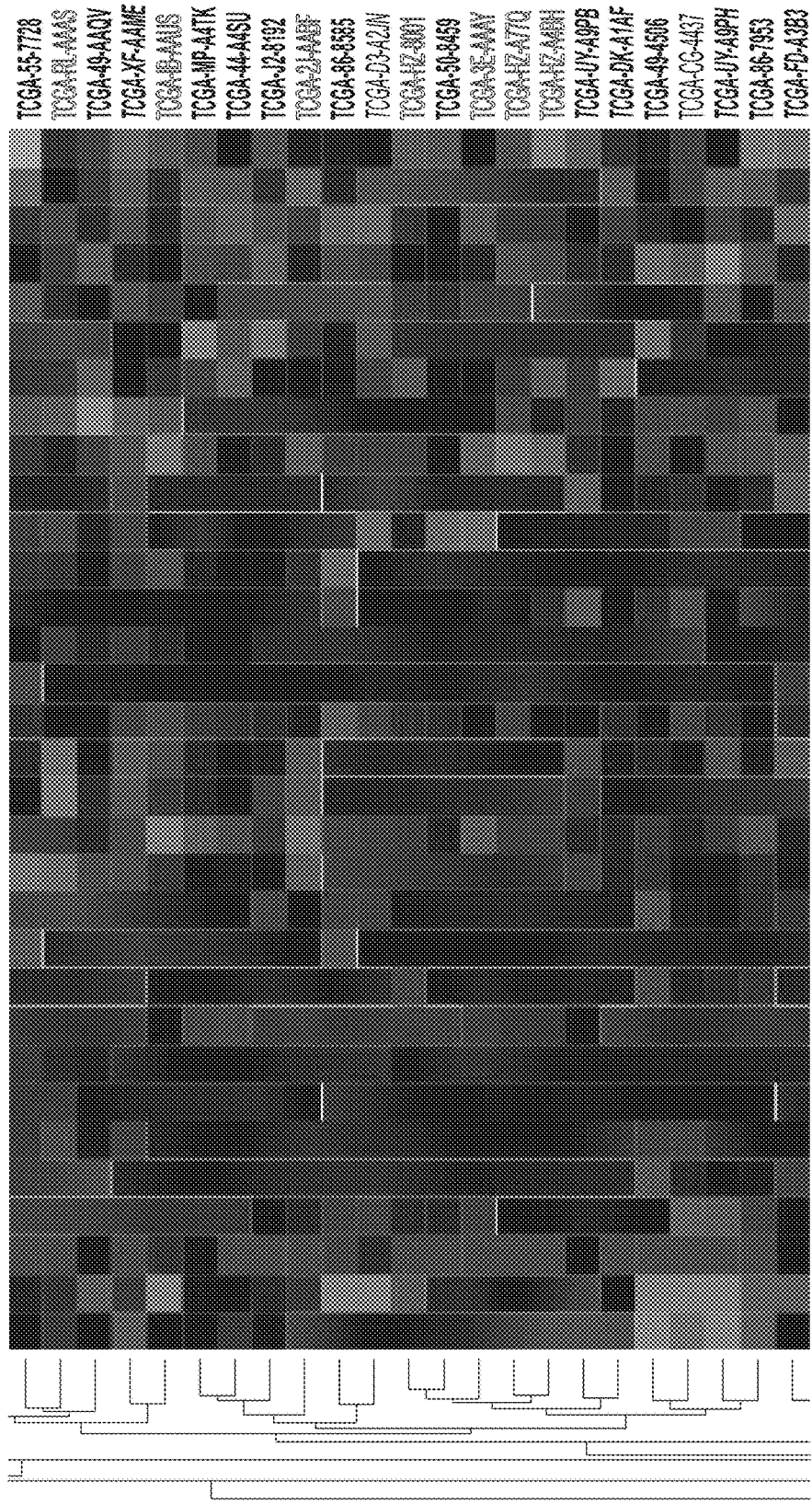
Figure 5A:
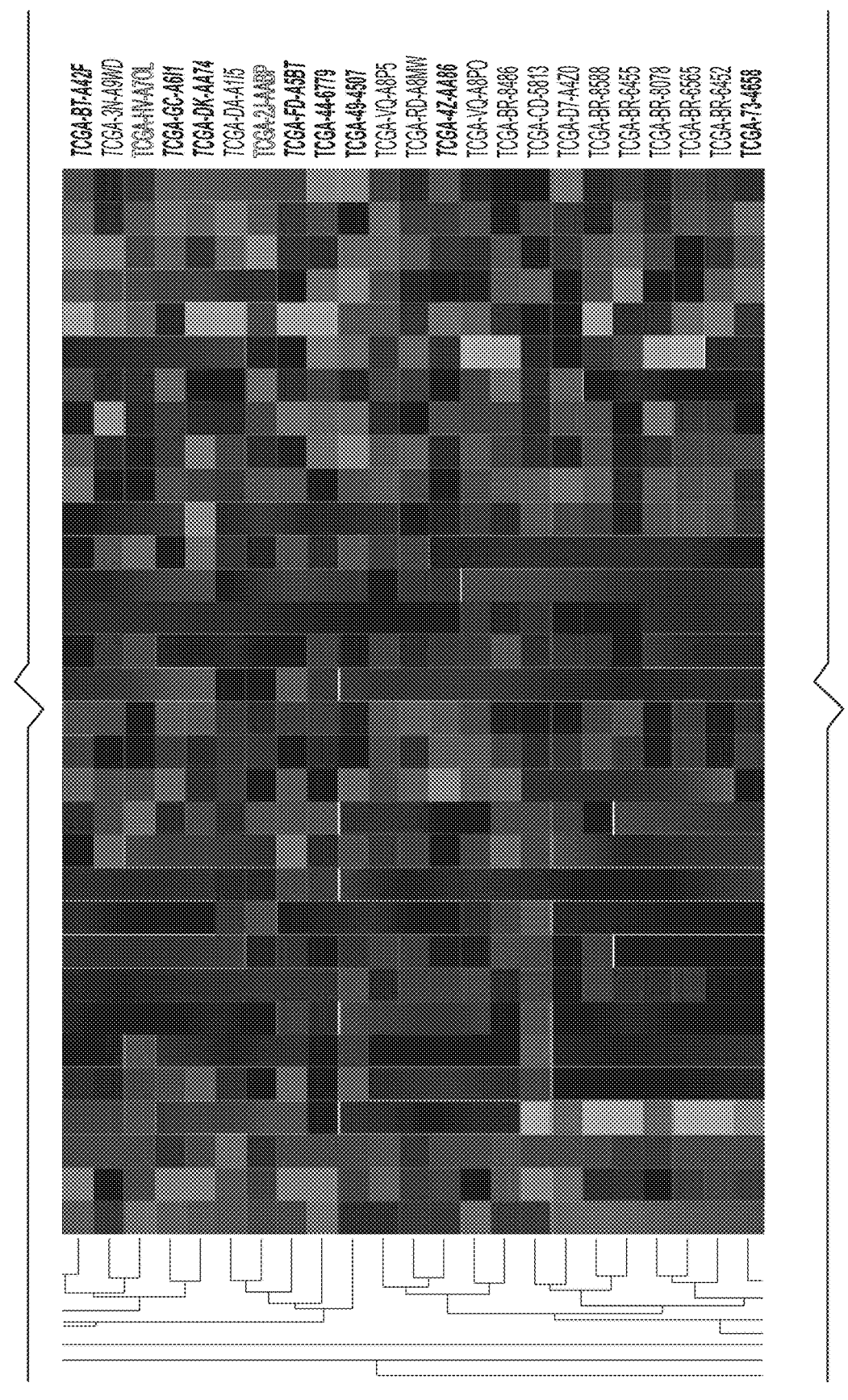
Figure 5A:
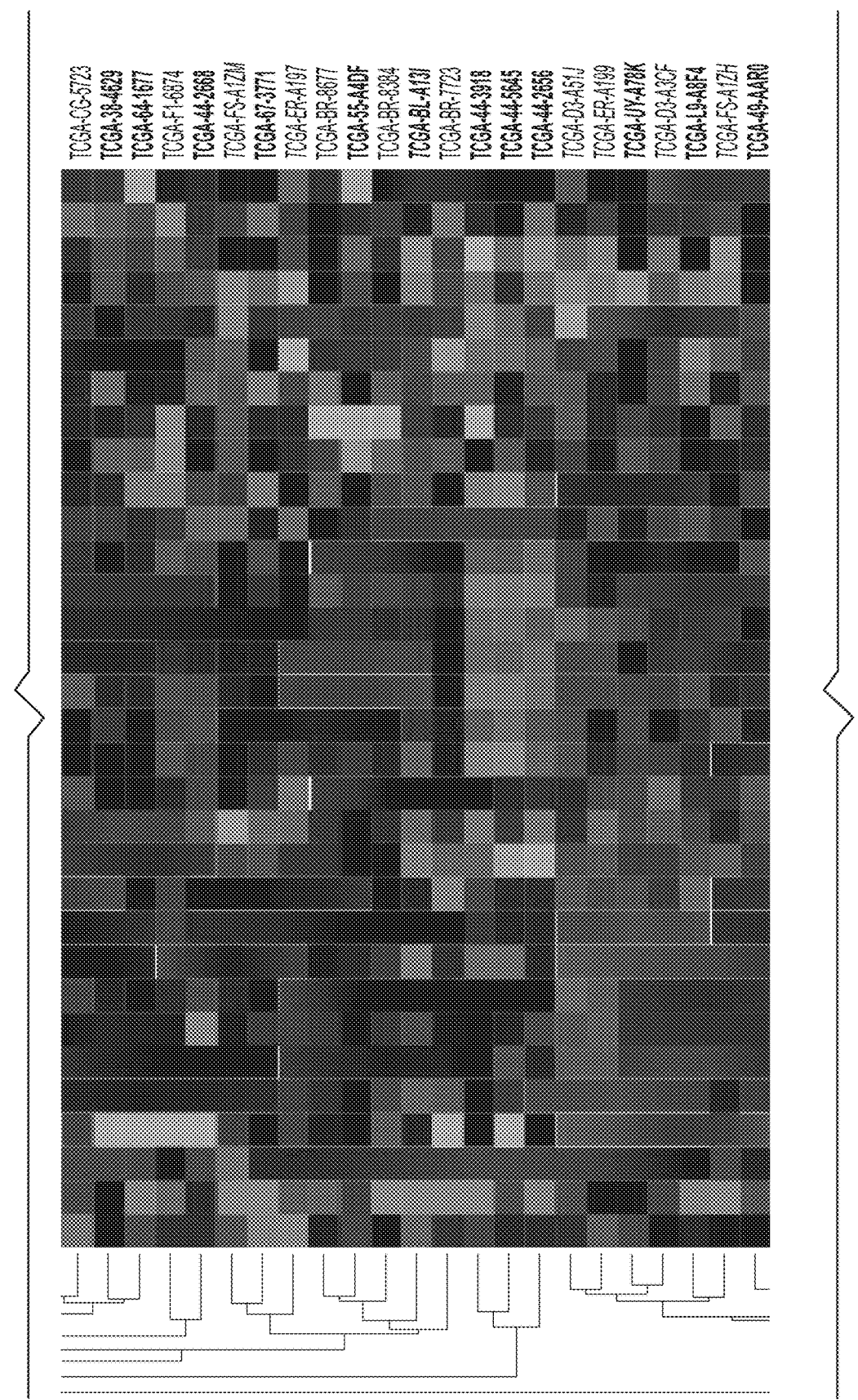
Figure 5A:
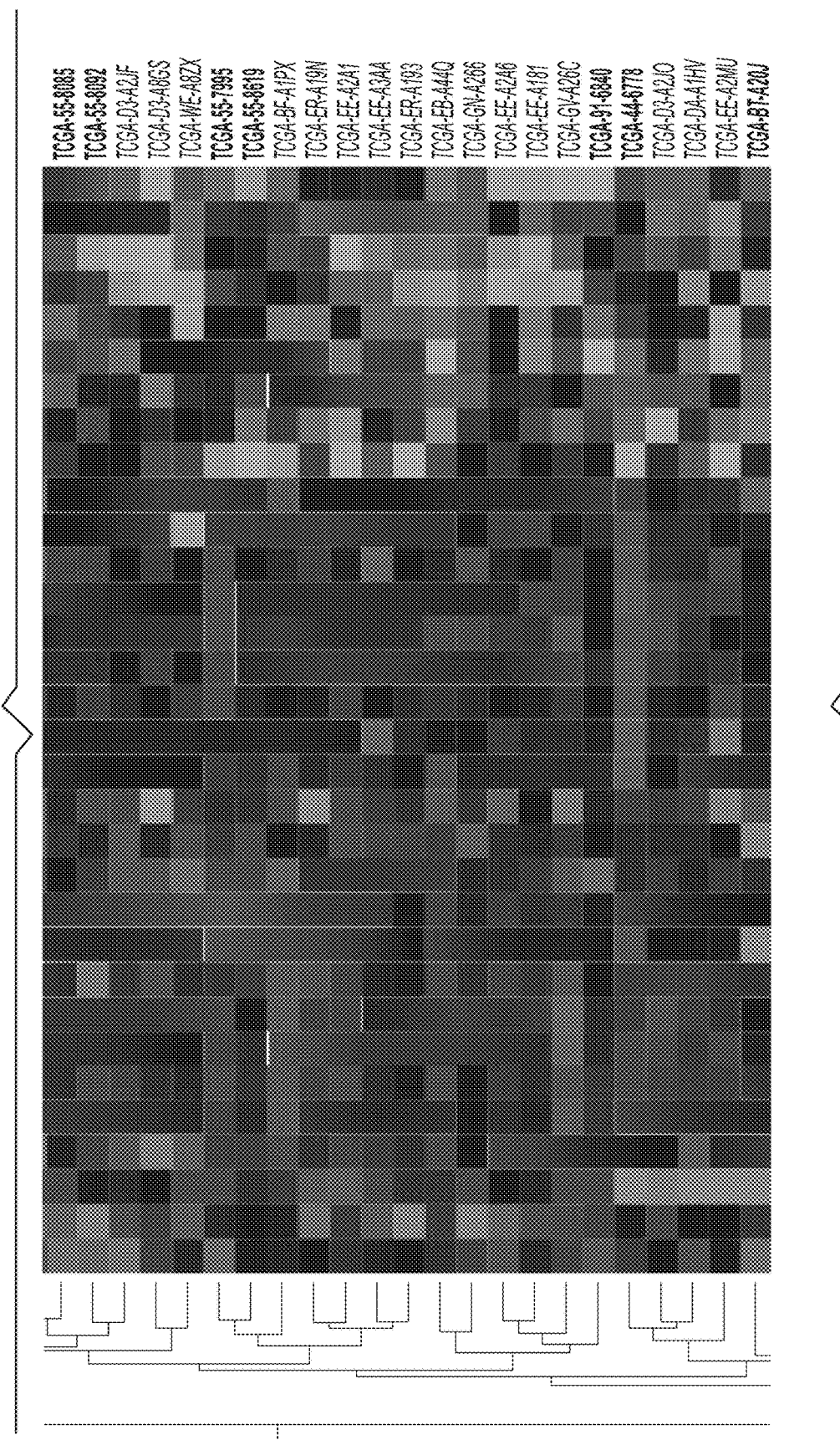
Figure 5A:
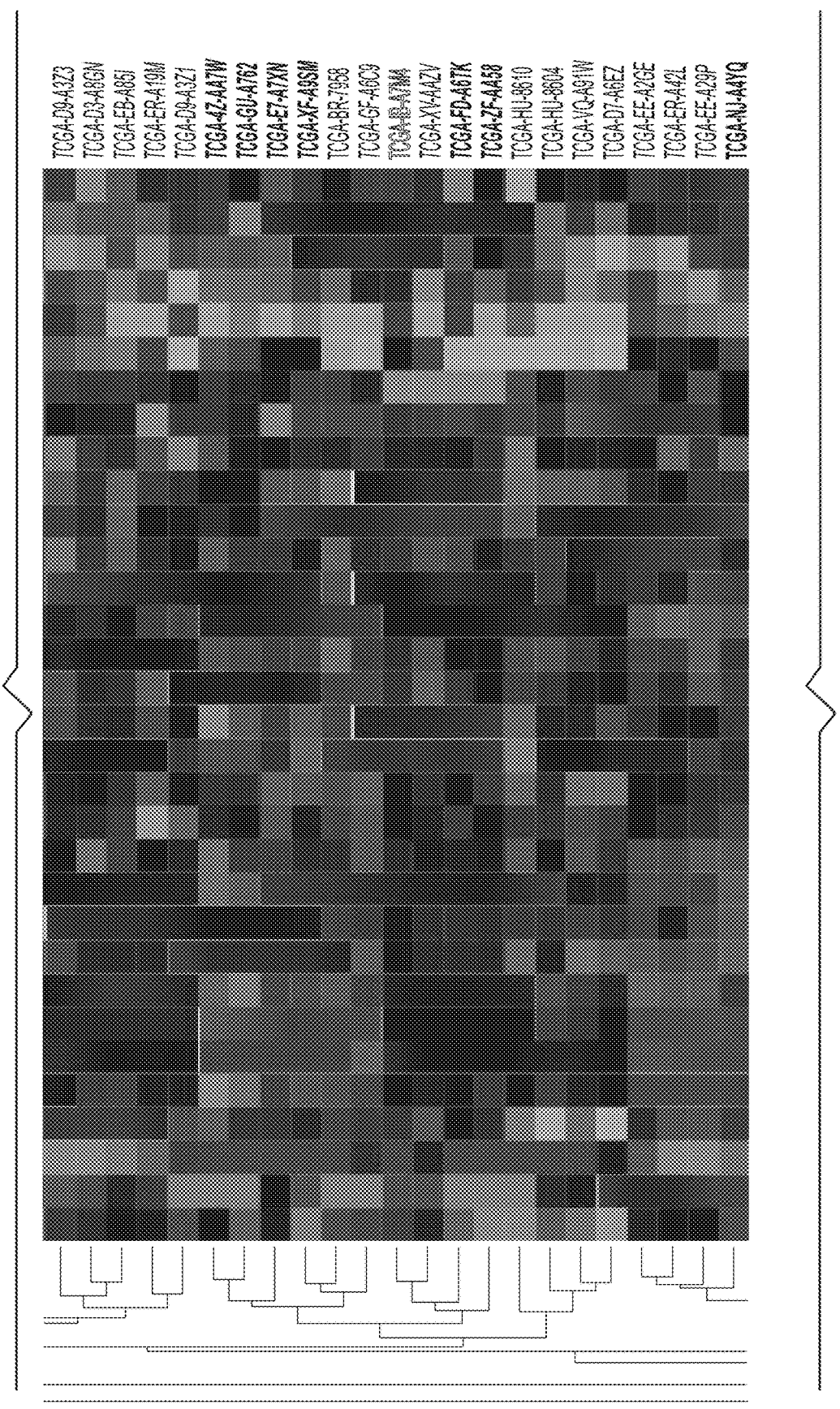
Figure 5A:
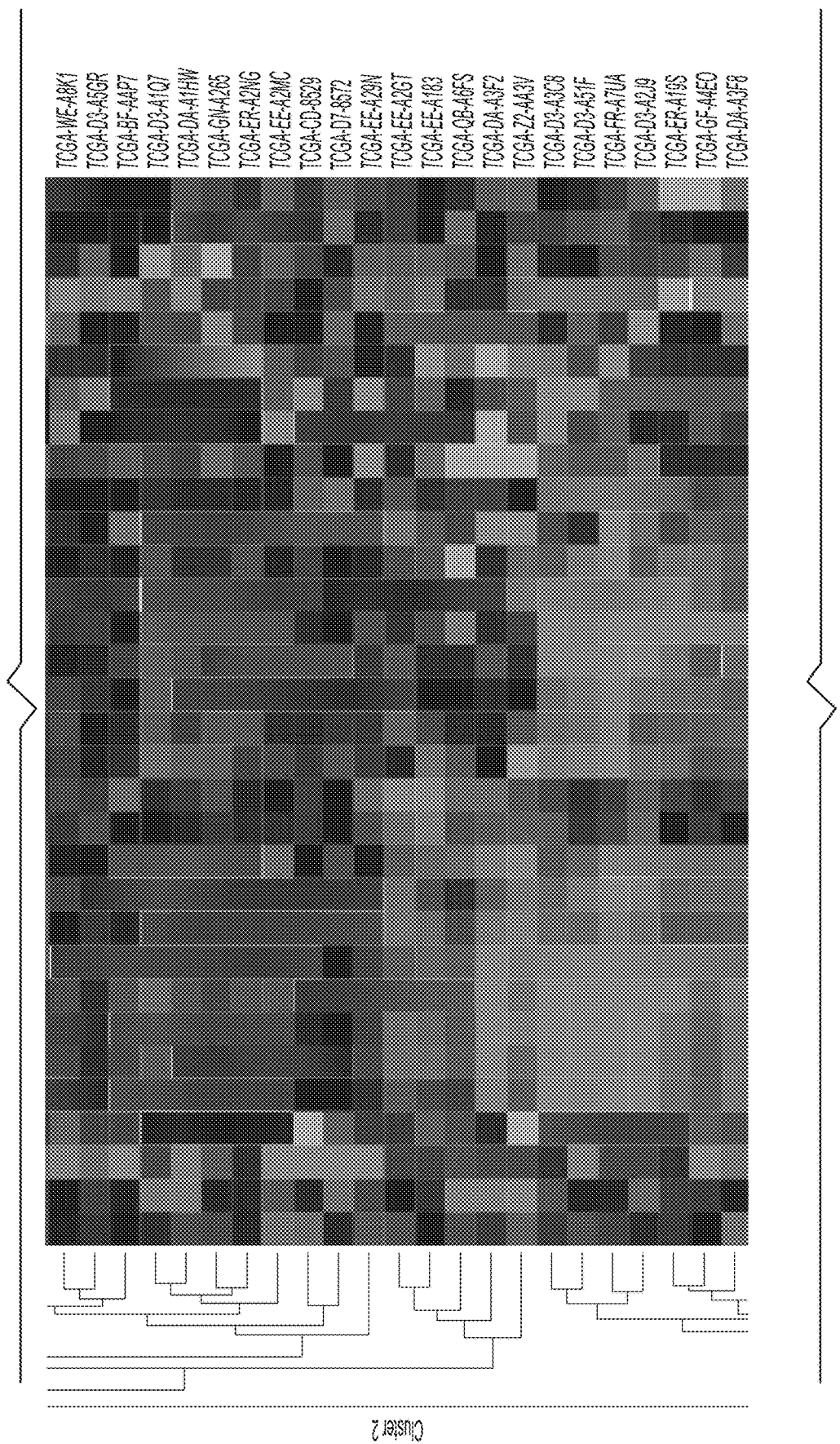
Figure 5A:
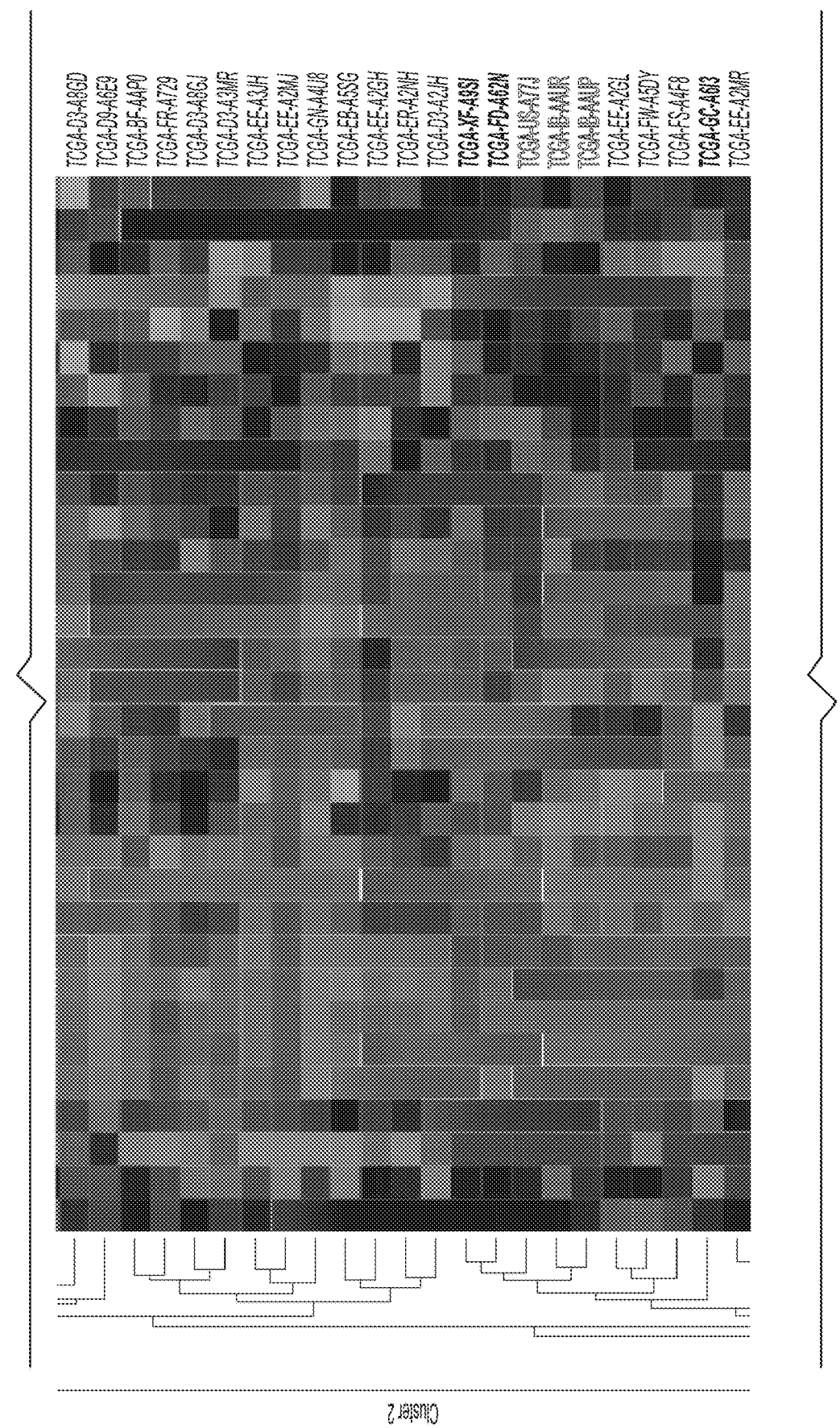
Figure 5A:
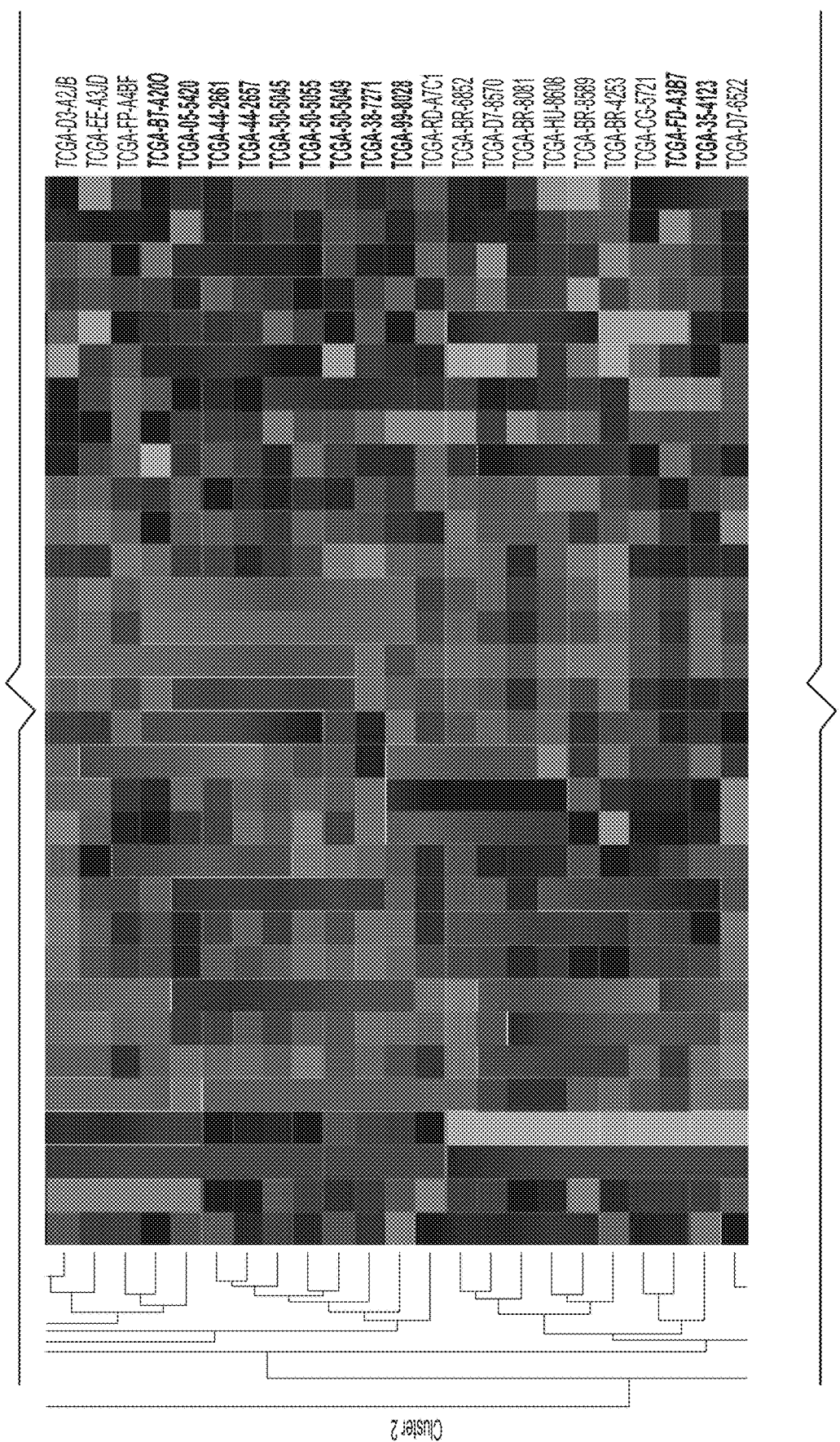
Figure 5A:
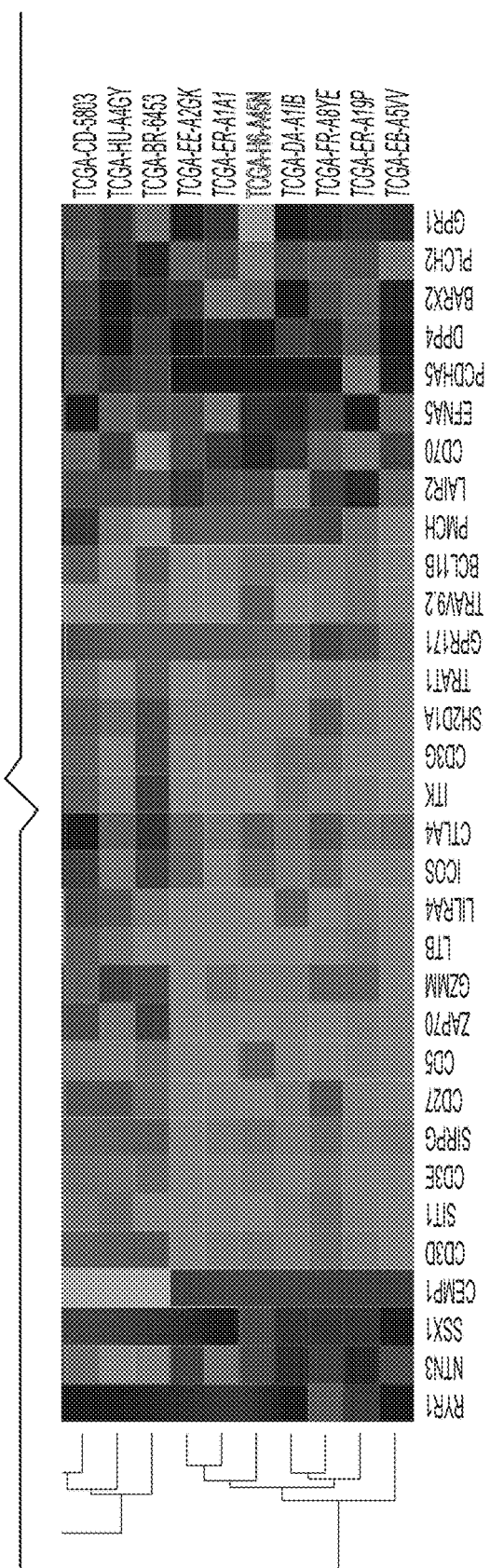
Figure 5A:
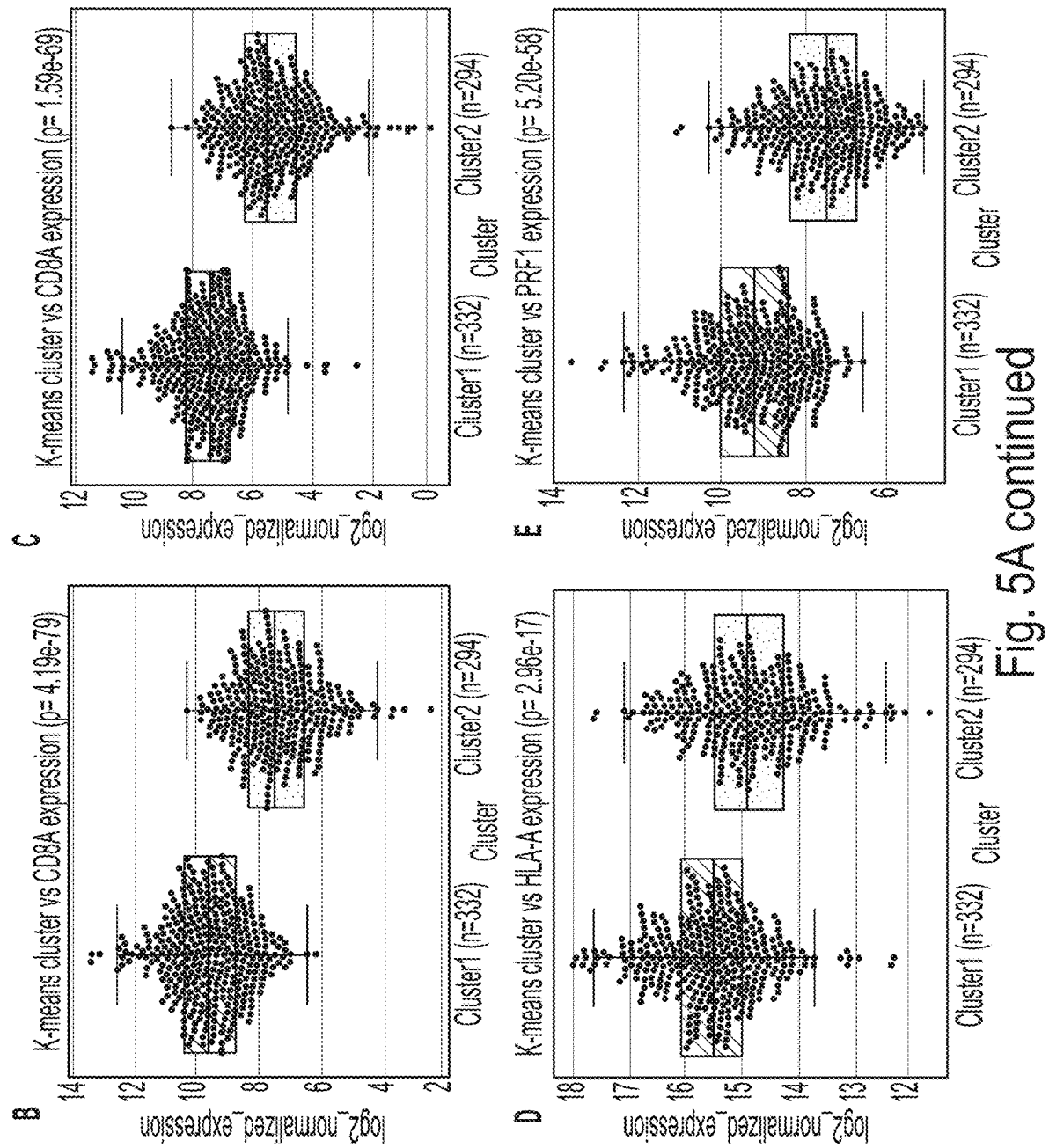
Figure 5B:
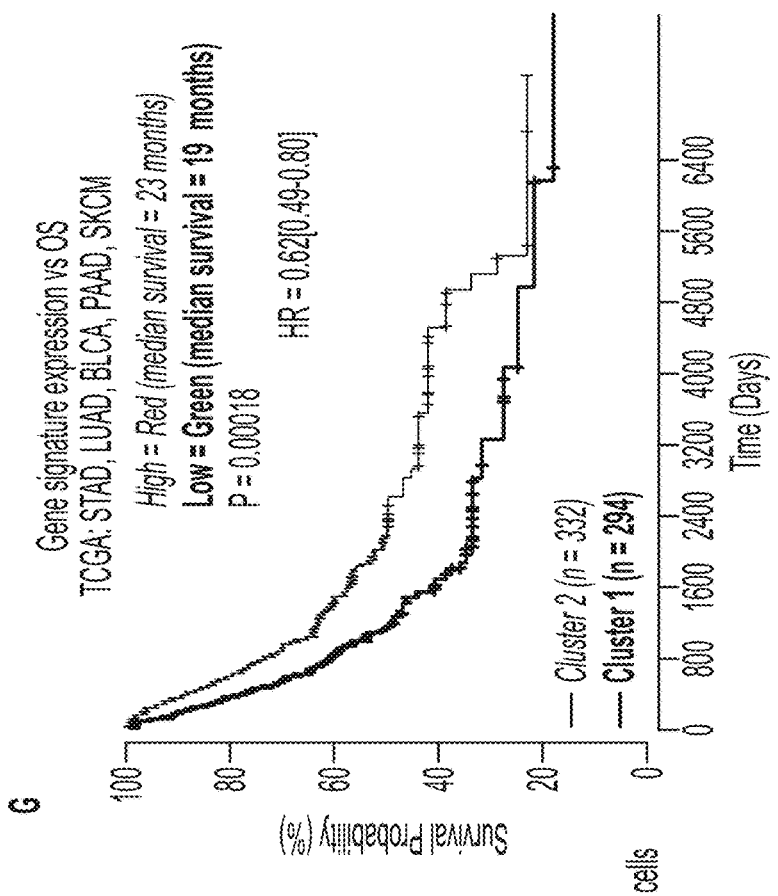
Figure 5B:
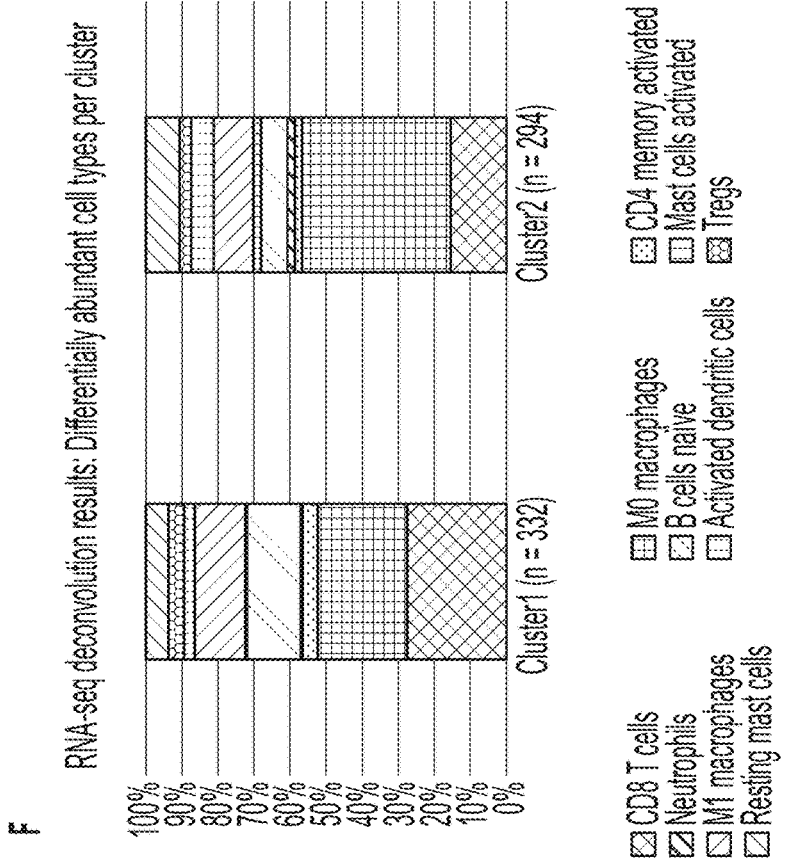

Unsupervised clustering produced two clusters (ncluster 1=332; ncluster 2=294) as is shown in FIG. 5A, Panel A. The inventors observed that cluster 1 patient tumor samples possessed significantly higher levels of CD8A, CD8B, HLA-A, and PRF1 (P<1.0e-15; FIG. 5A, Panels B-E). The inventors also elaborated upon these CD8+ T cell activity markers by showing cluster 1 patients possessed higher abundances of CD8+ T-cells than cluster 2 patients (13.5% vs 6.90%; P=2.15e-21; FIG. 5B, Panel F).

Although clinical drug response data was not available for these 636 patients, the inventors examined patient OS between the clusters produced from the 32-gene signature (FIG. 5A, Panel A). Indeed, higher expression of the gene signature was associated with OS in this larger dataset. The median OS duration for the higher expressing cluster 1 patients was significantly longer than that of the cluster 2 patients (P=1.8e-4; FIG. 5B, Panel G), which was in line with the OS results previously discussed (FIG. 3, Panel A).

Figure 6A:
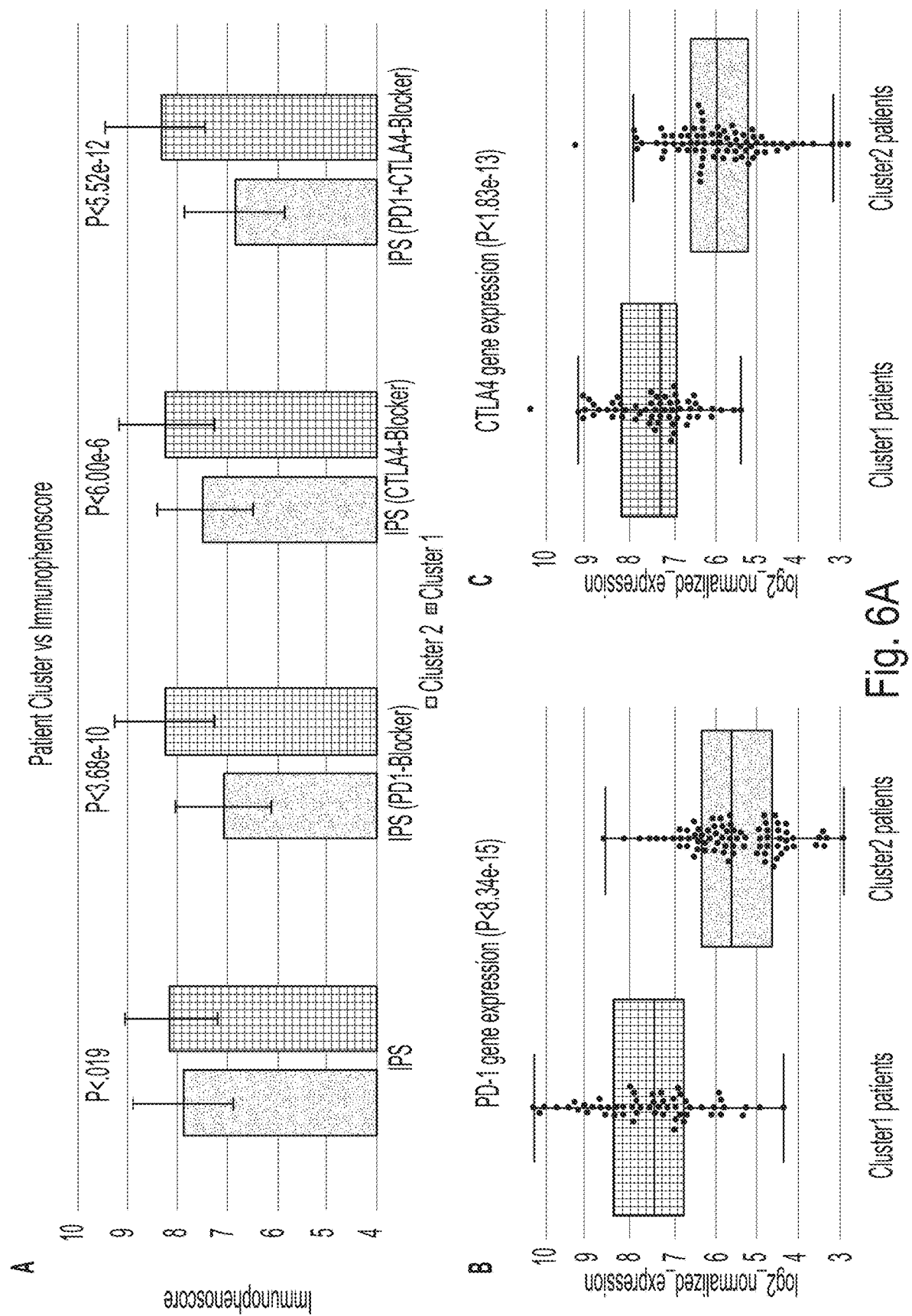
FIGS. 6A and 6B depict patient immunophenoscore and immunotherapy gene set analysis. (A) mean Immunophenoscores represented per cluster derived as described in methods (bar whiskers represent standard deviations). Normalized gene expression plots between cluster1 and cluster2 patients for (B) PD-1 (P<8.34e-15) and (C) CTLA-4 (P<1.83e-3). (D) K-means clusters produced by each the immunotherapy gene set (19) and our gene set, with both gene sets showing enrichment for chemosensitive tumor samples (P=0.015, and P=0.0007, respectively). Concordance table showing similar unsupervised clusters are produced with 'good' concordance (Cohen's kappa=0.64). (E) cluster1 patients possessed significantly elevated expression for 12 out of 18 genes identified by the 2CT-CRISPR assay system (acceptable P<0.003).

Patient immunophenoscore and immunotherapy gene set concordance: Recent work has shown the utility of the Immunophenoscore (IPS) to predict response to immune checkpoint blockade in melanoma patient tumors based on higher pre-existing immunogenic potential. Therefore, the inventors reasoned that if cluster1 was indeed representative of a more immunogenic phenotype, then cluster 1 tumor samples should too display an elevated IPS, which has been clinically validated for immunotherapeutic response. Analysis of patient IPS between cluster 1 and cluster 2 revealed significant elevation in the general IPS of cluster 1 (P=0.019). In addition, the IPS-PD1, IPS-CTLA4, and IPS-PD1/CTLA4 were highly enriched in cluster 1 tumor samples (P=3.68e-10, P=6.00e-6, and 5.52e-12, respectively; FIG. 6A, Panel A). These scores were designed to be assessed for patients with the potential to be administered checkpoint blockade therapy (e.g., Nivolumab, Ipilimumab), who possessed elevated expression of PD-1 and or CTLA-4. Indeed, cluster 1 patients possessed significantly higher PD-1 and CLTA-4 gene expression than cluster 2 patients (P<8.34e-15 and P<1.83e-13; FIG. 6A, Panels B-C, respectively).

Figure 6B:
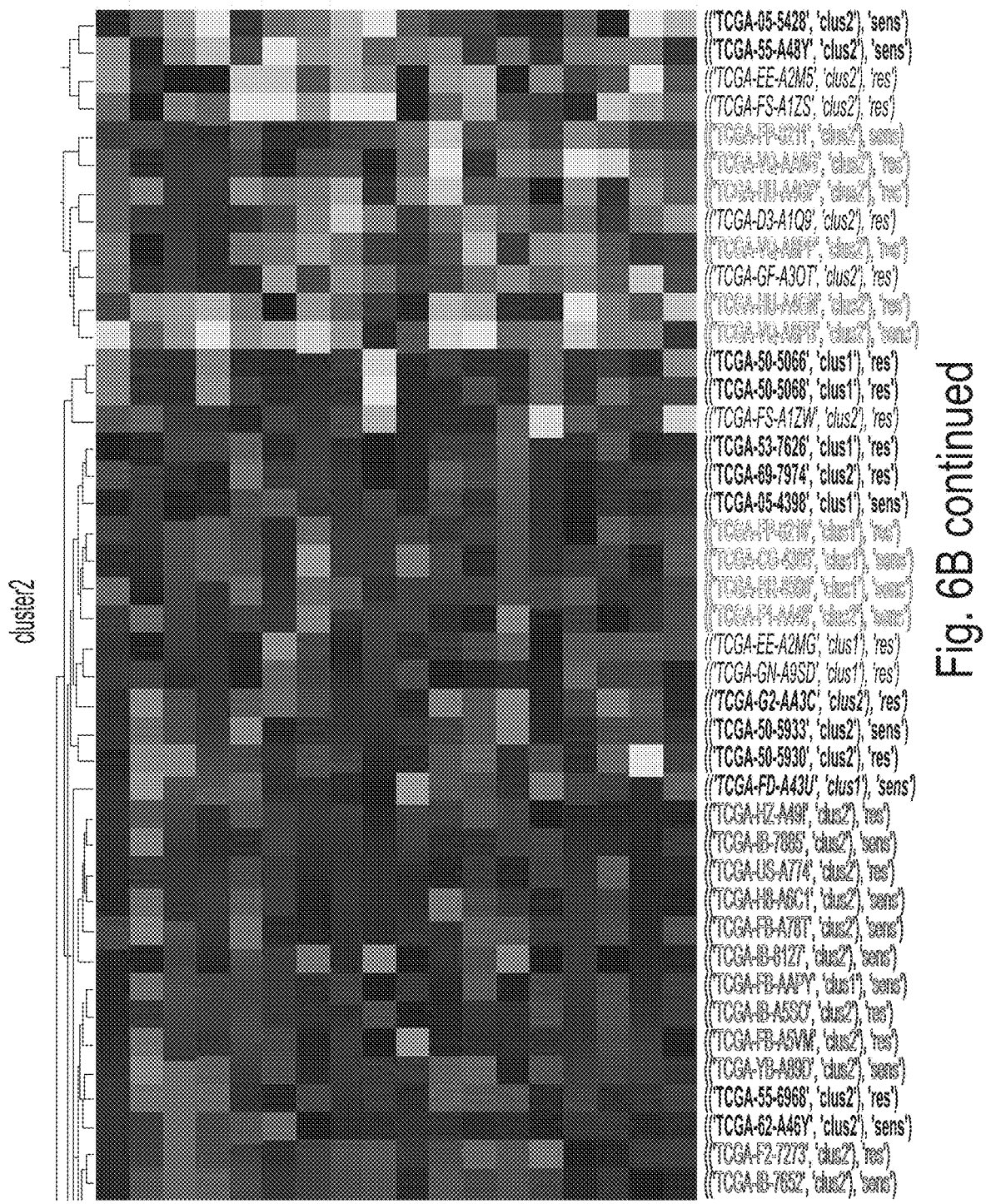
Figure 6B:
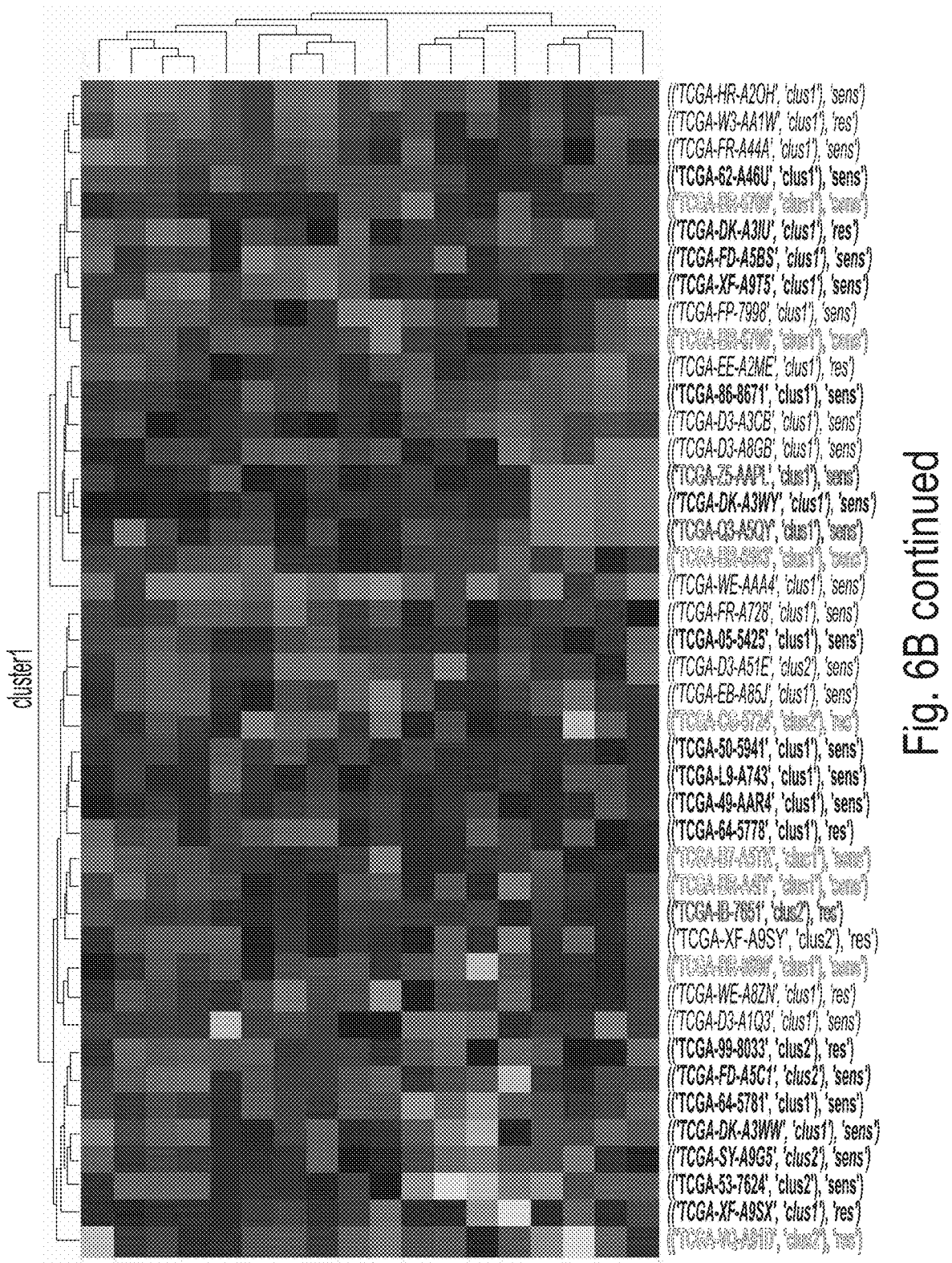
Figure 6B:
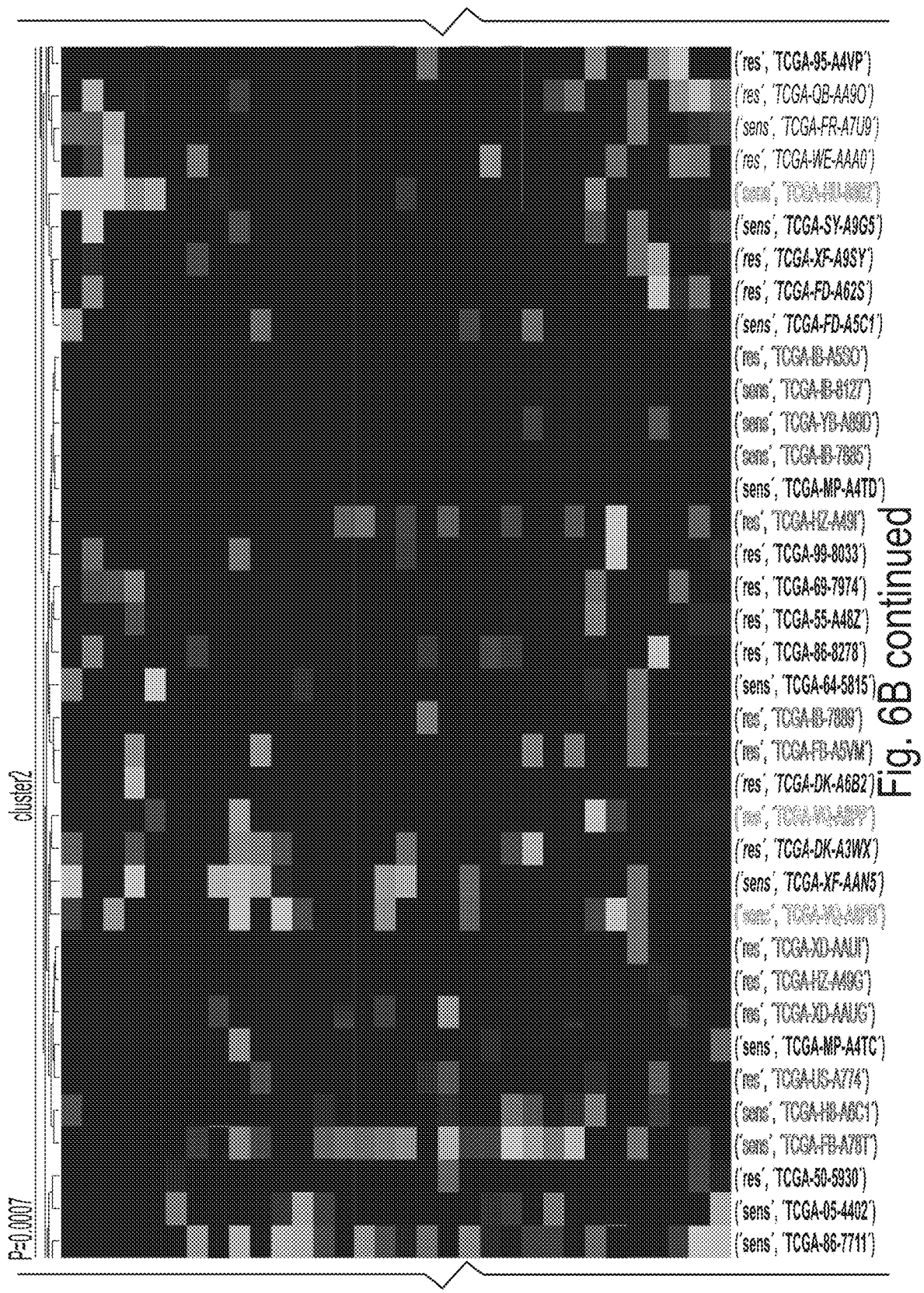
Figure 6B:
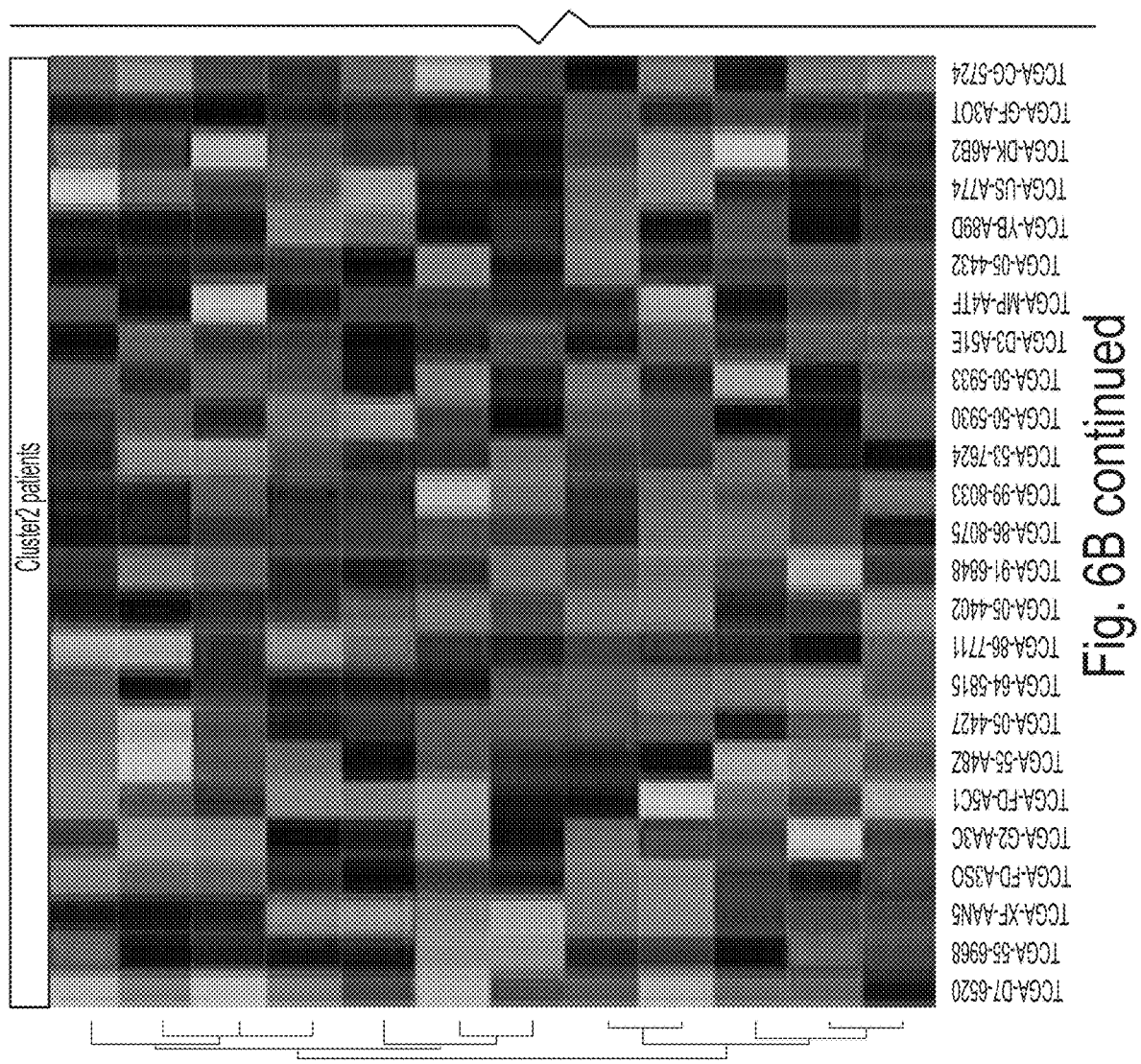
Figure 6B:
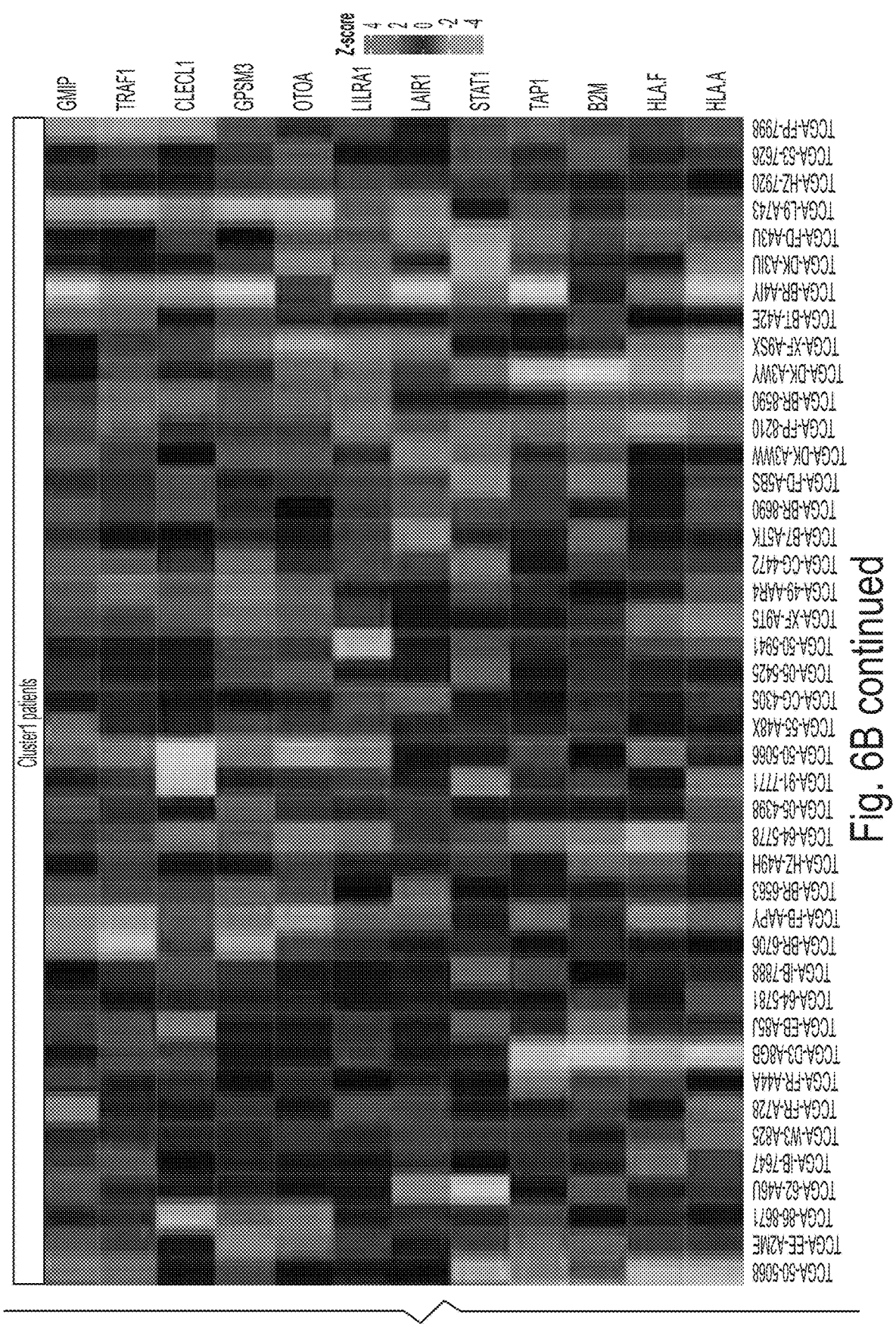

In order to lend further support to the 32-gene signature, the inventors measured the significance of and concordance with another gene set recently suggested as being essential for effector CD8+ T cell activity for immunotherapy. This gene set was identified by a 2CT-CRISPR assay as candidate genes essential for effector CD8+ T cell function and were correlated with cytolytic activity across almost all TCGA cancer types. When the inventors applied k-means clustering, this immunotherapy gene set achieved significance in terms of enrichment for chemosensitive tumor samples (P=0.015; FIG. 6B, Panel D), although this was less significant than that of the 32-gene signature (P=0.0007; FIG. 6B, Panel D). More importantly, however, the concordance or agreement between patient tumor sample clustering by each gene set independently was 'good' (Cohen's kappa=0.64; FIG. 6D), suggesting that the 32-gene signature was able to produce patient tumor sample clusters in concert with those experimentally derived from an immunotherapy gene set important for CD8+ T cell function.

Moreover, and in line with the k-means clustering results, the inventors observed that cluster 1 patients possessed significantly elevated expression for 12 out of the 18 genes identified by the 2CT-CRISPR assay system (acceptable P<0.003; FIG. 6B, Panel E). In concert, pathway network activation revealed cluster 1 patients to possess enriched immune pathway activation via elevated T-Cell Receptor and co-stimulatory signaling, TCR Signaling pathway, and the Inflammatory Response Pathway (P<0.048, P<0.048, and P<0.043, respectively), and these pathways were not enriched in cluster 2 patients. Together these results support the gene signature as a clinically relevant gene expression signature of a 'hot' immunogenic tumor in Treg-enriched patients who may be more likely to respond to checkpoint blockade therapies targeting PD-1 and or CTLA-4.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Moreover, all methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of characterizing a tumor, comprising:
quantifying or obtaining expression strength for a plurality of differentially expressed genes, wherein the genes are differentially expressed in an immune competent cell in the tumor, wherein the plurality of differentially expressed genes comprise at least six of PCDHA5, EFNA5, BARX2, DPP4, CEMP1, SSX1, CD70, LTB, LILRA4, TRAV9.2, GZMM, ZAP70, CD3E, SIRPG, CD3D, SIT1, CD27, CTLA4, ICOS, CD5, GPR171, SH2D1A, TRAT1, ITK, CD3G, RYR1, LAIR2, NTN3, PMCH, GPR1, PLCH2, and BCL11B, and wherein the immune competent cell is a regulatory T cell (Treg);
associating the expression strengths with a cluster representative of overall patient survival, immunogenicity of the tumor, and/or chemosensitivity of the tumor; and
using the association to thereby characterize the tumor as being associated with prolonged overall patient survival, immunogenicity of the tumor, and/or chemosensitivity of the tumor.

2. The method of claim 1, further comprising a step of calculating an immunophenoscore.

3. The method of claim 1, wherein the plurality of differentially expressed genes comprise PCDHA5, EFNA5, BARX2, DPP4, CEMP1, SSX1, CD70, LTB, LILRA4, TRAV9.2, GZMM, ZAP70, CD3E, SIRPG, CD3D, SIT1, CD27, CTLA4, ICOS, CD5, GPR171, SH2D1A, TRAT1, ITK, CD3G, RYR1, LAIR2, NTN3, PMCH, GPR1, PLCH2, and BCL11B.

4. The method of claim 1, wherein the step of quantifying or obtaining expression strength uses previously obtained transcriptomics data.

5. The method of claim 1, wherein the step of quantifying or obtaining expression strength uses a tumor sample.

6. The method of claim 1, wherein the expression strength is determined from RNAseq data.

7. The method of claim 1, wherein the tumor is enriched in Treg cells.

8. The method of claim 1, wherein the tumor is enriched in CD8+ T cells.

9. The method of claim 1, wherein the tumor is enriched in M1 macrophages cells.

10. The method of claim 1, wherein the tumor has elevated expression of a check point marker.

11. The method of claim 1, further comprising a step of determining immune cell composition in the tumor.

12. The method of claim 1, further comprising a step of performing a DNA accessibility prediction on the tumor.

13. The method of claim 1, wherein the plurality of differentially expressed genes are highly differentially expressed genes in Treg cells.

14. The method of claim 1 wherein the cancer is bladder cancer (BLCA), lung adenocarcinoma (LUAD), pancreatic adenocarcinoma (PAAD), skin cutaneous melanoma (SKCM), and stomach adenocarcinoma (STAD).

15. The method of claim 1, further comprising a step of administering chemotherapy upon characterization of the tumor as being chemosensitive.

16. The method of claim 1, further comprising a step of administering immune therapy upon characterization of the tumor as being immunogenic.

\* \* \* \* \*